United States Patent
Wang et al.

(10) Patent No.: US 11,325,900 B2
(45) Date of Patent: May 10, 2022

(54) 5-(PYRIMIDIN-4-YL)THIAZOL-2-YL UREA DERIVATIVES AS THERAPEUTIC AGENTS

(71) Applicant: AUCENTRA HOLDINGS PTY LTD, Dulwich (AU)

(72) Inventors: Shudong Wang, Adelaide (AU); Stephen Philip, Elizabeth South (AU); Mingfeng Yu, Marden (AU)

(73) Assignee: AUCENTRA HOLDINGS PTY LTD, Dulwich (AU)

( * ) Notice: Subject to any disclaimer, the term of this patent is extended or adjusted under 35 U.S.C. 154(b) by 0 days.

(21) Appl. No.: 16/961,986

(22) PCT Filed: Jan. 14, 2019

(86) PCT No.: PCT/AU2019/000005
§ 371 (c)(1),
(2) Date: Jul. 14, 2020

(87) PCT Pub. No.: WO2019/136514
PCT Pub. Date: Jul. 18, 2019

(65) Prior Publication Data
US 2021/0070746 A1    Mar. 11, 2021

(30) Foreign Application Priority Data
Jan. 15, 2018   (AU) ................................ 2018900114

(51) Int. Cl.
*C07D 417/04*   (2006.01)
*C07D 417/14*   (2006.01)

(52) U.S. Cl.
CPC ......... *C07D 417/04* (2013.01); *C07D 417/14* (2013.01)

(58) Field of Classification Search
CPC ............................ C07D 417/04; C07D 417/14
USPC ...................................................... 514/235.8
See application file for complete search history.

(56) References Cited

U.S. PATENT DOCUMENTS

2004/0063946 A1   4/2004   Ohkawa et al.

FOREIGN PATENT DOCUMENTS

| EP | 1 402 900 A1 | 3/2004 |
|---|---|---|
| WO | 2000/026203 A1 | 5/2000 |
| WO | 2004/096797 A1 | 11/2004 |
| WO | 2005/116025 A2 | 12/2005 |
| WO | 2006/084017 A2 | 8/2006 |

OTHER PUBLICATIONS

Extended European Search Report (EESR) issued in corresponding European patent application EP19738966.1, dated May 11, 2021.
Pelish, H.E. et al. "Mediator Kinase Inhibition Further Activates Super-Enhancer Associated Genes in AML", Nature. Oct. 8, 2015; 526(7572): 273-276.
Philip, S. et al. "Cyclin-Dependent Kinase 8: A New Hope in Targeted Cancer Therapy?", J. Med. Chem. 2018, 61, 5073-5092.
International Search Report and Written Opinion dated Feb. 19, 2019, from International Application No. PCT/AU2019/000005, 10 pages.

*Primary Examiner* — Kahsay Habte
(74) *Attorney, Agent, or Firm* — Meunier Carlin & Curfman LLC

(57) ABSTRACT

A novel class of inhibitors of protein kinases useful in the treatment of proliferative cell diseases and conditions including cancers, and especially those characterised by over-expression of CDK8 and/or one or more aberrant CDK8 activity, including certain cancers of lung, breast, brain, ovary, prostate, colorectal cancer and leukaemias. The inhibitors have the general structure I.

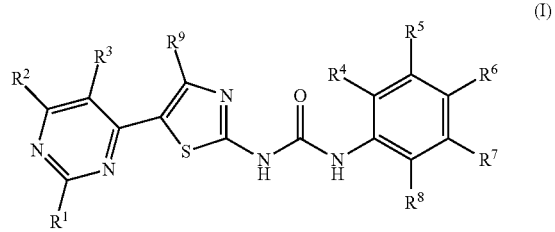

25 Claims, No Drawings

5-(PYRIMIDIN-4-YL)THIAZOL-2-YL UREA DERIVATIVES AS THERAPEUTIC AGENTS

PRIORITY DOCUMENT

The present application claims priority from Australian Provisional Patent Application No 2018900114 titled "5-(pyrimidin-4-yl)thiazol-2-yl urea derivatives as therapeutic agents" filed on 15 Jan. 2018, the content of which is hereby incorporated by reference in its entirety.

TECHNICAL FIELD

The present invention relates to a novel class of inhibitors of protein kinases useful in the treatment of proliferative cell diseases and conditions including cancers.

BACKGROUND

Protein kinases regulate various biological functions, including DNA replication, transcription, translation, cell cycle progression, energy metabolism, migration, and cell growth, making them excellent targets for treating proliferative diseases and conditions including cancers. New compounds, which inhibit the activity of protein kinases and are effective as therapeutic anti-proliferative agents, are still needed.

Cyclin-dependent kinases (CDKs) are serine-threonine protein kinases that associate with various cyclin subunits. There are more than 20 CDKs which may be classified according to their main functions. That is, CDK1, CDK2, CDK3, CDK4 and CDK6 and their cyclin partners (eg cyclin A, B, D1, D2, D3, E and F) are known to be involved in the control of cell cycle progression, and are thus considered to be cell cycle regulators. On the other hand, CDK7, CDK8, CDK9 and CDK11 and their associated cyclin partners (eg cyclin C, H, K, L1, L2, T1 and T2), are considered to be transcriptional regulators. CDKs are thus involved in the regulation of cell-cycle control, apoptosis, neuronal physiology, differentiation, and transcription. As such, the use of CDK inhibitors in the treatment of various diseases, including cancers, cardiovascular disorders, inflammatory diseases, neurodegenerative diseases and viral diseases, is of considerable interest.

In the context of the present invention, of particular interest is the role of CDK8/cyclin C in certain cancers and other proliferative cell diseases and conditions. CDK8 has been reported to be an oncogene particularly associated with colorectal cancer (Firestein R et al., *Nature* 455(7212):547-551, 2008); the CDK8 gene has been shown to be amplified in human colorectal tumors, activating β-catenin-mediated transcription that drives colon tumorigenesis. However, in other cell types, it is thought that CDK8 may act as a tumor suppressor (Fryer C J et al., *Molecular Cell* 16(4):509-520, 2004), particularly within the notch and EGFR signaling pathways (Grants J M et al., *Genetics* 202(2):583-599), and/or promotes transcriptional activation mediated by the tumor suppressor protein p53. Reflecting the need to further elucidate the function of CDK8 in various cell types and tissues, it is believed that there has been no human testing to date of any potential therapeutic agents specifically targeting CDK8. The natural product cortistatin A is, however, known to be a potent and selective inhibitor of CDK8 (Pelish H E et al., *Nature* 526(7572):273-276, 2015), and has been shown to suppress cell growth in acute myeloid leukaemia (AML) cell lines. Moreover, it has been reported that cortistatin A shows anticancer activity in a mouse model of AML, and that this is achieved by causing selective up-regulation of super-enhancer (SE)-associated genes with tumour suppressor and lineage-controlling functions such as CEBPA, IRF8, IRF1 and ETV6 (Pelish et al., supra). Overall, the role of CDK8 in cancer and the use of CDK8 inhibitors in therapeutics has been described (Philip S et al., *J. Med Chem* 61(12):5073-5092, 2018).

The present applicant has now identified a new class of pyrimidine compounds, particularly novel 5-(pyrimidin-4-yl)thiazol-2-yl urea compounds, which inhibit at least the CDK8 protein kinase and may therefore be useful in the prevention and/or treatment of various diseases and conditions including proliferative diseases and conditions such as cancers.

SUMMARY

According to a first aspect, the present invention provides a compound of formula I shown below:

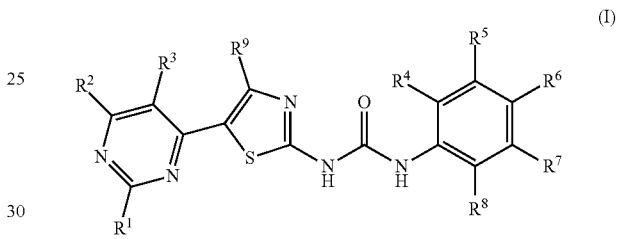

wherein:
$R^1$, $R^2$, $R^3$, $R^4$, $R^5$, $R^6$, $R^7$, $R^8$ and $R^9$ are each independently selected from the group consisting of H, alkyl, alkyl-$R^{10}$, aralkyl, aralkyl-$R^{10}$, heteroalkyl, cycloalkyl, heterocycloalkyl, aryl, aryl-$R^{10}$, heteroaryl, halogen, $NO_2$, CHO, CN, $CHF_2$, $CF_3$, OH, O, O—$CHF_2$, O—$CF_3$, O-alkyl, O-alkyl-$R^{10}$, O-heteroalkyl, O-cycloalkyl, O-heterocycloalkyl, O-aryl, -heteroaryl, O—$R^{10}$, $NH_2$, NH-alkyl, NH-alkyl-$R^{10}$, NH-heteroalkyl, NH-cycloalkyl, NH-heterocycloalkyl, NH-aryl, NH-heteroaryl, NH—$R^{10}$, N-(alkyl), N-(heteroalkyl)$_2$, N-(cycloalkyl)$_2$, N-(heterocycloalkyl)$_2$, N-(aryl)$_2$, N-(heteroaryl)$_2$, N—$(R^{10})(R^{11})$, N-(alkyl)$(R^{10})$, N-(alkyl)(aryl), N-(heteroalkyl)$(R^{10})$, N-(cycloalkyl)$(R^{10})$, N-(heterocycloalkyl)$(R^{10})$, N-(aryl)$(R^{10})$, N-(heteroaryl)$(R^{10})$, SH-alkyl, SH-alkyl-$R^{10}$, SH-heteroalkyl, SH-cycloalkyl, SH-heterocycloalkyl, SH-aryl, SH-heteroaryl, S-(alkyl)$_2$, S-heteroalkyl, S—$C_{1-6}$ alkyl (eg S-methyl), S—$CF_3$, $SO_2CF_3$, S-(cycloalkyl)$_2$, S-(heterocycloalkyl)$_2$, S-(aryl)$_2$, S-(heteroaryl)$_2$, S-(alkyl)(aryl), SH—$R^{10}$, S—$(R^{10})(R^{11})$, S-(alkyl)$(R^{10})$, S-(heteroaryl)$(R^{10})$, S-(cycloalkyl)$(R^{10})$, S-(heterocycloalkyl)$(R^{10})$, S-(aryl)$(R^{10})$, S-(heteroaryl)$(R^{10})$, COOH, $CONH_2$, CONH-alkyl, CONH-aryl, CON-(alkyl)$(R^{10})$, CON(aryl)$(R^{10})$, CON(heteroaryl)$(R^{10})$, CONH—$R^{10}$, CON—$(R^{10})(R^{11})$, $SO_3H$, $SO_2$-alkyl, $SO_2$-alkyl-$R^{10}$, $SO_2$-aryl, $SO_2$-aryl-$R^{10}$, $SO_2NH_2$, $SO_2NH$—$R^{10}$, $SO_2N$—$(R^{10})(R^{11})$, CO-alkyl, CO-alkyl-$R^{10}$, CO-aryl, CO-aryl-$R^{10}$, CO—$R^{10}$, $COOR^{10}$, and $R^{12}$,
and wherein $R^{10}$ and $R^{11}$ are each independently selected from the group consisting of H, alkyl, alkyl-$R^{13}$, heteroalkyl, cycloalkyl, heterocycloalkyl, aryl, heteroaryl, halogen, $NO_2$, CN, $CF_3$, OH, O-alkyl, O-alkyl-$R^{13}$, O-heteroalkyl, O-cycloalkyl, O-heterocycloalkyl, O-aryl, O-heteroaryl, O—$R^{13}$, $NH_2$, NH-alkyl, NH-alkyl-$R^{13}$, NH-heteroalkyl, NH-cycloalkyl, NH-heterocycloalkyl, NH-aryl, NH-heteroaryl, NH—$R^{13}$, N-(alkyl)$_2$, N-(heteroalkyl)$_2$, N-(cycloalkyl)$_2$, N-(heterocycloalkyl)$_2$, N-(aryl)$_2$, N-(heteroaryl)$_2$, N—(R$^{13}$)(R$^{14}$), N-(alkyl)(R$^{13}$), N-(heteroalkyl)(R$^{13}$), N-(cycloalkyl)(R$^{13}$), N-(heterocycloalkyl)(R$^{13}$), N-(aryl)(R$^{13}$), N-(heteroaryl)(R$^{13}$), SH-alkyl, SH-alkyl-R$^{13}$, SH-heteroalkyl, SH-cycloalkyl, SH-heterocycloalkyl, SH-aryl, SH-heteroaryl, S-(alkyl)$_2$, S-(cycloalkyl)$_2$, S-(heterocycloalkyl)$_2$, S-(aryl)$_2$, S-(heteroaryl)$_2$, S-(alkyl)(aryl), SH—R$^{13}$, S—(R$^{13}$)(R$^{14}$), S-(alkyl)(R$^{13}$), S-(heteroaryl)(R$^{13}$), S-(cycloalkyl)(R$^{13}$), S-(heterocycloalkyl)(R$^{13}$), S-(aryl)(R$^{13}$), S-(heteroaryl)(R$^{13}$), COOH, COO-alkyl, CONH$_2$, CONH-alkyl, CONH-aryl, CON-(alkyl)(R$^{13}$), CON(aryl)(R$^{13}$), CON(heteroaryl)(R$^{13}$), CONH—R$^{13}$, CON—(R$^{13}$)(R$^{14}$), SO$_3$H, SO$_2$-alkyl, SO$_2$-alkyl-R$^{13}$, SO$_2$-aryl, SO$_2$-aryl-R$^{13}$, SO$_2$NH$_2$, SO$_2$NH—R$^{13}$, SO$_2$N—(R$^{13}$)(R$^{14}$), CO-alkyl, CO-alkyl-R$^{13}$, CO-aryl, CO-aryl-R$^{13}$, CO—R$^{13}$, COOR$^{13}$, and R$^{12}$, and wherein said heterocycloalkyl and heteroaryl groups comprise at least one but no more than two heteroatoms selected from N, S and O, and wherein said alkyl, heteroalkyl, cycloalkyl, heterocycloalkyl, aralkyl, aryl and heteroaryl groups may be optionally substituted with one or more groups selected from halogen, CN, OH, O-methyl, C$_{1-6}$ alkyl (eg methyl, ethyl or isopropyl), NH$_2$, N—(C$_{1-6}$ alkyl)$_2$, COOH, CO—C$_{1-6}$ alkyl, CONH$_2$, SO$_2$—C$_{1-6}$alkyl, CF$_3$; and R$^{12}$, R$^{13}$ and R$^{14}$ are independently selected from water solubilising groups;

or a pharmaceutically acceptable salt, solvate or prodrug thereof.

In a second aspect, the present invention provides the use of a compound as defined in the first aspect or a pharmaceutically acceptable salt, solvate or prodrug thereof, for treating cancer or another proliferative cell disease or condition.

In a third aspect, the present invention provides a method of treating cancer or another proliferative cell disease or condition in a subject, the method comprising administering to said subject a therapeutically effective amount of a compound as defined in the first aspect or a pharmaceutically acceptable salt, solvate or prodrug thereof, optionally in combination with a pharmaceutically acceptable carrier, diluent and/or excipient.

In a fourth aspect, the present invention provides the use of a compound as defined in the first aspect, or a pharmaceutically acceptable salt, solvate or prodrug thereof, in the manufacture of a medicament for treating cancer or another proliferative cell disease or condition.

In a fifth aspect, the present invention provides a pharmaceutical composition or medicament comprising a compound as defined in the first aspect and a pharmaceutically acceptable carrier, diluent and/or excipient.

In a sixth aspect, the present invention provides a method for modulating protein kinase activity in a cell, comprising introducing to or contacting said cell with an effective amount of a compound as defined in the first aspect or a pharmaceutically acceptable salt, solvate or prodrug thereof.

In a seventh aspect, the present invention provides the use of a compound as defined in the first aspect or a pharmaceutically acceptable salt, solvate or prodrug thereof, for treating a disease or condition in a subject, wherein said disease or condition may be characterised by over-expression of CDK8 and/or one or more aberrant CDK8 activity.

In an eighth aspect, the present invention provides a method of treating a disease or condition in a subject, wherein said disease or condition may be characterised by over-expression of CDK8 and/or one or more aberrant CDK8 activity, the method comprising administering to said subject a therapeutically effective amount of a compound as defined in the first aspect or a pharmaceutically acceptable salt, solvate or prodrug thereof, optionally in combination with a pharmaceutically acceptable carrier, diluent and/or excipient.

In a ninth aspect, the present invention provides the use of a compound as defined in the first aspect, or a pharmaceutically acceptable salt, solvate or prodrug thereof, in the manufacture of a medicament for treating a disease or condition in a subject, wherein said disease or condition may be characterised by over-expression of CDK8 and/or one or more aberrant CDK8 activity.

DETAILED DESCRIPTION

The present applicant has now identified a class of 5-(pyrimidin-4-yl)thiazol-2-yl urea derivatives suitable for use in the prevention and/or treatment of various diseases and conditions including proliferative cell diseases and conditions such as cancers, which possess desirable biological activity (eg the compounds may inhibit cell proliferation by inhibiting the activity of CDKs such as CDK8).

In a first aspect, the present invention provides a compound of formula I shown below:

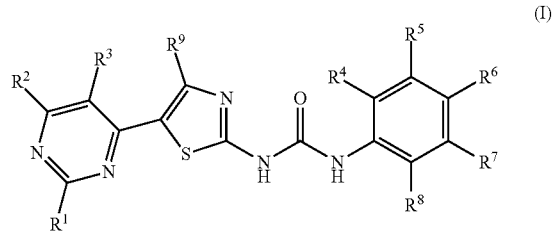

wherein:
R$^1$, R$^2$, R, R$^4$, R$^5$, R$^6$, R$^7$, R$^8$ and R$^9$ are each independently selected from the group consisting of H, alkyl, alkyl-R$^{10}$, aralkyl, aralkyl-R$^{10}$, heteroalkyl, cycloalkyl, heterocycloalkyl, aryl, aryl-R$^{10}$, heteroaryl, halogen, NO$_2$, CHO, CN, CH(alkyl)$_2$ (eg CH(methyl)$_2$), CHF$_2$, CF$_3$, OH, O, O—CHF$_2$, O—CF$_3$, O-alkyl, O-alkyl-R$^{10}$, O-heteroalkyl, O-cycloalkyl, O-heterocycloalkyl, O-aryl, O-heteroaryl, O—R$^{10}$, NH$_2$, NH-alkyl, NH-alkyl-R$^{10}$, NH-heteroalkyl, NH-cycloalkyl, NH-heterocycloalkyl, NH-aryl, NH-heteroaryl, NH—R$^{10}$, N-(alkyl)$_2$, N-(heteroalkyl)$_2$, N-(cycloalkyl)$_2$, N-(heterocycloalkyl)$_2$, N-(aryl)$_2$, N-(heteroaryl)$_2$, N—(R$^{10}$)(R$^{11}$), N-(alkyl)(R$^{10}$), N-(alkyl)(aryl), N-(heteroalkyl)(R$^{10}$), N-(cycloalkyl)(R$^{10}$), N-(heterocycloalkyl)(R$^{10}$), N-(aryl)(R$^{10}$), N-(heteroaryl)(R$^{10}$), SH-alkyl, SH-alkyl-R$^{10}$, SH-heteroalkyl, SH-cycloalkyl, SH-heterocycloalkyl, SH-aryl, SH-heteroaryl, S-(alkyl)$_2$, S-heteroalkyl, S—C$_{1-6}$ alkyl (eg S-methyl), S—CF$_3$, SO$_2$CF$_3$, S-(cycloalkyl)$_2$, S-(heterocycloalkyl)$_2$, S-(aryl)$_2$, S-(heteroaryl)$_2$, S-(alkyl)(aryl), SH—R$^{10}$, S—(R$^{10}$)(R$^{11}$), S-(alkyl)(R$^{10}$), S-(heteroaryl)(R$^{10}$), S-(cycloalkyl)(R$^{10}$), S-(heterocycloalkyl)(R$^{10}$), S-(aryl)(R$^{10}$), S-(heteroaryl)(R$^{10}$), COOH, CONH$_2$, CONH-alkyl, CONH-aryl, CON-(alkyl)(R$^{10}$), CON(aryl)(R$^{10}$), CON(heteroaryl)(R$^{10}$) CONH—R$^{10}$, CON—(R$^{10}$)(R$^{11}$), SO$_3$H, SO$_2$-alkyl, SO$_2$-alkyl-R$^{10}$, SO$_2$-aryl, SO$_2$-aryl-R$^{10}$, SO$_2$NH$_2$, SO$_2$NH—R$^{10}$, SO$_2$N—(R$^{10}$)(R$^{11}$), CO-alkyl, CO-alkyl-R$^{10}$, CO-aryl, CO-aryl-R$^{10}$, CO—R$^{10}$, COOR$^{10}$, and R$^{12}$, and wherein R$^{10}$ and R$^{11}$ are each independently selected from the group consisting of H, alkyl, alkyl-R$^{13}$, heteroalkyl, cycloalkyl, heterocycloalkyl, aryl, heteroaryl, halogen, NO$_2$, CN, CF$_3$, OH, O-alkyl, O-alkyl-R$^{13}$, O-heteroalkyl, O-cycloalkyl, O-heterocycloalkyl, O-aryl, O-heteroaryl, O—R$^{13}$, NH$_2$, NH-alkyl, NH-alkyl-R$^{13}$, NH-heteroalkyl, NH-cycloalkyl, NH-heterocycloalkyl, NH-aryl, NH-heteroaryl, NH—R$^{13}$, N-(alkyl)$_2$, N-(heteroalkyl)$_2$, N-(cycloalkyl)$_2$, N-(heterocycloalkyl)$_2$, N-(aryl)$_2$, N-(heteroaryl)$_2$, N—(R$^{13}$)(R$^{14}$), N-(alkyl)(R$^{13}$), N-(heteroalkyl)(R$^{13}$), N-(cycloalkyl)(R$^{13}$), N-(heterocycloalkyl)(R$^{13}$), N-(aryl)(R$^{13}$), N-(heteroaryl)(R$^{13}$), SH-alkyl, SH-alkyl-R$^{13}$, SH-heteroalkyl, SH-cycloalkyl, SH-heterocycloalkyl, SH-aryl, SH-heteroaryl, S-(alkyl)$_2$, S-(cycloalkyl)$_2$, S-(heterocycloalkyl)$_2$, S-(aryl)$_2$, S-(heteroaryl)$_2$, S-(alkyl)(aryl), SH—R$^{13}$, S—(R$^{13}$)(R$^{14}$), S-(alkyl)(R$^{13}$), S-(heteroaryl)(R$^{13}$), S-(cycloalkyl)(R$^{13}$), S-(heterocycloalkyl)(R$^{13}$), S-(aryl)(R$^{13}$), S-(heteroaryl)(R$^{13}$), COOH, COO-alkyl, CONH$_2$, CONH-alkyl, CONH-aryl, CON-(alkyl)(R$^{13}$), CON(aryl)(R$^{13}$), CON(heteroaryl)(R$^{13}$), CONH—R$^{13}$, CON—(R$^{13}$)(R$^{14}$), SO$_3$H, SO$_2$-alkyl, SO$_2$-alkyl-R$^{13}$, SO$_2$-aryl, SO$_2$-aryl-R$^{13}$, SO$_2$NH$_2$, SO$_2$NH—R$^{13}$, SO$_2$N—(R$^{13}$)(R$^{14}$), CO-alkyl, CO-alkyl-R$^{13}$, CO-aryl, CO-aryl-R$^{13}$, CO—R$^{13}$, COOR$^{13}$, and R$^{12}$,
and wherein said heterocycloalkyl and heteroaryl groups comprise at least one but no more than two heteroatoms selected from N, S and O, and wherein said alkyl, heteroalkyl, cycloalkyl, heterocycloalkyl, aralkyl, aryl and heteroaryl groups may be optionally substituted with one or more groups selected from halogen, CN, OH, O-methyl, C$_{1-6}$ alkyl (eg methyl, ethyl or isopropyl), NH$_2$, N—(C$_{1-6}$ alkyl)$_2$, COOH, CO—C$_{1-6}$ alkyl, CONH$_2$, SO$_2$—C$_{1-6}$ alkyl, CF$_3$; and
R$^{12}$, R$^{13}$ and R$^{14}$ are independently selected from water solubilising groups;
or a pharmaceutically acceptable salt, solvate or prodrug thereof.

Preferably, the compound of the first aspect is not N-[5-(2-methyl-4-pyrimidinyl)-4-(3-methylphenyl)-1,3-thiazol-2-yl]-N'-phenylurea.

The compounds of formula I are believed to possess anti-proliferative activity and are therefore considered to be of use in the treatment of proliferative cell diseases and conditions such as cancers (including, for example, colorectal cancer, leukaemia and lymphoma) and other diseases and conditions associated with uncontrolled cell proliferation such as, for example, some cardiovascular diseases or conditions such as restenosis and cardiomyopathy, some autoimmune diseases such as glomerulonephritis and rheumatoid arthritis, dermatological conditions such as psoriasis, and fungal or parasitic disorders. As used herein, an anti-proliferative effect within the scope of the present invention may be demonstrated by the ability to inhibit cell proliferation in an in vitro whole cell assay.

Thus, in a second aspect, the present invention provides the use of a compound as defined in the first aspect or a pharmaceutically acceptable salt, solvate or prodrug thereof, for treating cancer or another proliferative cell disease or condition.

In a third aspect, the present invention provides a method of treating cancer or another proliferative cell disease or condition in a subject, the method comprising administering to said subject a therapeutically effective amount of a compound as defined in the first aspect or a pharmaceutically acceptable salt, solvate or prodrug thereof, optionally in combination with a pharmaceutically acceptable carrier, diluent and/or excipient.

Ina fourth aspect, the present invention provides the use of a compound as defined in the first aspect, or a pharmaceutically acceptable salt, solvate or prodrug thereof, in the manufacture of a medicament for treating cancer or another proliferative cell disease or condition.

In a fifth aspect, the present invention provides a pharmaceutical composition or medicament comprising a compound as defined in the first aspect and a pharmaceutically acceptable carrier, diluent and/or excipient.

In a sixth aspect, the present invention provides a method for modulating protein kinase activity in a cell, comprising introducing to or contacting said cell with an effective amount of a compound as defined in the first aspect or a pharmaceutically acceptable salt, solvate or prodrug thereof.

As mentioned above, the compounds of the first aspect are considered to inhibit at least the CDK8 protein kinase.

Thus, in a seventh aspect, the present invention provides the use of a compound as defined in the first aspect or a pharmaceutically acceptable salt, solvate or prodrug thereof, for treating a disease or condition in a subject. The said disease or condition may be characterised by over-expression of CDK8 and/or one or more aberrant CDK8 activity. Otherwise, said disease or condition may be one which may be beneficially treated by inhibiting CDK8 (eg by inhibiting CDK8 activity, association with cyclin C/mediator complex and/or expression).

Where a disease or condition to be treated is associated with CDK8 over-expression (eg through CDK8 amplification), the over-expression may occur in one or more tissues, especially tissues affected by the disease or condition (eg colorectal tissues). Similarly, where a disease or condition to be treated is associated with an aberrant CDK8 activity, that aberrant activity may occur in one or more tissues, especially tissues affected by the disease or condition (eg acute myeloid leukaemia, colorectal tissues).

Examples of aberrant CDK8 activity include enhanced or diminished binding and/or phosphorylation of transcription factors, and/or enhanced or diminished association with cyclin C and/or their mediator complex.

In an eighth aspect, the present invention provides a method of treating a disease or condition in a subject, wherein said disease or condition may be characterised by over-expression of CDK8 and/or one or more aberrant CDK8 activity, the method comprising administering to said subject a therapeutically effective amount of a compound as defined in the first aspect or a pharmaceutically acceptable salt, solvate or prodrug thereof, optionally in combination with a pharmaceutically acceptable carrier, diluent and/or excipient.

Ina ninth aspect, the present invention provides the use of a compound as defined in the first aspect, or a pharmaceutically acceptable salt, solvate or prodrug thereof, in the manufacture of a medicament for treating a disease or condition in a subject, wherein said disease or condition may be characterised by over-expression of CDK8 and/or one or more aberrant CDK8 activity.

In this specification, a number of terms are used which are well known to those skilled in the art. Nevertheless, for the purposes of clarity, a number of these terms are hereinafter defined.

As used herein, the term "treating" includes prophylaxis as well as the alleviation of established symptoms of a condition. As such, the act of "treating" a disease or condition therefore includes: (1) preventing or delaying the appearance of clinical symptoms of the disease or condition developing in a subject afflicted with or predisposed to the disease or condition; (2) inhibiting the disease or condition (ie arresting, reducing or delaying the development of the disease or condition or a relapse thereof (in case of a maintenance treatment) or at least one clinical or subclinical symptom thereof; and (3) relieving or attenuating the disease or condition (ie causing regression of the disease or condition or at least one of its clinical or subclinical symptoms).

As used herein, the term "alkyl" includes both straight chain and branched alkyl groups having from 1 to 8 carbon atoms (eg methyl, ethyl propyl, isopropyl, butyl, isobutyl, tert-butyl, pentyl, hexyl etc).

As used herein, the term "heteroalkyl" refers to both straight chain and branched alkyl groups wherein one or more carbon atoms are replaced by an O-, N- or S-atom (eg 1-methoxypropanyl, methyl propionate etc).

As used herein, the term "cycloalkyl" represents cyclic versions of alkyl (cyclopropyl, cyclopentyl, cyclohexyl etc), and may include fused rings. Cycloalkyl groups are unsubstituted, but may be substituted with those groups typically suitable for alkyl group substituents.

As used herein, the term "heterocycloalkyl" or "heterocyclic" represents a cycloalkyl containing at least one annular carbon and at least one annular heteroatom selected from the group consisting of N, O and S, wherein the ring is not aromatic but can contain unsaturations. The nitrogen and sulfur atoms in a heterocyclic group can be oxidised and the nitrogen atom(s) may optionally be quaternised. The heterocyclic group can be fused to an additional carbocyclic or heterocyclic ring. A heterocyclic group can be attached to the remainder of the molecule at an annular carbon or annular heteroatom.

Additionally, heterocyclic main contain fused rings, but excludes fused systems containing a heteroaryl group as part of the fused ring system. Examples of heterocycloalkyl include, but are not limited to, 1-piperidinyl, 1-piperazinyl, morpholinyl, alkylpiperidinyl etc. Heterocycloalkyl moieties can be unsubstituted or substituted with various substituents known in the art, eg hydroxyl, halogen, alkylamino etc.

As used herein, the term "aryl" refers to a substituted (mono- or poly-) or unsubstituted monoaromatic or polyaromatic group, wherein said polyaromatic group may be fused or unfused. The term therefore includes groups having from 6 to 10 carbon atoms (eg phenyl, naphthyl etc). It is also to be understood that the term "aryl" is synonymous with the term "aromatic".

As used herein, the term "heteroaryl" refers to a substituted (mono- or poly-) or unsubstituted monoaromatic or polyaromatic group wherein polyaromatic group may be fused or unfused; and wherein at least one of the rings is an aromatic ring that contains from one to four heteroatoms selected from N, O and S as ring members (i.e. it contains at least one heteroaromatic ring); and wherein the nitrogen and sulfur atoms can be oxidised and the nitrogen atom(s) can be quaternised. A heteroaryl group can be attached to the remainder of the molecule through an annular carbon or annular heteroatom, and it can be attached through any ring of the heteroaryl moiety, if that moiety is bicyclic, tricyclic or a fused ring system. Illustrative examples of heteroaryl groups include 2-pyridyl, 3-pyridyl, 4-pyridyl, 4-pyrimidyl, 5-indolyl etc.

As used herein, the term "aralkyl" is used as a conjunction of the terms alkyl and aryl as defined above.

As used herein, the term "alicyclic" refers to a cyclic aliphatic group.

The term "aliphatic" takes its normal meaning in the art and includes non-aromatic groups such as alkanes, alkenes and alkynes and substituted derivatives thereof.

The term "halogen" refers to fluoro, chloro, bromo and iodo.

The term "derivative" as used herein, includes any chemical modification of an entity. Illustrative of such chemical modifications is the replacement of hydrogen by a halogen group, an alkyl group, an acyl group or an amino group.

As used herein, the phrase "manufacture of a medicament" includes the use of one or more of the compounds of formula I directly as the medicament or in any stage of the manufacture of a medicament comprising one or more of the compounds of formula I.

Some of the compounds of formula I may exist as single stereoisomers, racemates, and/or mixtures of enantiomers and/or diastereomers. All such single stereoisomers, racemates and mixtures thereof, are encompassed within the scope of the present invention. The isomeric forms such as diastereomers, enantiomers, and geometrical isomers can be separated by physical and/or chemical methods known to those skilled in the art.

The term "pharmaceutically acceptable salt" as used herein, refers to salts that retain the desired biological activity of the compounds of formula I, and include pharmaceutically acceptable acid addition salts and base addition salts. Suitable pharmaceutically acceptable acid addition salts of the compounds of formula I may be prepared from an inorganic acid or from an organic acid. Examples of such inorganic acids are hydrochloric, sulfuric and phosphoric acid. Appropriate organic acids may be selected from aliphatic, cycloaliphatic, aromatic, heterocyclic carboxylic and sulfonic classes of organic acids, examples of which are formic, acetic, propionic, succinic, glycolic, gluconic, lactic, malic, tartaric, citric, fumaric, maleic, alkyl sulfonic and arylsulfonic. Additional information on pharmaceutically acceptable salts can be found in Remington's Pharmaceutical Sciences, 19th Edition, Mack Publishing Co., Easton, Pa. 1995.

In the case of compounds of formula I that are solid, it will be understood by those skilled in the art that the compounds (or pharmaceutically acceptable salts, solvates or prodrugs thereof) may exist in different crystalline or polymorphic forms, all of which are encompassed within the scope of the present invention.

"Prodrug" means a compound that undergoes conversion to a compound of formula I within a biological system, usually by metabolic means (eg by hydrolysis, reduction or oxidation). For example, an ester prodrug of a compound of formula I containing a hydroxyl group may be convertible by hydrolysis in vivo to the compound of formula I. Suitable esters of the compounds of formula I containing a hydroxyl group may be, for example, acetates, citrates, lactates, tartrates, malonates, oxalates, salicylates, propionates, succinates, fumarates, maleates, methylene-bis-P-hydroxynaphthoates, gestisates, isethionates, di-p-toluoyltartrates, methanesulfonates, ethanesulfonates, benzenesulfonates, p-toluenesulfonates, cyclohexylsulfamates and quinates. As another example, an ester prodrug of a compound of formula I containing a carboxy group may be convertible by hydrolysis in vivo to the compound of formula I. Examples of ester prodrugs include those described by Leinweber F J, *Drug Metab Rev* 18:379-439 (1987). Similarly, an acyl prodrug of a compound of formula I containing an amino group may be convertible by hydrolysis in vivo to the compound of formula I Examples of prodrugs for these and other functional groups, including amines, are provided in Prodrugs: challenges and rewards, Valentino J Stella (ed), Springer, 2007.

The term "therapeutically effective amount" or "effective amount" is an amount sufficient to effect beneficial or desired clinical results. A therapeutically effective amount can be administered in one or more administrations. Typically, a therapeutically effective amount is sufficient for treating a disease or condition or otherwise to palliate, ameliorate, stabilise, reverse, slow or delay the progression of a disease or condition such as, for example, cancer or another proliferative cell disease or condition. By way of example only, a therapeutically effective amount of a compound of formula I, or a pharmaceutically acceptable salt, solvate or prodrug thereof, may comprise between about 0.1 and about 250 mg/kg body weight per day, more preferably between about 0.1 and about 100 mg/kg body weight per day and, still more preferably between about 0.1 and about 25 mg/kg body weight per day. However, notwithstanding the above, it will be understood by those skilled in the art that the therapeutically effective amount may vary and depend upon a variety of factors including the activity of the particular compound (or salt, solvate or prodrug thereof), the metabolic stability and length of action of the particular compound (or salt, solvate or prodrug thereof), the age, body weight, sex, health, route and time of administration, rate of excretion of the particular compound (or salt, solvate or prodrug thereof), and the severity of, for example, the cancer or other proliferative cell disease or condition to be treated.

In some embodiments, the compounds of formula I may preferably comprise at least one water solubilising group $R^{12}$, $R^{13}$ and $R^{14}$. Where present, $R^{12}$, $R^{13}$ and $R^{14}$ are preferably independently selected from water solubilising groups of the group consisting of:
(i) mono-, di- and poly-hydroxylated alicyclic groups, di- or poly-hydroxylated aliphatic or aryl groups; N—, O- and/or S-containing heterocyclic groups substituted with one or more hydroxyl or amino groups, aliphatic and aryl groups comprising one or more carboxamide, sulfoxide, sulfone or sulfonamide groups; and halogenated alkylcarbonyl groups;
(ii) COOH, $SO_3H$, $OSO_3H$, $SONHCH_3$, $SONHCH_2CH_3$, $SO_2CH_3$, $SO_2CH_2CH_3$, $PO_3H_2$ and $OPO_3H_2$;
(iii) $NHCO(CH_2)_m[NHCO(CH_2)_{m'}]_p[NHCO(CH_2)_{m''}]_qY$ and $NHCO(CH_2)_tNH(CH_2)_tY$ wherein p and q are each independently selected from integers 0 or 1, and m, m', m'', t and ' are each independently selected from integers 1 to 10, and Y is selected from:
(a) alicyclic, aryl and heterocyclic groups comprising one or more O-, S- or N-heteroatoms, which may further comprise an alkyl bridge (eg a —$CH_2$— or —$CH_2CH_2$— bridge),
(b) alicyclic groups comprising one or more of —O—, $NH_2$, —NH—, =N—, quaternary amine salt, and amidine, and
(c) morpholine, piperazine or 1,4-diazepane groups, each of which may be optionally substituted by one or more substituents selected from $SO_2$-alkyl, alkyl optionally substituted by one or more OH groups, CO-alkyl, aralkyl, COO-alkyl, and an ether group optionally substituted by one or more OH groups;
(iv) $(CH_2)_nNR^{15}COR^{16}$, $(CH_2)_nNR^{15}SO_2R^{16}$ and $SO_2R^{17}$, wherein $R^{15}$ is selected from H and alkyl, $R^{16}$ and $R^{17}$ are each independently selected from alkyl groups optionally comprising one or more heteroatoms and/or optionally substituted with one or more substituents independently selected from OH, $NH_2$, halogen and $NO_2$, and n and n' are each independently selected from integers 0, 1, 2 and 3;
(v) ether and polyether groups optionally substituted with one or more OH groups or one or more Y groups, wherein Y is as defined above at (iii);
(vi) $(CH_2)_rNH_2$, wherein r is selected from integers 0, 1, 2 and 3;
(vii) $(CH_2)_{r'}OH$, wherein r' is selected from integers 0, 1, 2 and 3;

(viii) $(CH_2)_{n''}NR^{18}COR^{19}$, wherein $R^{18}$ is H or alkyl, n" is selected from integers 0, 1, 2 and 3, and $R^{19}$ is an aryl group optionally substituted with one or more substituents selected from halogen, $NO_2$, OH, alkoxy, $NH_2$, COOH, $CONH_2$ and $CF_3$; and
(ix) $SO_2NR^{20}R^{21}$, wherein $R^{20}$ and $R^{21}$ are each independently selected from H, alkyl and aryl, with the proviso that at least one of $R^{20}$ and $R^{21}$ is other than H, or $R^{20}$ and $R^{21}$ together form a cyclic group optionally comprising one or more heteroatoms selected from N, O and S, and wherein said alkyl, aryl or cyclic group is optionally substituted by one or more substituents selected from halogen, $NO_2$, OH, alkoxy, $NH_2$, COOH, $CONH_2$ and $CF_3$.

In some embodiments $R^1$, $R^2$, $R^3$, $R^4$, $R^5$, $R^6$, $R^7$, $R^8$ and $R^9$ are each independently selected from the group consisting of H, alkyl (eg a $C_{1-6}$ alkyl or, preferably, a $C_{1-3}$ alkyl such as methyl), alkyl-$R^{10}$ (eg a $C_{1-6}$ alkyl-$R^{10}$ or a $C_{1-3}$ alkyl-$R^{10}$ such as $CH_2$—$R^{10}$), cycloalkyl, heterocycloalkyl, aryl (eg phenyl), heteroaryl (eg pyridinyl, pyrimidinyl), halogen, $NO_2$, $CH(C_{1-6}$ alkyl$)_2$ (preferably a $CH(C_{1-3}$ alkyl$)_2$), $CHF_2$, $CF_3$, CHO, CN, OH, O, O—$CHF_2$, O—$CF_3$, O-alkyl (eg an O-Cc alkyl, preferably, an O—$C_{1-3}$ alkyl such as O—$CH_3$), O-heteroalkyl, O—$C_{3-8}$ cycloalkyl (such as $O(C_5H_9)$; ie O-cyclopentyl), O-aryl, O-heteroaryl, $NH_2$, NH-alkyl (eg a NH—$C_{1-6}$ alkyl, preferably, a NH—$C_{1-3}$ alkyl such as NH—$CH_3$), NH-heteroalkyl (eg N,N-dimethylethane-1,2-diamine), NH-cycloalkyl (eg a NH—$C_{3-8}$ cycloalkyl such as $NH(C_5H_9)$; ie NH-cyclopentyl), NH-heterocycloalkyl (eg NH—$C_{3-8}$ heterocycloalkyl such as $NH(C_5H_{11}N)$; ie NH-piperidinamine), NH-aryl, NH-heteroaryl, N(alkyl)$_2$ (eg an N($C_{1-6}$ alkyl)$_2$, preferably, a N($C_{1-3}$ alkyl)$_2$ such as N($CH_3$)$_2$), N(cycloalkyl)$_2$ (eg N($C_5H_9$)$_2$), N(heterocycloalkyl)$_2$ (such as N-dipiperidinamine), N-(alkyl)(aryl), SH-alkyl (eg a SH—$C_{1-6}$ alkyl or, preferably, a SH—$C_{1-3}$ alkyl such as $SHCH_3$ and $SHC(CH_3)$), SH-aryl, SH-heteroaryl, S-heteroalkyl, S—$C_{1-6}$ alkyl (preferably a S—$C_3$ alkyl such as S-methyl), S—$CF_3$, $SO_2CF_3$, S—$C_{3-8}$ cycloalkyl (such as $S(C_5H_9)$; ie S-(cyclopentyl)), and $R^{12}$.

In some preferred embodiments, $R^1$ is CH(alkyl)$_2$ (eg a CH($C_{1-6}$ alkyl)$_2$, preferably a CH($C_{1-3}$ alkyl)$_2$ such as CH(methyl)$_2$), $NH_2$, NH-alkyl (eg a NH—$C_{1-6}$ alkyl, preferably, a NH—$C_{1-3}$ alkyl such as NH—$CH_3$), N(alkyl)$_2$ (eg an N($C_{1-6}$ alkyl)$_2$, preferably, a N($C_{1-3}$ alkyl)$_2$ such as N($CH_3$)$_2$) or S—$C_{1-6}$ alkyl (preferably a S—$C_{1-3}$ alkyl such as S-methyl).

In some preferred embodiments, $R^2$ is H.
In some preferred embodiments, $R^3$ is H, halogen (preferably F or Cl) or CN.
In some preferred embodiments, $R^4$ is H.
In some particularly preferred embodiments, $R^2$, $R^3$ and $R^4$ are all H.
In some preferred embodiments, $R^5$ is selected from H, $NH_2$, $C_{1-6}$ alkyl (eg methyl, ethyl or benzyl), halogen (preferably F or Cl), O—$C_{1-3}$ alkyl (eg O-methyl), $CHF_2$, $CF_3$ or CHO.
In some preferred embodiments, $R^6$ is selected from H, $NH_2$, $C_{1-6}$ alkyl (eg methyl, ethyl or benzyl), halogen (preferably F or Cl), O—$C_{1-3}$ alkyl (eg O-methyl), $CHF_2$, $CF_3$ or CHO.
In other embodiments, $R^6$ is selected from $C_{1-3}$ alkyl-$R^{10}$ such as the following:

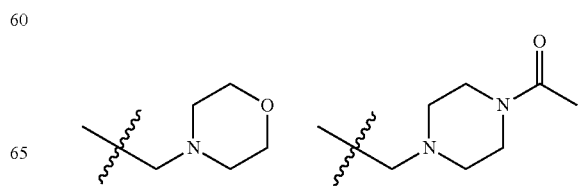

-continued

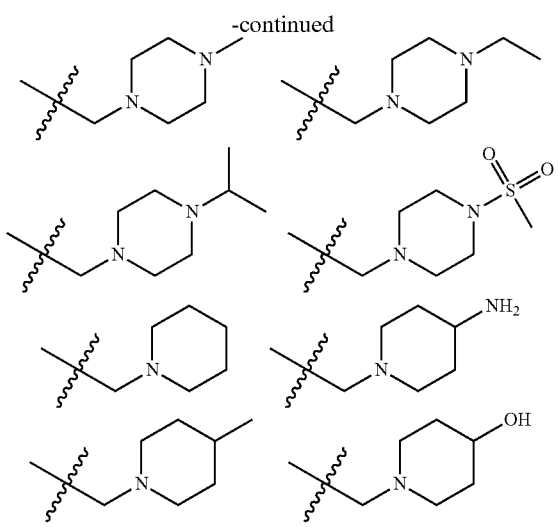

In some preferred embodiments, R⁷ is selected from H, NH₂, NO₂, C₁₋₆ alkyl (eg methyl, ethyl or isopropyl), halogen (preferably F, Br or Cl), O—C₁₋₃ alkyl (eg O-methyl or O-ethyl), CHF₂, O—CHF₂, CF₃, O—CF₃, S—C₁₋₃ alkyl (eg S-methyl), SCF₃, SO₂CF₃, CN or CHO.

In some preferred embodiments, R⁸ is selected from H, NH₂, C₁₋₆ alkyl (eg methyl, ethyl or benzyl), halogen (preferably F or Cl), O—C₁₋₃ alkyl (eg O-methyl), CHF₂, CF₃ or CHO.

In some preferred embodiments, R⁹ is selected from H, NH₂, C₁₋₆ alkyl (eg methyl or ethyl), halogen (preferably F or Cl), O—C₁₋₃alkyl (eg O-methyl), CHF₂, CF₃ or CHO.

In some particularly preferred embodiments, R⁹ is H or a C₁₋₆ alkyl(eg methyl or ethyl).

In some preferred embodiments, the compounds of the present invention exhibit anti-proliferative activity in human cell lines, as measured by a standard cytotoxicity assay. Preferably, the compound exhibits an IC₅₀ value of less than 5 µM, even more preferably less than 1 µM as measured by the cell viability (MTT proliferation) assay described in Example 2 hereinafter. More preferably still, the compound exhibits an IC₅₀ value of less than 0.5 µM.

In some preferred embodiments, the compounds of the present invention inhibit one or more protein kinases, as measured by any standard assay well known to those skilled in the art. Preferably, the compound exhibits an IC₅₀ value of less than 1 µM or less than 0.5 µM as measured by the kinase assay described in Example 2 hereinafter, more preferably still less than 0.1 µM.

Particular examples of compounds according to the first aspect are shown in Table 1 below.

TABLE 1

Chemical structure of selected compounds of the present invention

| No. | Structure | Name | Mass |
|---|---|---|---|
| 1 | 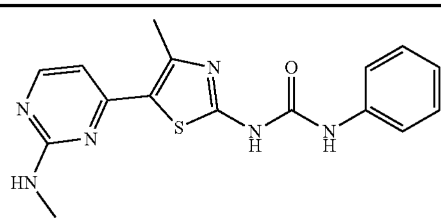 | 1-(4-Methyl-5-(2-(methylamino)pyrimidin-4-yl)thiazol-2-yl)-3-phenylurea | 340.1 |
| 2 | 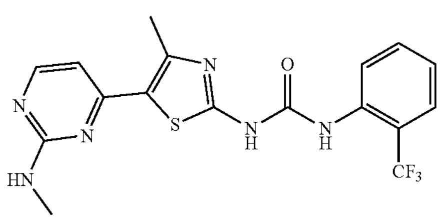 [SMILES: CNc1nccc(-c2sc(NC(=O)Nc3ccccc3C(F)(F)F)nc2C)n1] | 1-(4-Methyl-5-(2-(methylamino)-pyrimidin-4-yl)thiazol-2-yl)-3-(2-(trifluoromethyl)phenyl)urea | 408.1 |
| 3 | 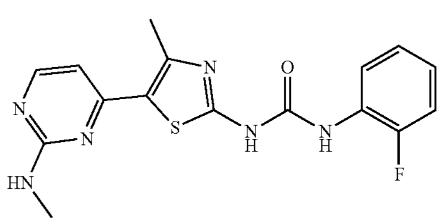 [SMILES: CNc1nccc(-c2sc(NC(=O)Nc3ccccc3F)nc2C)n1] | 1-(2-Fluorophenyl)-3-(4-methyl-5-(2-(methylamino)pyrimidin-4-yl)thiazol-2-yl)urea | 358.1 |
| 4 | 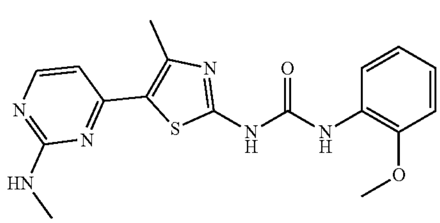 [SMILES: CNc1nccc(-c2sc(NC(=O)Nc3ccccc3OC)nc2C)n1] | 1-(2-Methoxyphenyl)-3-(4-methyl-5-(2-(methylamino)pyrimidin-4-yl)thiazol-2-yl)urea | 370.1 |

TABLE 1-continued

Chemical structure of selected compounds of the present invention

| No. | Structure | Name | Mass |
|---|---|---|---|
| 5 | 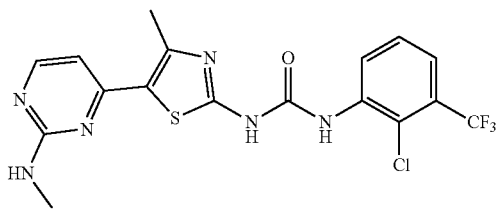 [SMILES: CNc1nccc(-c2sc(NC(=O)Nc3cccc(C(F)(F)F)c3Cl)nc2C)n1] | 1-(3-Chloro-4-(trifluoromethyl)-phenyl)-3-(4-methyl-5-(2-(methylamino)pyrimidin-4-yl)thiazol-2-yl)urea | 442.1 |
| 6 | 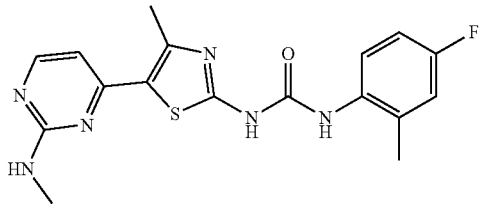 [SMILES: CNc1nccc(-c2sc(NC(=O)Nc3ccc(F)cc3C)nc2C)n1] | 1-(4-Fluoro-2-methylphenyl)-3-(4-methyl-5-(2-(methylamino)-pyrimidin-4-yl)thiazol-2-yl)urea | 372.1 |
| 7 | 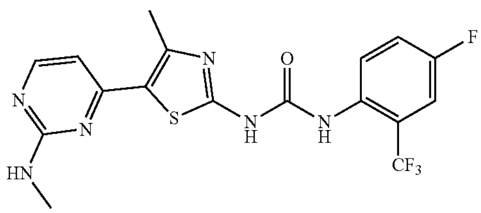 [SMILES: CNc1nccc(-c2sc(NC(=O)Nc3ccc(F)cc3C(F)(F)F)nc2C)n1] | 1-(4-fluoro-2-(trifluoromethyl)-phenyl)-3-(4-methyl-5-(2-(methylamino)-pyrimidin-4-yl)thiazol-2-yl)urea | 426.1 |
| 8 | 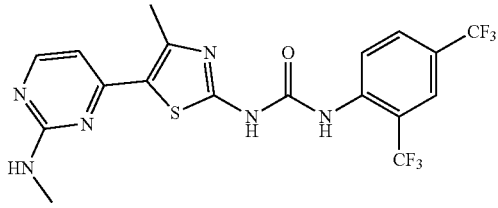 [SMILES: CNc1nccc(-c2sc(NC(=O)Nc3ccc(C(F)(F)F)cc3C(F)(F)F)nc2C)n1] | 1-(2,4-Bis(trifluoromethyl)phenyl)-3-(4-methyl-5-(2-(methylamino)-pyrimidin-4-yl)thiazol-2-yl)urea | 476.1 |
| 9 | 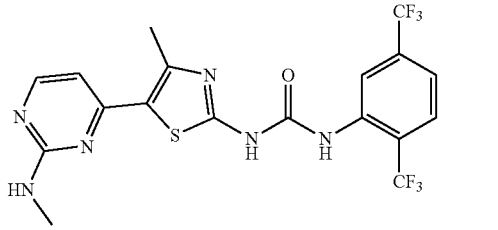 [SMILES: CNc1nccc(-c2sc(NC(=O)Nc3cc(C(F)(F)F)ccc3C(F)(F)F)nc2C)n1] | 1-(2,5-Bis(trifluoromethyl)phenyl)-3-(4-methyl-5-(2-(methylamino)-pyrimidin-4-yl)thiazol-2-yl)urea | 476.1 |
| 10 | 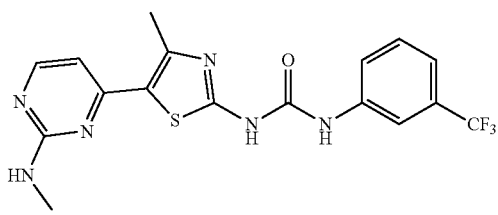 [SMILES: CNc1nccc(-c2sc(NC(=O)Nc3cccc(C(F)(F)F)c3)nc2C)n1] | 1-(4-Methyl-5-(2-(methylamino)-pyrimidin-4-yl)thiazol-2-yl)-3-(3-(trifluoromethyl)phenyl)urea | 408.1 |
| 11 | 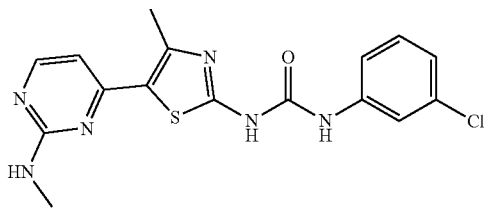 [SMILES: CNc1nccc(-c2sc(NC(=O)Nc3cccc(Cl)c3)nc2C)n1] | 1-(3-Chlorophenyl)-3-(4-methyl-5-(2-(methylamino)pyrimidin-4-yl)thiazol-2-yl)urea | 374.1 |

TABLE 1-continued

Chemical structure of selected compounds of the present invention

| No. | Structure | Name | Mass |
|---|---|---|---|
| 12 | 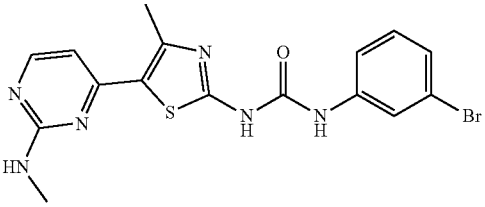 [SMILES: CNc1nccc(-c2sc(NC(=O)Nc3cccc(Br)c3)nc2C)n1] | 1-(3-Bromophenyl)-3-(4-methyl-5-(2-(methylamino)pyrimidin-4-yl)thiazol-2-yl)urea | 418.0 |
| 13 | 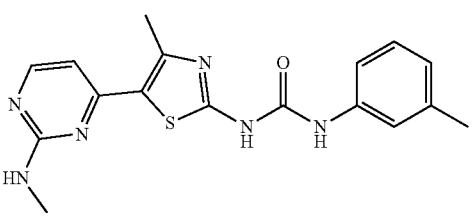 [SMILES: CNc1nccc(-c2sc(NC(=O)Nc3cccc(C)c3)nc2C)n1] | 1-(4-Methyl-5-(2-(methylamino)pyrimidin-4-yl)thiazol-2-yl)-3-(m-tolyl)urea | 354.1 |
| 14 | 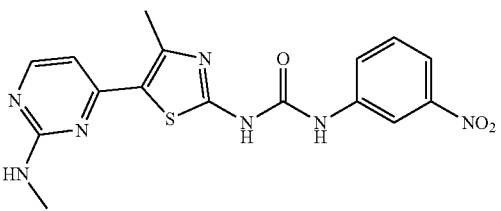 [SMILES: CNc1nccc(-c2sc(NC(=O)Nc3cccc([N+](=O)[O-])c3)nc2C)n1] | 1-(4-Methyl-5-(2-(methylamino)pyrimidin-4-yl)thiazol-2-yl)-3-(3-nitrophenyl)urea | 385.1 |
| 15 | 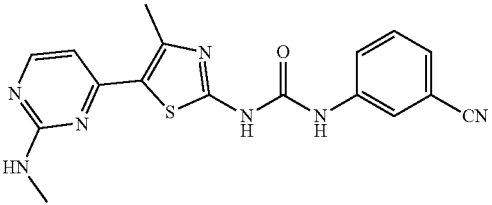 [SMILES: CNc1nccc(-c2sc(NC(=O)Nc3cccc(C#N)c3)nc2C)n1] | 1-(3-Cyanophenyl)-3-(4-methyl-5-(2-(methylamino)pyrimidin-4-yl)thiazol-2-yl)urea | 365.1 |
| 16 | 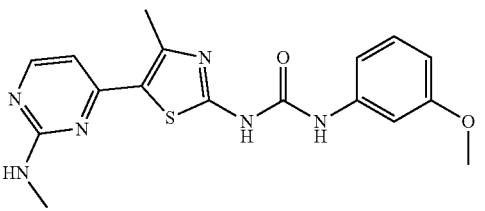 [SMILES: CNc1nccc(-c2sc(NC(=O)Nc3cccc(OC)c3)nc2C)n1] | 1-(3-Methoxyphenyl)-3-(4-methyl-5-(2-(methylamino)pyrimidin-4-yl)thiazol-2-yl)urea | 370.1 |
| 17 | 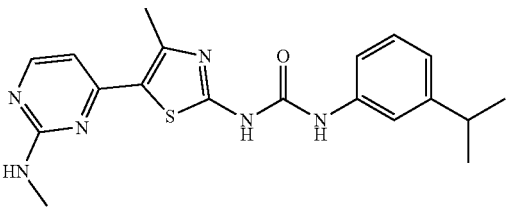 [SMILES: CNc1nccc(-c2sc(NC(=O)Nc3cccc(C(C)C)c3)nc2C)n1] | 1-(3-Isopropylphenyl)-3-(4-methyl-5-(2-(methylamino)pyrimidin-4-yl)thiazol-2-yl)urea | 382.1 |
| 18 | 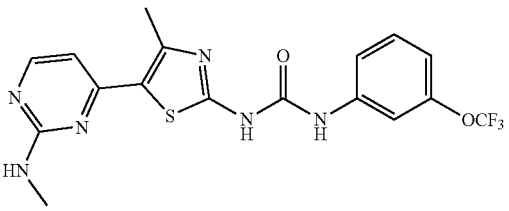 [SMILES: CNc1nccc(-c2sc(NC(=O)Nc3cccc(OC(F)(F)F)c3)nc2C)n1] | 1-(4-Methyl-5-(2-(methylamino)-pyrimidin-4-yl)thiazol-2-yl)-3-(3-(trifluoromethoxy)phenyl)urea | 424.0 |

TABLE 1-continued

Chemical structure of selected compounds of the present invention

| No. | Structure | Name | Mass |
|---|---|---|---|
| 19 | 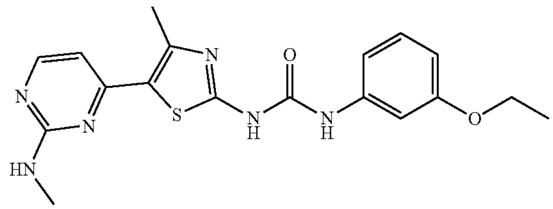 [SMILES: CCOc1cccc(NC(=O)Nc2nc(C)c(-c3ccnc(NC)n3)s2)c1] | 1-(3-Ethoxyphenyl)-3-(4-methyl-5-(2-(methylamino)pyrimidin-4-yl)thiazol-2-yl)urea | 384.1 |
| 20 | 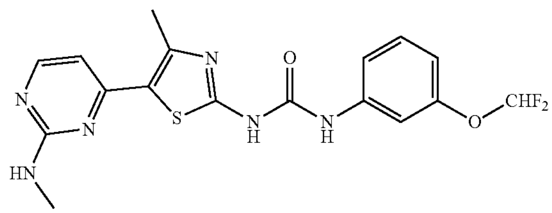 [SMILES: CNc1nccc(-c2sc(NC(=O)Nc3cccc(OC(F)F)c3)nc2C)n1] | 1-(3-(Difluoromethoxy)phenyl)-3-(4-methyl-5-(2-(methylamino)-pyrimidin-4-yl)thiazol-2-yl)urea | 406.1 |
| 21 | 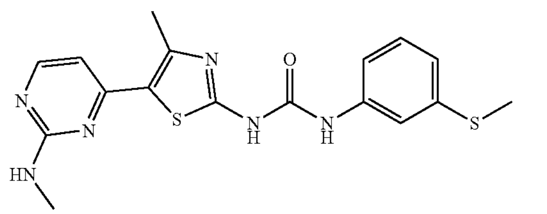 [SMILES: CNc1nccc(-c2sc(NC(=O)Nc3cccc(SC)c3)nc2C)n1] | 1-(4-Methyl-5-(2-(methylamino)-pyrimidin-4-yl)thiazol-2-yl)-3-(3-(methylthio)phenyl)urea | 386.1 |
| 22 | 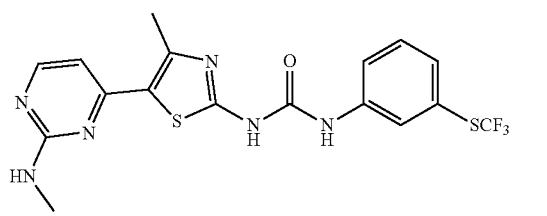 | 1-(4-Methyl-5-(2-(methylamino)-pyrimidin-4-yl)thiazol-2-yl)-3-(3-((trifluoromethyl)thio)phenyl)urea | 440.1 |
| 23 | 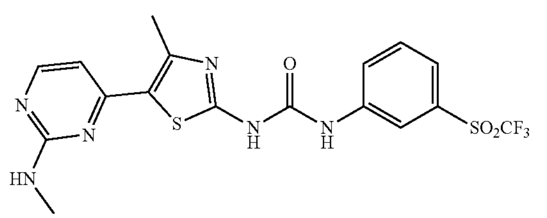 | 1-(4-Methyl-5-(2-(methylamino)pyrimidin-4-yl)-thiazol-2-yl)-3-(3-((trifluoromethyl)-sulfonyl)phenyl)urea | 472.1 |
| 24 | 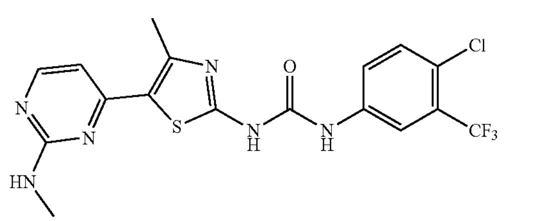 [SMILES: CNc1nccc(-c2sc(NC(=O)Nc3ccc(Cl)c(C(F)(F)F)c3)nc2C)n1] | 1-(4-Chloro-3-(trifluoromethyl)-phenyl)-3-(4-methyl-5-(2-(methylamino)-pyrimidin-4-yl)thiazol-2-yl)urea | 442.0 |
| 25 | 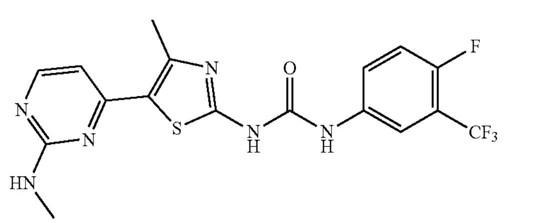 [SMILES: CNc1nccc(-c2sc(NC(=O)Nc3ccc(F)c(C(F)(F)F)c3)nc2C)n1] | 1-(4-Fluoro-3-(trifluoromethyl)phenyl)-3-(4-methyl-5-(2-(methylamino)-pyrimidin-4-yl)thiazol-2-yl)urea | 426.1 |

TABLE 1-continued

Chemical structure of selected compounds of the present invention

| No. | Structure | Name | Mass |
|---|---|---|---|
| 26 | 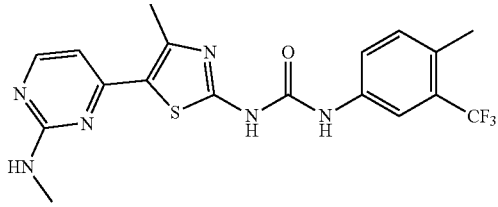 [SMILES: CNc1nccc(-c2sc(NC(=O)Nc3ccc(C)c(C(F)(F)F)c3)nc2C)n1] | 1-(4-Methyl-3-(trifluoromethyl)-phenyl)-3-(4-methyl-5-(2-(methylamino)pyrimidin-4-yl)thiazol-2-yl)urea | 422.1 |
| 27 | 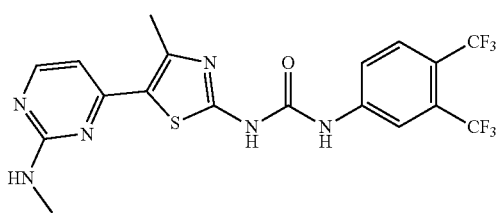 [SMILES: CNc1nccc(-c2sc(NC(=O)Nc3ccc(C(F)(F)F)c(C(F)(F)F)c3)nc2C)n1] | 1-(3,4-Bis(trifluoromethyl)phenyl)-3-(4-methyl-5-(2-(methylamino)-pyrimidin-4-yl)thiazol-2-yl)urea | 476.1 |
| 28 | 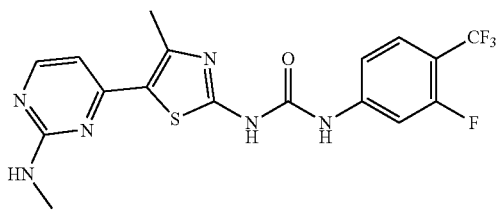 [SMILES: CNc1nccc(-c2sc(NC(=O)Nc3ccc(C(F)(F)F)c(F)c3)nc2C)n1] | 1-(3-Fluoro-4-(trifluoromethyl)phenyl)-3-(4-methyl-5-(2-(methylamino)-pyrimidin-4-yl)thiazol-2-yl)urea | 426.1 |
| 29 | 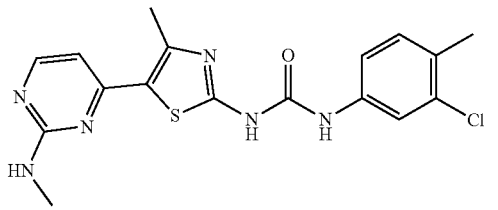 [SMILES: CNc1nccc(-c2sc(NC(=O)Nc3ccc(C)c(Cl)c3)nc2C)n1] | 1-(3-Chloro-4-methylphenyl)-3-(4-methyl-5-(2-(methylamino)-pyrimidin-4-yl)thiazol-2-yl)urea | 388.1 |
| 30 | 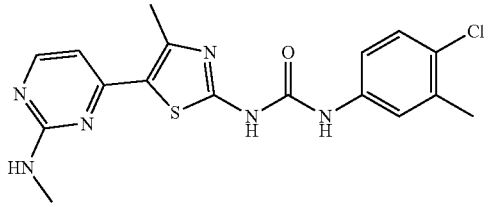 [SMILES: CNc1nccc(-c2sc(NC(=O)Nc3ccc(Cl)c(C)c3)nc2C)n1] | 1-(4-Chloro-3-methylphenyl)-3-(4-methyl-5-(2-(methylamino)-pyrimidin-4-yl)thiazol-2-yl)urea | 388.1 |
| 31 | 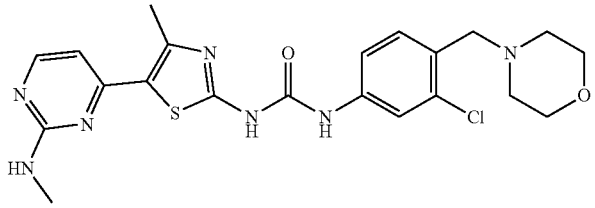 [SMILES: CNc1nccc(-c2sc(NC(=O)Nc3ccc(CN4CCOCC4)c(Cl)c3)nc2C)n1] | 1-(3-Chloro-4-(morpholinomethyl)phenyl)-3-(4-methyl-5-(2-(methylamino)-pyrimidin-4-yl)thiazol-2-yl)urea | 473.1 |
| 32 | 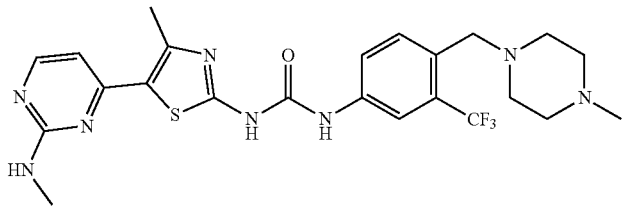 | 1-(4-Methyl-5-(2-(methylamino)-pyrimidin-4-yl)thiazol-2-yl)-3-(4-((4-methylpiperazin-1-yl)methyl)-3-(trifluoromethyl)phenyl)urea | 520.2 |

TABLE 1-continued

Chemical structure of selected compounds of the present invention

| No. | Structure | Name | Mass |
|---|---|---|---|
| 33 | 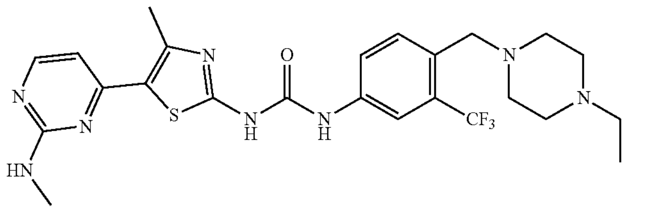 [SMILES: CCN1CCN(Cc2ccc(NC(=O)Nc3nc(C)c(-c4ccnc(NC)n4)s3)cc2C(F)(F)F)CC1] | 1-(4-((4-Ethylpiperazin-1-yl)methyl)-3-(trifluoromethyl)phenyl)-3-(4-methyl-5-(2-(methylamino)-pyrimidin-4-yl)thiazol-2-yl)urea | 534.2 |
| 34 | 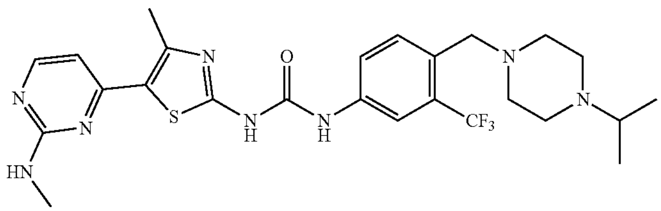 [SMILES: CNc1nccc(-c2sc(NC(=O)Nc3ccc(CN4CCN(C(C)C)CC4)c(C(F)(F)F)c3)nc2C)n1] | 1-(4-((4-Isopropylpiperazin-1-yl)methyl)-3-(trifluoromethyl)-phenyl)-3-(4-methyl-5-(2-(methylamino)pyrimidin-4-yl)thiazol-2-yl)urea | 548.2 |
| 35 | 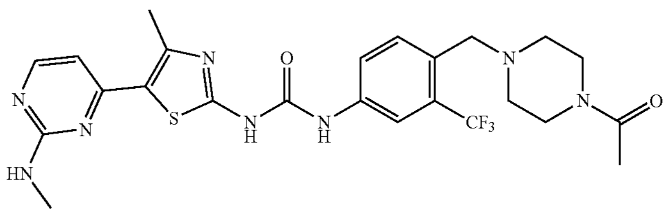 [SMILES: CNc1nccc(-c2sc(NC(=O)Nc3ccc(CN4CCN(C(C)=O)CC4)c(C(F)(F)F)c3)nc2C)n1] | 1-(4-((4-Acetylpiperazin-1-yl)methyl)-3-(trifluoromethyl)-phenyl)-3-(4-methyl-5-(2-(methylamino)pyrimidin-4-yl)thiazol-2-yl)urea | 548.2 |
| 36 | 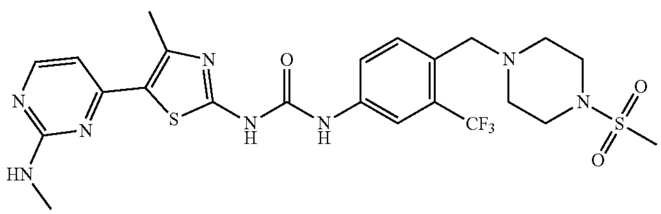 [SMILES: CNc1nccc(-c2sc(NC(=O)Nc3ccc(CN4CCN(S(C)(=O)=O)CC4)c(C(F)(F)F)c3)nc2C)n1] | 1-(4-Methyl-5-(2-(methylamino)-pyrimidin-4-yl)thiazol-2-yl)-3-(4-((4-(methylsulfonyl)piperazin-1-yl)methyl)-3-(trifluoromethyl)-phenyl)urea | 584.2 |
| 37 | 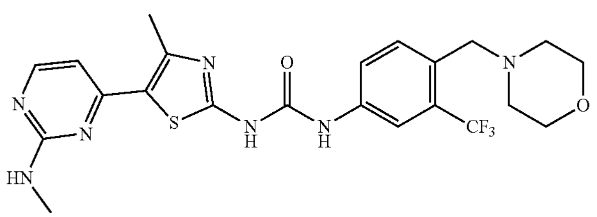 [SMILES: CNc1nccc(-c2sc(NC(=O)Nc3ccc(CN4CCOCC4)c(C(F)(F)F)c3)nc2C)n1] | 1-(4-Methyl-5-(2-(methylamino)-pyrimidin-4-yl)thiazol-2-yl)-3-(4-(morpholinomethyl)-3-(trifluoromethyl)phenyl)urea | 507.2 |
| 38 | 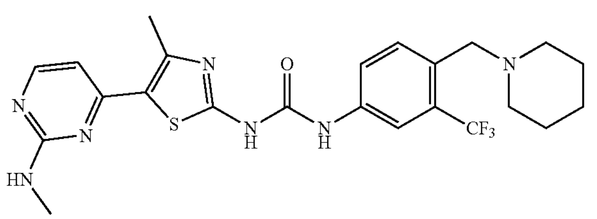 [SMILES: CNc1nccc(-c2sc(NC(=O)Nc3ccc(CN4CCCCC4)c(C(F)(F)F)c3)nc2C)n1] | 1-(4-Methyl-5-(2-(methylamino)-pyrimidin-4-yl)thiazol-2-yl)-3-(4-(piperidin-1-ylmethyl)-3-(trifluoromethyl)phenyl)urea | 505.2 |
| 39 | 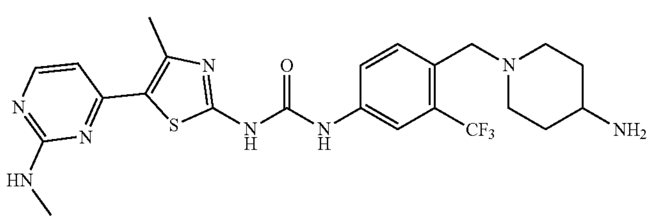 [SMILES: CNc1nccc(-c2sc(NC(=O)Nc3ccc(CN4CCC(N)CC4)c(C(F)(F)F)c3)nc2C)n1] | 1-(4-((4-Aminopiperidin-1-yl)methyl)-3-(trifluoromethyl)-phenyl)-3-(4-methyl-5-(2-(methylamino)pyrimidin-4-yl)thiazol-2-yl)urea | 520.2 |

TABLE 1-continued

Chemical structure of selected compounds of the present invention

| No. | Structure | Name | Mass |
|---|---|---|---|
| 40 | 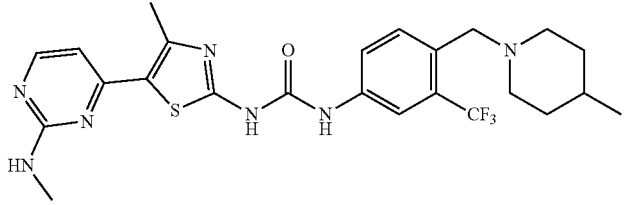 [SMILES: CNc1nccc(-c2sc(NC(=O)Nc3ccc(CN4CCC(C)CC4)c(C(F)(F)F)c3)nc2C)n1] | 1-(4-Methyl-5-(2-(methylamino)-pyrimidin-4-yl)thiazol-2-yl)-3-(4-((4-methylpiperidin-1-yl)methyl)-3-(trifluoromethyl)phenyl)urea | 519.2 |
| 41 | 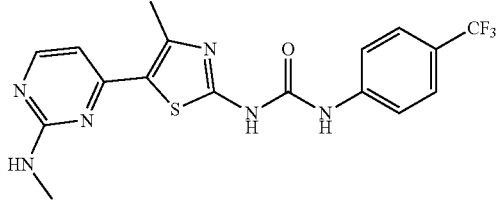 [SMILES: CNc1nccc(-c2sc(NC(=O)Nc3ccc(C(F)(F)F)cc3)nc2C)n1] | 1-(4-Methyl-5-(2-(methylamino)pyrimidin-4-yl)thiazol-2-yl)-3-(4-(trifluoromethyl)phenyl)urea | 408.1 |
| 42 | 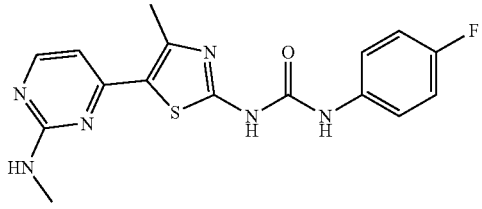 [SMILES: CNc1nccc(-c2sc(NC(=O)Nc3ccc(F)cc3)nc2C)n1] | 1-(4-Fluorophenyl)-3-(4-methyl-5-(2-(methylamino)pyrimidin-4-yl)thiazol-2-yl)urea | 358.1 |
| 43 | 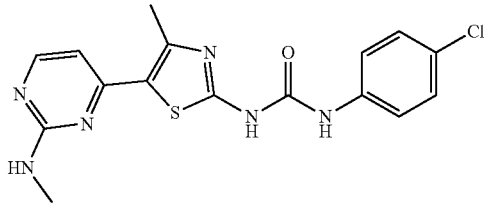 [SMILES: CNc1nccc(-c2sc(NC(=O)Nc3ccc(Cl)cc3)nc2C)n1] | 1-(4-Chlorophenyl)-3-(4-ethyl-5-(2-(methylamino)pyrimidin-4-yl)thiazol-2-yl)urea | 374.1 |
| 44 | 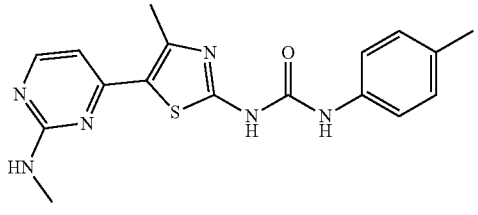 [SMILES: CNc1nccc(-c2sc(NC(=O)Nc3ccc(C)cc3)nc2C)n1] | 1-(4-Methyl-5-(2-(methylamino)pyrimidin-4-yl)thiazol-2-yl)-3-(p-tolyl)urea | 354.1 |
| 45 | 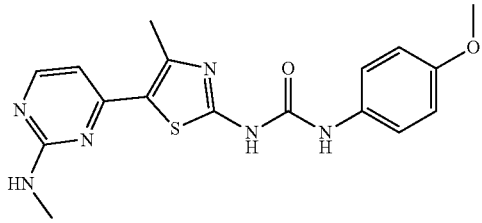 [SMILES: CNc1nccc(-c2sc(NC(=O)Nc3ccc(OC)cc3)nc2C)n1] | 1-(4-Methoxyphenyl)-3-(4-methyl-5-(2-(methylamino)pyrimidin-4-yl)thiazol-2-yl)urea | 370.1 |
| 46 | 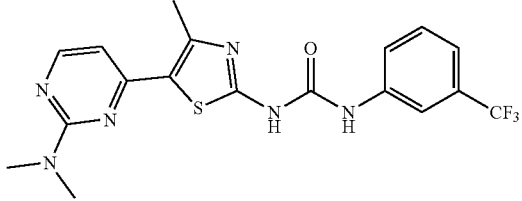 [SMILES: Cc1nc(NC(=O)Nc2cccc(C(F)(F)F)c2)sc1-c1ccnc(N(C)C)n1] | 1-(5-(2-(Dimethylamino)pyrimidin-4-yl)-4-methylthiazol-2-yl)-3-(3-(trifluoromethyl)phenyl)urea | 422.1 |

TABLE 1-continued

Chemical structure of selected compounds of the present invention

| No. | Structure | Name | Mass |
|---|---|---|---|
| 47 | 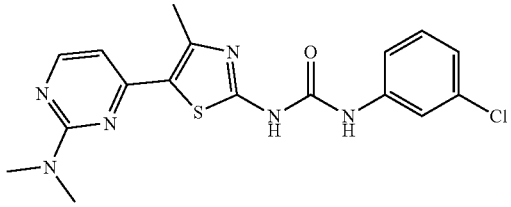 [SMILES: Cc1nc(NC(=O)Nc2cccc(Cl)c2)sc1-c1ccnc(N(C)C)n1] | 1-(3-Chlorophenyl)-3-(5-(2-(dimethylamino)pyrimidin-4-yl)-4-methylthiazol-2-yl)urea | 388.1 |
| 48 | 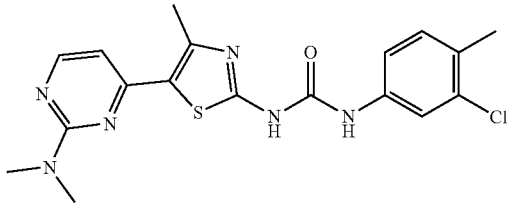 | 1-(3-Chloro-4-methylphenyl)-3-(5-(2-(dimethylamino)pyrimidin-4-yl)-4-methylthiazol-2-yl)urea | 402.1 |
| 49 | 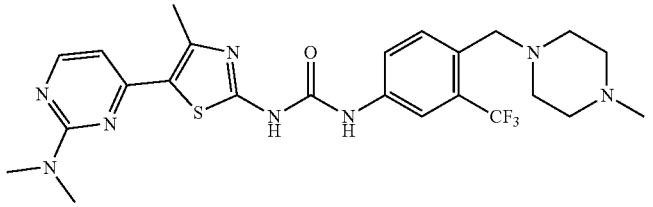 | 1-(5-(2-(Dimethylamino)pyrimidin-4-yl)-4-methylthiazol-2-yl)-3-(4-((4-methylpiperazin-1-yl)methyl)-3-(trifluoromethyl)phenyl)urea | 534.2 |
| 50 | 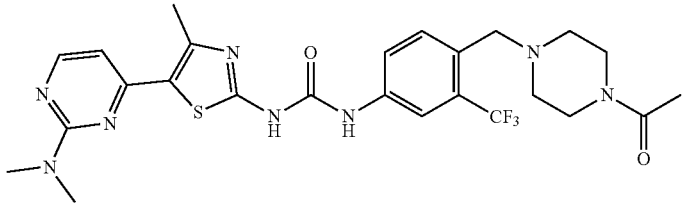 [SMILES: CC(=O)N1CCN(Cc2ccc(NC(=O)Nc3nc(C)c(-c4ccnc(N(C)C)n4)s3)cc2C(F)(F)F)CC1] | 1-(4-((4-Acetylpiperazin-1-yl)methyl)-3-(trifluoromethyl)-phenyl)-3-(5-(2-(dimethylamino)-pyrimidin-4-yl)-4-methylthiazol-2-yl)urea | 562.2 |
| 51 | 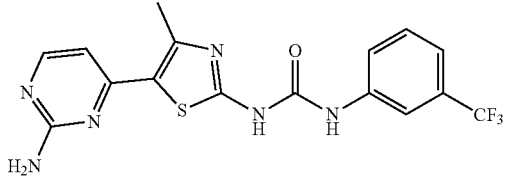 [SMILES: Cc1nc(NC(=O)Nc2cccc(C(F)(F)F)c2)sc1-c1ccnc(N)n1] | 1-(5-(2-Aminopyrimidin-4-yl)-4-methylthiazol-2-yl)-3-(3-(trifluoromethyl)phenyl)urea | 394.1 |
| 52 | 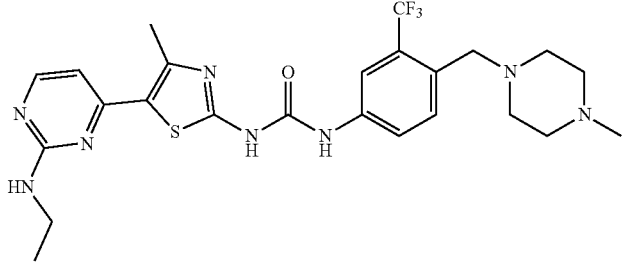 | 1-(5-(2-(Ethylamino)pyrimidin-4-yl)-4-methylthiazol-2-yl)-3-(4-((4-methylpiperazin-1-yl)methyl)-3-(trifluoromethyl)phenyl)urea | 534.2 |

TABLE 1-continued

Chemical structure of selected compounds of the present invention

| No. | Structure | Name | Mass |
|---|---|---|---|
| 53 | 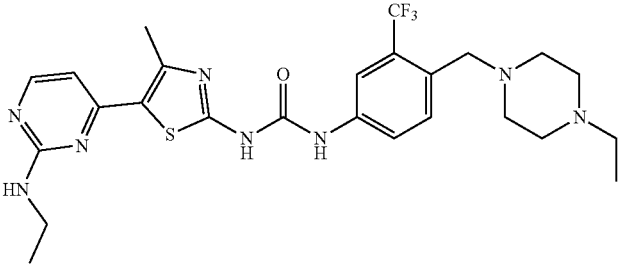 [SMILES: CCNc1nccc(-c2sc(NC(=O)Nc3ccc(CN4CCN(CC)CC4)c(C(F)(F)F)c3)nc2C)n1] | 1-(5-(2-(Ethylamino)pyrimidin-4-yl)-4-methylthiazol-2-yl)-3-(4-((4-ethylpiperazin-1-yl)methyl)-3-(trifluoromethyl)phenyl)urea | 548.2 |
| 54 | 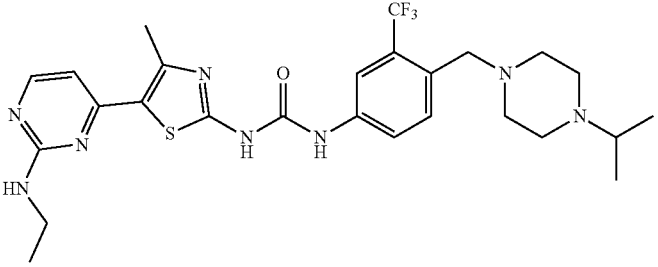 [SMILES: CCNc1nccc(-c2sc(NC(=O)Nc3ccc(CN4CCN(C(C)C)CC4)c(C(F)(F)F)c3)nc2C)n1] | 1-(5-(2-(ethylamino)pyrimidin-4-yl)-4-methylthiazol-2-yl)-3-(4-((4-isopropylpiperazin-1-yl)methyl)-3-(trifluoromethyl)phenyl)urea | 562.2 |
| 55 | 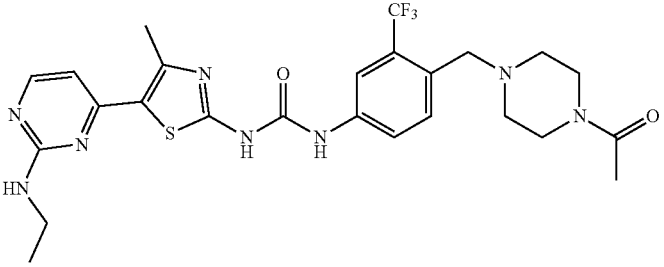 [SMILES: CCNc1nccc(-c2sc(NC(=O)Nc3ccc(CN4CCN(C(C)=O)CC4)c(C(F)(F)F)c3)nc2C)n1] | 1-(4-((4-Acetylpiperazin-1-yl)methyl)-3-(trifluoromethyl)-phenyl)-3-(5-(2-(ethylamino)-pyrimidin-4-yl)-4-methylthiazol-2-yl)urea | 562.2 |
| 56 | 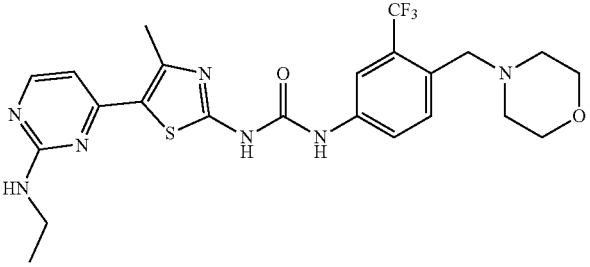 [SMILES: CCNc1nccc(-c2sc(NC(=O)Nc3ccc(CN4CCOCC4)c(C(F)(F)F)c3)nc2C)n1] | 1-(5-(2-(Ethylamino)pyrimidin-4-yl)-4-methylthiazol-2-yl)-3-(4-(morpholinomethyl)-3-(trifluoromethyl)phenyl)urea | 521.2 |
| 57 | 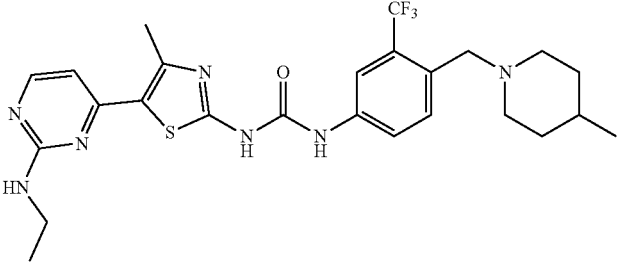 | 1-(5-(2-(Ethylamino)pyrimidin-4-yl)-4-methylthiazol-2-yl)-3-(4-((4-methylpiperidin-1-yl)methyl)-3-(trifluoromethyl)phenyl)urea | 533.2 |

TABLE 1-continued

Chemical structure of selected compounds of the present invention

| No. | Structure | Name | Mass |
|---|---|---|---|
| 58 | 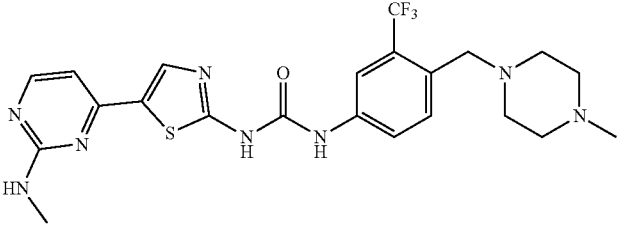 | 1-(5-(2-(Methylamino)pyrimidin-4-yl)thiazol-2-yl)-3-(4-((4-methylpiperazin-1-yl)methyl)-3-(trifluoromethyl)phenyl)urea | 506.2 |
| 59 | 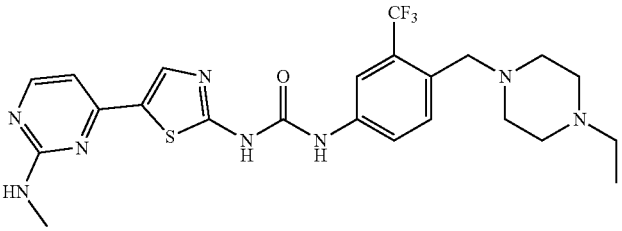 [SMILES: CCN1CCN(Cc2ccc(NC(=O)Nc3ncc(-c4ccnc(NC)n4)s3)cc2C(F)(F)F)CC1] | 1-(4-((4-Ethylpiperazin-1-yl)methyl)-3-(trifluoromethyl)phenyl)-3-(5-(2-(methylamino)pyrimidin-4-yl)thiazol-2-yl)urea | 520.2 |
| 60 | 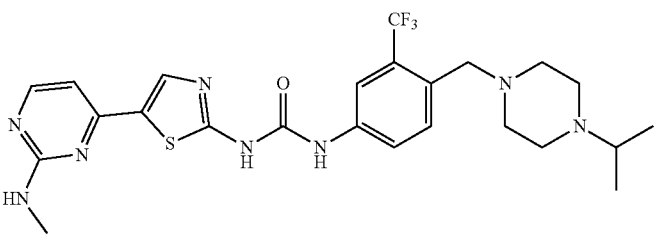 [SMILES: CNc1nccc(-c2cnc(NC(=O)Nc3ccc(CN4CCN(C(C)C)CC4)c(C(F)(F)F)c3)s2)n1] | 1-(4-((4-Isopropylpiperazin-1-yl)methyl)-3-(trifluoromethyl)phenyl)-3-(5-(2-(methylamino)pyrimidin-4-yl)thiazol-2-yl)urea | 535.2 |
| 61 | 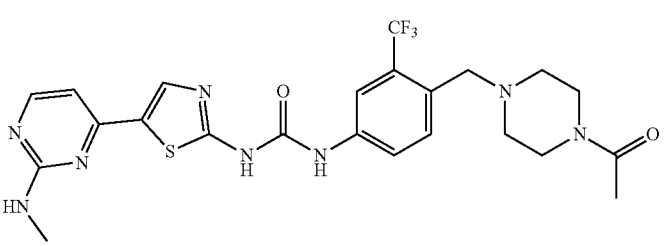 [SMILES: CNc1nccc(-c2cnc(NC(=O)Nc3ccc(CN4CCN(C(C)=O)CC4)c(C(F)(F)F)c3)s2)n1] | 1-(4-((4-Acetylpiperazin-1-yl)methyl)-3-(trifluoromethyl)phenyl)-3-(5-(2-(methylamino)pyrimidin-4-yl)thiazol-2-yl)urea | 535.2 |
| 62 | 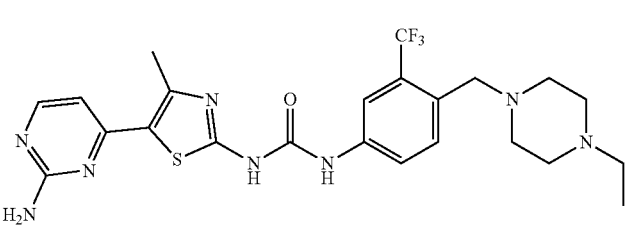 [SMILES: CCN1CCN(Cc2ccc(NC(=O)Nc3nc(C)c(-c4ccnc(N)n4)s3)cc2C(F)(F)F)CC1] | 1-(5-(2-Aminopyrimidin-4-yl)-4-methylthiazol-2-yl)-3-(4-((4-ethylpiperazin-1-yl)methyl)-3-(trifluoromethyl)phenyl)urea | 521.2 |
| 63 | 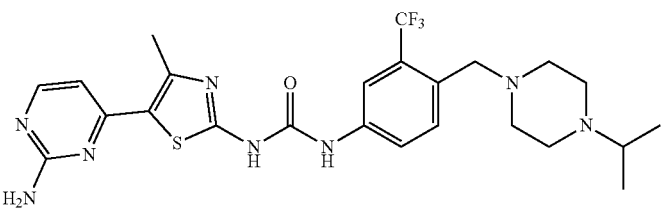 [SMILES: Cc1nc(NC(=O)Nc2ccc(CN3CCN(C(C)C)CC3)c(C(F)(F)F)c2)sc1-c1ccnc(N)n1] | 1-(5-(2-Aminopyrimidin-4-yl)-4-methylthiazol-2-yl)-3-(4-((4-isopropylpiperazin-1-yl)methyl)-3-(trifluoromethyl)phenyl)urea | 535.2 |

TABLE 1-continued

Chemical structure of selected compounds of the present invention

| No. | Structure | Name | Mass |
|---|---|---|---|
| 64 | 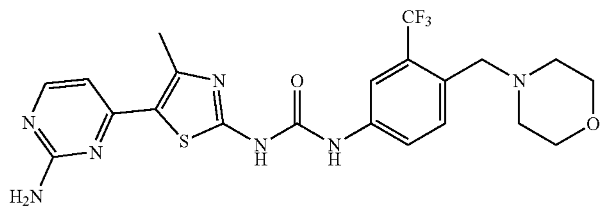 [SMILES: Cc1nc(NC(=O)Nc2ccc(CN3CCOCC3)c(C(F)(F)F)c2)sc1-c1ccnc(N)n1] | 1-(5-(2-Aminopyrimidin-4-yl)-4-methylthiazol-2-yl)-3-(4-(morpholinomethyl)-3-(trifluoromethyl)phenyl)urea | 494.2 |
| 65 | 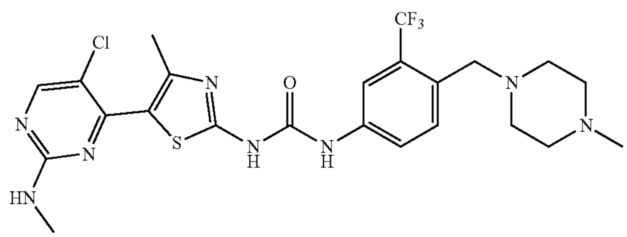 [SMILES: CNc1ncc(Cl)c(-c2sc(NC(=O)Nc3ccc(CN4CCN(C)CC4)c(C(F)(F)F)c3)nc2C)n1] | 1-(5-(5-Chloro-2-(methylamino)pyrimidin-4-yl)-4-methylthiazol-2-yl)-3-(4-((4-methylpiperazin-1-yl)methyl)-3-(trifluoromethyl)phenyl)urea | 555.2 |
| 66 | 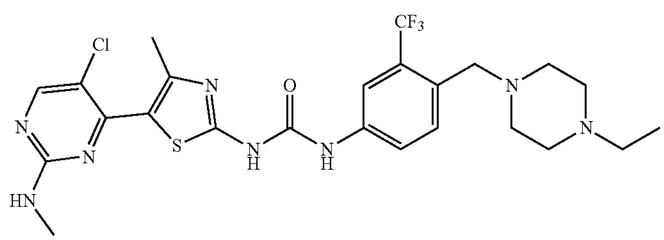 [SMILES: CCN1CCN(Cc2ccc(NC(=O)Nc3nc(C)c(-c4nc(NC)ncc4Cl)s3)cc2C(F)(F)F)CC1] | 1-(5-(5-Chloro-2-(methylamino)pyrimidin-4-yl)-4-methylthiazol-2-yl)-3-(4-((4-ethylpiperazin-1-yl)methyl)-3-(trifluoromethyl)phenyl)urea | 569.2 |
| 67 | 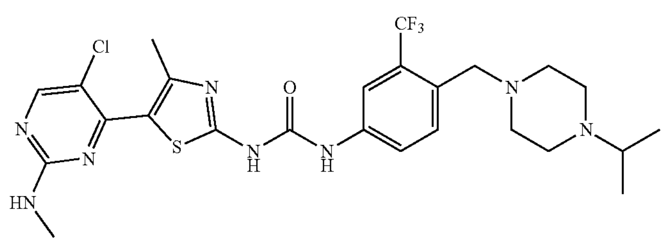 [SMILES: CNc1ncc(Cl)c(-c2sc(NC(=O)Nc3ccc(CN4CCN(C(C)C)CC4)c(C(F)(F)F)c3)nc2C)n1] | 1-(5-(5-Chloro-2-(methylamino)pyrimidin-4-yl)-4-methylthiazol-2-yl)-3-(4-((4-isopropylpiperazin-1-yl)methyl)-3-(trifluoromethyl)phenyl)urea | 583.2 |
| 68 | 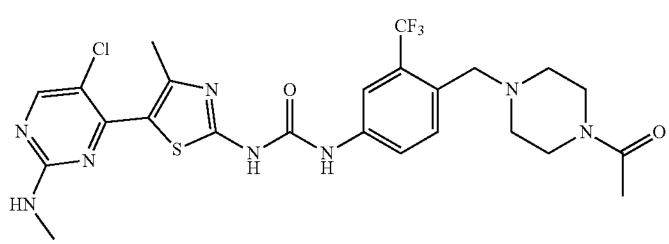 [SMILES: CNc1ncc(Cl)c(-c2sc(NC(=O)Nc3ccc(CN4CCN(C(C)=O)CC4)c(C(F)(F)F)c3)nc2C)n1] | 1-(4-((4-Acetylpiperazin-1-yl)methyl)-3-(trifluoromethyl)phenyl)-3-(5-(5-chloro-2-(methylamino)pyrimidin-4-yl)-4-methylthiazol-2-yl)urea | 583.2 |
| 69 | 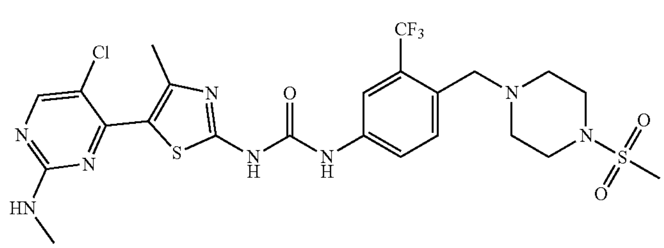 [SMILES: CNc1ncc(Cl)c(-c2sc(NC(=O)Nc3ccc(CN4CCN(S(C)(=O)=O)CC4)c(C(F)(F)F)c3)nc2C)n1] | 1-(5-(5-Chloro-2-(methylamino)pyrimidin-4-yl)-4-methylthiazol-2-yl)-3-(4-((4-(methylsulfonyl)piperazin-1-yl)methyl)-3-(trifluoromethyl)phenyl)urea | 619.1 |

TABLE 1-continued

Chemical structure of selected compounds of the present invention

| No. | Structure | Name | Mass |
|---|---|---|---|
| 70 | 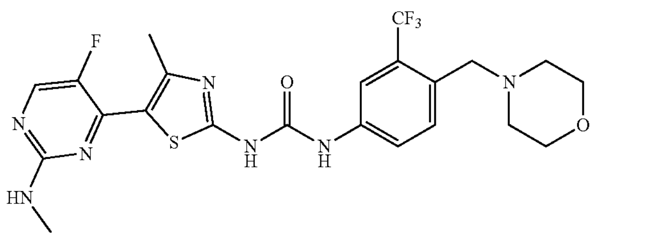 [SMILES: CNc1ncc(F)c(-c2sc(NC(=O)Nc3ccc(CN4CCOCC4)c(C(F)(F)F)c3)nc2C)n1] | 1-(5-(5-Fluoro-2-(methylamino)pyrimidin-4-yl)-4-methylthiazol-2-yl)-3-(4-(morpholinomethyl)-3-(trifluoromethyl)phenyl)urea | 526.2 |
| 71 | 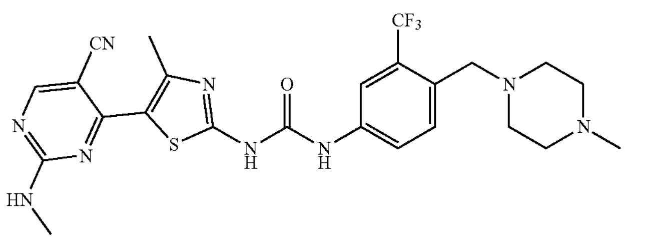 [SMILES: CNc1ncc(C#N)c(-c2sc(NC(=O)Nc3ccc(CN4CCN(C)CC4)c(C(F)(F)F)c3)nc2C)n1] | 1-(5-(5-Cyano-2-(methylamino)pyrimidin-4-yl)-4-methylthiazol-2-yl)-3-(4-((4-methylpiperazin-1-yl)methyl)-3-(trifluoromethyl)phenyl)urea | 546.2 |
| 72 | 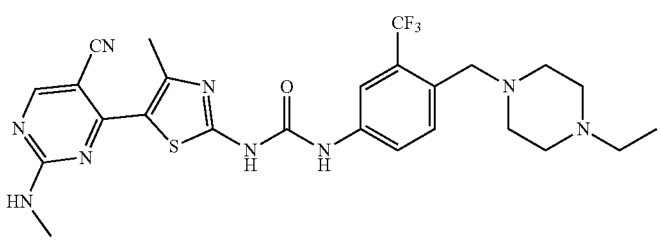 [SMILES: CCN1CCN(Cc2ccc(NC(=O)Nc3nc(C)c(-c4nc(NC)ncc4C#N)s3)cc2C(F)(F)F)CC1] | 1-(5-(5-Cyano-2-(methylamino)pyrimidin-4-yl)-4-methylthiazol-2-yl)-3-(4-((4-ethylpiperazin-1-yl)methyl)-3-(trifluoromethyl)phenyl)urea | 560.2 |
| 73 | 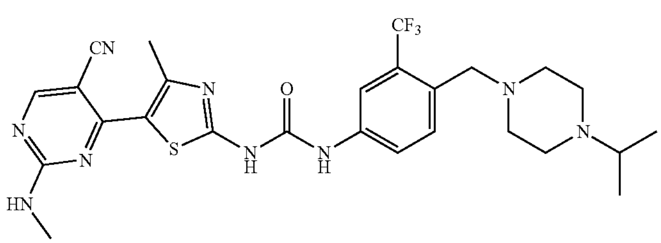 [SMILES: CNc1ncc(C#N)c(-c2sc(NC(=O)Nc3ccc(CN4CCN(C(C)C)CC4)c(C(F)(F)F)c3)nc2C)n1] | 1-(5-(5-Cyano-2-(methylamino)pyrimidin-4-yl)-4-methylthiazol-2-yl)-3-(4-((4-isopropylpiperazin-1-yl)methyl)-3-(trifluoromethyl)phenyl)urea | 574.2 |
| 74 | 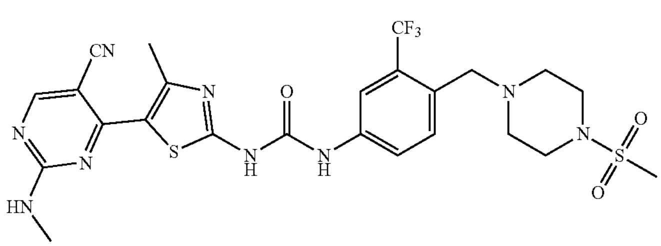 [SMILES: CNc1ncc(C#N)c(-c2sc(NC(=O)Nc3ccc(CN4CCN(S(C)(=O)=O)CC4)c(C(F)(F)F)c3)nc2C)n1] | 1-(5-(5-Cyano-2-(methylamino)pyrimidin-4-yl)-4-methylthiazol-2-yl)-3-(4-((4-(methylsulfonyl)piperazin-1-yl)methyl)-3-(trifluoromethyl)phenyl)urea | 610.2 |
| 75 | 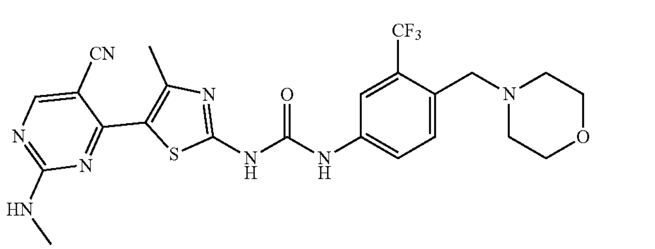 [SMILES: CNc1ncc(C#N)c(-c2sc(NC(=O)Nc3ccc(CN4CCOCC4)c(C(F)(F)F)c3)nc2C)n1] | 1-(5-(5-Cyano-2-(methylamino)pyrimidin-4-yl)-4-methylthiazol-2-yl)-3-(4-(morpholinomethyl)-3-(trifluoromethyl)phenyl)urea | 533.2 |

TABLE 1-continued

Chemical structure of selected compounds of the present invention

| No. | Structure | Name | Mass |
|---|---|---|---|
| 76 | 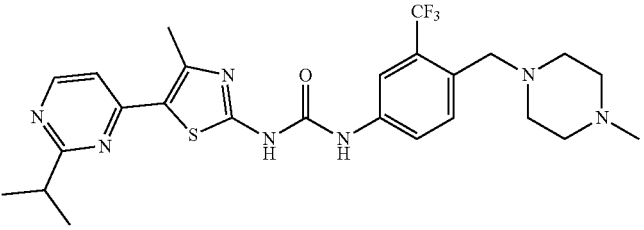 [SMILES: Cc1nc(NC(=O)Nc2ccc(CN3CCN(C)CC3)c(C(F)(F)F)c2)sc1-c1ccnc(C(C)C)n1] | 1-(5-(2-Isopropylpyrimidin-4-yl)-4-methylthiazol-2-yl)-3-(4-((4-methylpiperazin-1-yl)methyl)-3-(trifluoromethyl)phenyl)urea | 534.2 |
| 77 | 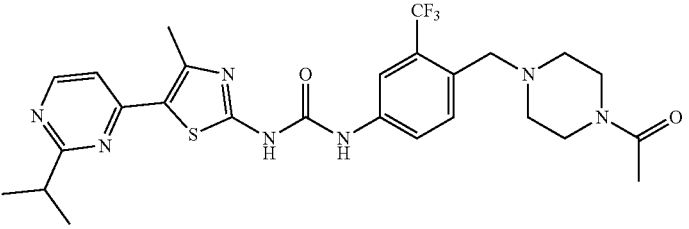 [SMILES: CC(=O)N1CCN(Cc2ccc(NC(=O)Nc3nc(C)c(-c4ccnc(C(C)C)n4)s3)cc2C(F)(F)F)CC1] | 1-(4-((4-Acetylpiperazin-1-yl)methyl)-3-(trifluoromethyl)phenyl)-3-(5-(2-isopropylpyrimidin-4-yl)-4-methylthiazol-2-yl)urea | 562.2 |
| 78 | 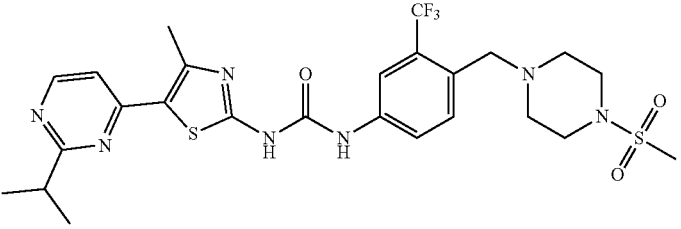 [SMILES: Cc1nc(NC(=O)Nc2ccc(CN3CCN(S(C)(=O)=O)CC3)c(C(F)(F)F)c2)sc1-c1ccnc(C(C)C)n1] | 1-(5-(2-Isopropylpyrimidin-4-yl)-4-methylthiazol-2-yl)-3-(4-((4-(methylsulfonyl)-piperazin-1-yl)methyl)-3-(trifluoromethyl)phenyl)urea | 598.2 |
| 77 79 | 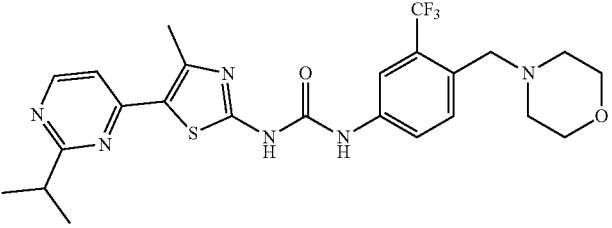 [SMILES: Cc1nc(NC(=O)Nc2ccc(CN3CCOCC3)c(C(F)(F)F)c2)sc1-c1ccnc(C(C)C)n1] | 1-(5-(2-Isopropylpyrimidin-4-yl)-4-methylthiazol-2-yl)-3-(4-(morpholinomethyl)-3-(trifluoromethyl)phenyl)urea | 521.2 |
| 80 | 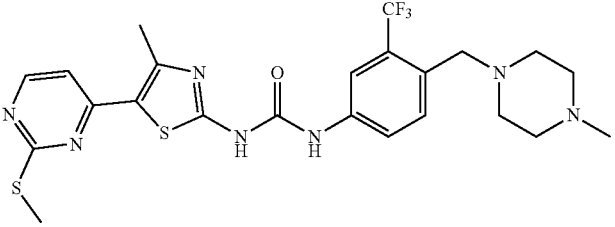 [SMILES: CSc1nccc(-c2sc(NC(=O)Nc3ccc(CN4CCN(C)CC4)c(C(F)(F)F)c3)nc2C)n1] | 1-(4-Methyl-5-(2-(methylthio)pyrimidin-4-yl)thiazol-2-yl)-3-(4-((4-methyl-piperazin-1-yl)methyl)-3-(trifluoromethyl)phenyl)urea | 538.2 |
| 81 | 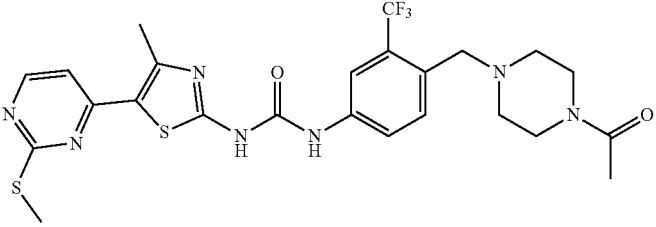 [SMILES: CSc1nccc(-c2sc(NC(=O)Nc3ccc(CN4CCN(C(C)=O)CC4)c(C(F)(F)F)c3)nc2C)n1] | 1-(4-((4-Acetylpiperazin-1-yl)methyl)-3-(trifluoromethyl)phenyl)-3-(4-methyl-5-(2-(methylthio)pyrimidin-4-yl)thiazol-2-yl)urea | 566.2 |

TABLE 1-continued

Chemical structure of selected compounds of the present invention

| No. | Structure | Name | Mass |
|---|---|---|---|
| 82 | 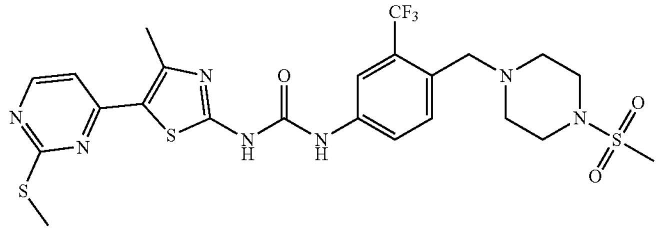 [SMILES: CSc1nccc(-c2sc(NC(=O)Nc3ccc(CN4CCN(S(C)(=O)=O)CC4)c(C(F)(F)F)c3)nc2C)n1] | 1-(4-Methyl-5-(2-(methylthio)pyrimidin-4-yl)thiazol-2-yl)-3-(4-((4-(methylsulfonyl)piperazin-1-yl)methyl)-3-(trifluoromethyl)phenyl)urea | 602.1 |
| 83 | 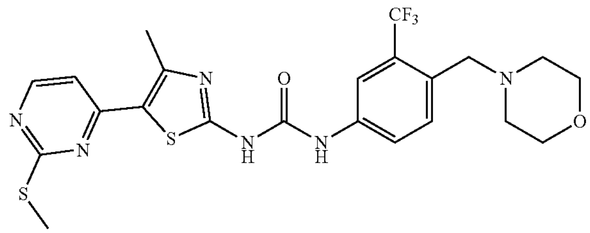 [SMILES: CSc1nccc(-c2sc(NC(=O)Nc3ccc(CN4CCOCC4)c(C(F)(F)F)c3)nc2C)n1] | 1-(4-Methyl-5-(2-(methylthio)pyrimidin-4-yl)thiazol-2-yl)-3-(4-(morpholinomethyl)-3-(trifluoromethyl)phenyl)urea | 525.1 |

Compounds (and pharmaceutically acceptable salts, solvates and prodrugs thereof) may be administered in combination with one or more additional agent(s) for the treatment of cancer or another proliferative disease or condition. For example, the compounds may be used in combination with other anti-cancer agents in order to inhibit more than one cancer signalling pathway simultaneously so as to make cancer cells more susceptible to anti-cancer therapies (eg treatments with other anti-cancer agents, chemotherapy, radiotherapy or a combination thereof). As such, the compounds of formula I may be used in combination with one or more of the following categories of anti-cancer agents:

other anti-proliferative/antineoplastic drugs and combinations thereof, as used in medical oncology, such as alkylating agents (eg cis-platin, oxaliplatin, carboplatin, cyclophosphamide, nitrogen mustard, melphalan, chlorambucil, busulphan, temozolamide and nitrosoureas); antimetabolites (eg gemcitabine and antifolates such as fluoropyrimidines like 5-fluorouracil and tegafur, raltitrexed, methotrexate, cytosine arabinoside, fludarabine and hydroxyurea); antitumour antibiotics (eg anthracyclines such as adriamycin, bleomycin, doxorubicin, daunomycin, epirubicin, idarubicin, mitomycin-C, dactinomycin and mithramycin); antimitotic agents (eg vinca alkaloids such as vincristine, vinblastine, vindesine and vinorelbine and taxoids including taxol and taxotere and polokinase inhibitors); and topoisomerase inhibitors (eg epipodophyllotoxins such as etoposide and teniposide, amsacrine, topotecan and camptothecin);

cytostatic agents such as antioestrogens (eg tamoxifen, fulvestrant, toremifene, raloxifene, droloxifene and iodoxyfene), antiandrogens (eg bicalutamide, flutamide, nilutamide and cyproterone acetate), LHRH antagonists or LHRH agonists (eg goserelin, leuprorelin and buserelin), progestogens (eg megestrol acetate), aromatase inhibitors (eg as anastrozole, letrozole, vorazole and exemestane) and inhibitors of 5α-reductase such as finasteride;

anti-invasion agents (eg c-Src kinase family inhibitors such as 4-(6-chloro-2,3-methylenedioxyanilino)-7-[2-(4-methylpiperazin-1-yl)ethoxy]-5-tetrahydropyran-4-yloxyquinazoline (AZD0530; International Patent Publication No WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib) and bosutinib (SKI-606)), and metalloproteinase inhibitors including marimastat, inhibitors of urokinase plasminogen activator receptor function or antibodies to heparanase;

inhibitors of growth factor function (eg growth factor antibodies and growth factor receptor antibodies such as the anti-erbB2 antibody trastuzumab (Herceptin™), the anti-EGFR antibody panitumumab, the anti-erbB1 antibody cetuximab (Erbitux, C225) and any growth factor or growth factor receptor antibodies disclosed by Stern et al. Critical reviews in oncology/haematology, 2005, Vol. 54, pp 11-29). Such inhibitors also include tyrosine kinase inhibitors such as inhibitors of the epidermal growth factor family (eg EGFR family tyrosine kinase inhibitors such as N-(3-chloro-4-fluorophenyl)-7-methoxy-6-(3-morpholinopropoxy) quinazolin-4-amine (gefitinib, ZD1839), N-(3-ethynylphenyl)-6,7-bis(2-methoxyethoxy) quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107); inhibitors of serine/threonine kinases (eg Ras/Raf signalling inhibitors such as farnesyl transferase inhibitors including sorafenib (BAY 43-9006), tipifarnib (R115777) and lonafarnib (SCH66336)), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor (insulin-like growth factor) kinase inhibitors; aurora kinase inhibitors (eg AZD1152, PH739358, VX-680, MLN8054, R763, MP235, MP529, VX-528 and AX39459) and cyclin dependent kinase inhibitors such as CDK2 and/or CDK9 inhibitors;

anti-angiogenic agents such as those which inhibit the effects of vascular endothelial growth factor (eg the anti-vascular endothelial cell growth factor antibody bevacizumab (Avastin™) and VEGF receptor tyrosine kinase inhibitors such as vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy)quinazoline (AZD2171; Example 240 within International Patent Publication No WO 00/47212), compounds such as those disclosed in International Patent Publication Nos WO97/22596, WO 97/30035, WO 97/32856 and WO 98/13354, and compounds that work by other mechanisms (eg linomide, inhibitors of integrin αvβ3 function and angiostatin);

vascular damaging agents such as Combretastatin A4 and compounds disclosed in International Patent Publication Nos WO 99/02166, WO 00/40529, WO 00/41669, WO 01/92224, WO 02/04434 and WO 02/08213;

an endothelin receptor antagonist such as zibotentan (ZD4054) or atrasentan;

antisense therapies such as those which are directed to the targets listed above, such as ISIS 2503, an anti-ras antisense;

gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and immunotherapy approaches, including for example ex vivo and in vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

Where used in combination with other anti-cancer agents, a compound of the present invention and the other anti-cancer agent can be administered in the same pharmaceutical composition or in separate pharmaceutical compositions. If administered in separate pharmaceutical compositions, the compound and the other anti-cancer agent may be administered simultaneously or sequentially in any order (eg within seconds or minutes or even hours (eg 2 to 48 hours)).

The present invention is typically applied to the treatment of cancer or another proliferative cell disease or condition in a human subject. However, the subject may also be selected from, for example, livestock animals (eg cows, horses, pigs, sheep and goats), companion animals (eg dogs and cats) and exotic animals (eg non-human primates, tigers, elephants etc).

Cancers and other proliferative cell diseases and conditions that may be treated in accordance with the present invention include colorectal cancer, biliary tract cancer, brain cancer (including glioblastomas and medulloblastomas), breast cancer, cervical cancer; choriocarcinoma, endometrial cancer, oesophageal cancer, gastric cancer, haematological neoplasms (including acute lymphocytic leukemia (ALL)), chronic lymphocytic leukemia (CLL) and chronic myelogenous leukemia (CML), acute myeloid leukaemia (AML), multiple myeloma, AIDS-associated leukemias and adult T-cell leukemia lymphoma, intraepithelial neoplasms (including Bowen's disease and Paget's disease), liver cancer, lung cancer, lymphomas (including Hodgkin's disease and lymphocytic lymphomas), neuroblastomas, oral cancer (including squamous cell carcinoma), ovarian cancer (including those arising from epithelial cells, stromal cells, germ cells, and mesenchymal cells), pancreatic cancer, prostate cancer, colorectal cancer, sarcomas (including leiomyosarcoma, rhabdomyosarcoma, liposarcoma, fibrosarcoma, and osteosarcoma), skin cancer (including melanoma, Kaposi's sarcoma, basocellular cancer, and squamous cell cancer), testicular cancer (including germinal tumours such as seminoma, non-seminoma teratomas, and choriocarcinomas), stromal tumours, germ cell tumours, thyroid cancer (including thyroid adenocarcinoma and medullar carcinoma), and renal cancer (including adenocarcinoma and Wilms' tumour).

In some embodiments, the compounds of the present invention are used to treat cancers characterised by over-expression of CDKs (particularly the over-expression of CDK8), for example, colorectal cancer, chronic lymphocytic leukaemia (CLL), lymphoma, leukaemia, breast cancer, lung cancer, prostate cancer, melanoma, pancreatic cancer, ovarian cancer, squamous cancer, carcinoma of head and neck, endometrial cancer, and oesophageal carcinoma (reviewed in Lapenna et al., *Nat Rev Drug Discov* 8(7):547-66 (2009) and Asghar et al., *Nat Rev Drug Discov* 14(2):130-46 (2015)). CDKs and/or cyclin over-expression may be determined by, for example, assessing the amount of mRNA encoding CDK and/or cyclin in a suitable sample using any of the techniques well known to those skilled in the art (eg quantitative amplification techniques such as qPCR).

The compounds of the present invention may be formulated into a pharmaceutical composition with a pharmaceutically acceptable carrier, diluent and/or excipient. Examples of suitable carriers and diluents are well known to those skilled in the art, and are described in, for example, Remington's Pharmaceutical Sciences, Mack Publishing Co., Easton, Pa. 1995. Examples of suitable excipients for the various different forms of pharmaceutical compositions described herein may be found in the Handbook of Pharmaceutical Excipients, $2^{nd}$ Edition, (1994), Edited by A Wade and P J Weller. Examples of suitable carriers include lactose, starch, glucose, methyl cellulose, magnesium stearate, mannitol, sorbitol and the like. Examples of suitable diluents include ethanol, glycerol and water. The choice of carrier, diluent and/or excipient may be made with regard to the intended route of administration and standard pharmaceutical practice.

A pharmaceutical composition comprising a compound of the present invention may further comprise any suitable binders, lubricants, suspending agents, coating agents and solubilising agents. Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol. Examples of suitable lubricants include sodium oleate, sodium stearate, magnesium stearate, sodium benzoate, sodium acetate, sodium chloride and the like. Preservatives, stabilising agents, dyes and even flavouring agents may be provided in the pharmaceutical composition. Examples of preservatives include sodium benzoate, sorbic acid and esters of p-hydroxybenzoic acid. Anti-oxidants and suspending agents may be also used.

A pharmaceutical composition comprising a compound of the present invention may be adapted for oral, rectal, vaginal, parenteral, intramuscular, intraperitoneal, intraarterial, intrathecal, intrabronchial, subcutaneous, intradermal, intravenous, nasal, buccal or sublingual routes of administration. For oral administration, particular use may be made of compressed tablets, pills, tablets, gellules, drops, and capsules. For other forms of administration, a pharmaceutical composition may comprise solutions or emulsions which may be injected intravenously, intraarterially, intrathecally, subcutaneously, intradermally, intraperitoneally or intramuscularly, and which are prepared from sterile or sterilisable solutions. A pharmaceutical composition comprising a compound of the present invention may also be in form of suppositories, pessaries, suspensions, emulsions, lotions, ointments, creams, gels, sprays, solutions or dusting powders. A pharmaceutical composition may be formulated in unit dosage form (ie in the form of discrete portions containing a unit dose, or a multiple or sub-unit of a unit dose).

The compounds of the present invention may be provided as a pharmaceutically acceptable salt including, for example, suitable acid addition or base salts thereof. A review of suitable pharmaceutical salts may be found in Berge et al., *J Pharm Sci* 66:1-19 (1977). Salts are formed, for example with strong inorganic acids such as mineral acids (eg sulfuric acid, phosphoric acid or hydrohalic acids), with strong organic carboxylic acids, such as alkanecarboxylic acids of 1 to 4 carbon atoms which are unsubstituted or substituted (eg by halogen), such as acetic acid, with saturated or unsaturated dicarboxylic acids (eg oxalic, malonic, succinic, maleic, fumaric, phthalic or tetraphthalic acid), with hydroxycarboxylic acids (eg ascorbic, glycolic, lactic, malic, tartaric or citric acid), with amino acids (eg aspartic or glutamic acid), with benzoic acid, or with organic sulfonic acids (eg ($C_1$-$C_4$-alkyl- or aryl-sulfonic acids which are unsubstituted or substituted by, for example, halogen) such as methane- or p-toluene sulfonic acid).

The compounds of the present invention may be provided in their various crystalline forms, polymorphic forms and (an)hydrous forms. In this regard, it is well known to those skilled in the art that chemical compounds may be isolated in any of such forms by slightly varying the method of purification and or isolation from the solvents used in the synthetic preparation of such compounds.

The present invention further provides a method of synthesising a compound according to the present invention, or a pharmaceutically acceptable salt, solvate or prodrug thereof.

In some embodiments, a compound according to the present invention is synthesised by, for example, the following Scheme 1; involving reaction between pyrimidine precursors (F) and isocyanatobenzenes (G) which can be obtained from suitable aniline and triphosgene in the presence of bases, e.g. triethylamine, potassium hydroxide, sodium carbonate, and cesium carbonate. The pyrimidine precursors (F) can be prepared by reacting acrylates (B) or (D) with suitable amidines or guanidines by a number of methods well known to those skilled in the art. Alternatively, (F) can be obtained from suitable pyrimidine precursors directly, e.g. from 2,4-disubstituted (halogen, amine, etc.) pyrimidines by successive substitution reactions. Acrylates (B) or (D) which may be particularly suitable for the purpose of synthesising compounds according to the present invention, may be obtained from heterocyclic ketones (A) and (C) by condensation with the respective acetaldehydes and N,N-dimethylformamide dimethyl acetal.

Scheme 1

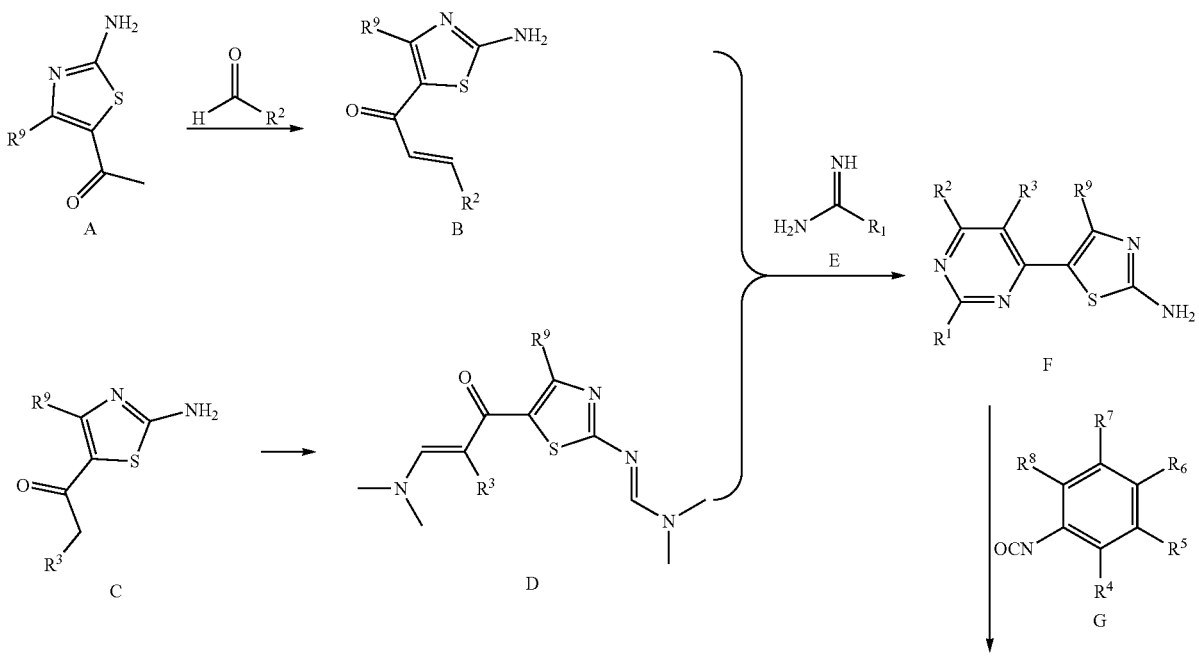

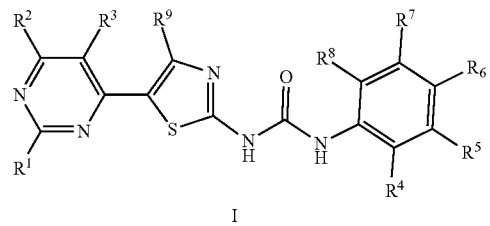

The present invention is hereinafter further described by way of the following, non-limiting examples:

EXAMPLES

Example 1 Synthesis $^1$H spectra were recorded at 298 K on a Bruker AVANCE III HD 500 spectrometer and were analysed using Bruker Topspin 3.2 software. 1H NMR signals are reported with chemical shift values δ (ppm), multiplicity (s=singlet, d=doublet, t=triplet, q=quartet, dd=doublet of doublets, m=multiplet and br=broad), relative integral, coupling constants J (Hz) and assignments. High resolution mass spectra were recorded on an AB SCIEX TripleTOF 5600 mass spectrometer (Concord, ON, Canada), and ionisation of all samples was carried out using ESI.

General synthetic procedure. To a solution of triphosgene (0.4 equiv) in dry DCM at 0° C. under $N_2$ was added dropwise a solution of aniline (1.0 equiv) and triethylamine (1.0 equiv) in DCM. The reaction mixture was stirred for 1 h at room temperature. A solution of an appropriate thiazole-2-amine (1.0 equiv) and triethylamine (1.0 equiv) in DMSO was then added and the reaction mixture was stirred overnight. Water was added to the mixture, and the residue was purified by Biotage® FlashMaster Personal$^+$ chromatography (silica gel), and crystallised if necessary, to give the desired compounds.

1-(4-methyl-5-(2-(methylamino)pyrimidin-4-yl)thiazol-2-yl)-3-phenylurea (1) Prepared by treating 4-methyl-5-(2-(methylamino)pyrimidin-4-yl)thiazol-2-amine (100 mg, 452 μmol) and aniline (42.0 mg, 452 μmol) according to the general synthetic procedure to produce a white solid (77.0 mg, 54%). $^1$H NMR (DMSO-d6) δ (2.55 (s, 3H), 2.82 (d, 3H, J 4.5), 6.76 (d, 1H, J 4.5), 7.03-7.07 (m, 2H), 7.32 (t, 2H, J 8.0), 7.49 (d, 2H), 8.25 (app s, 1H), 9.01 (br s, 1H), 10.60 (br s, 1H). HRMS m 341.1179.

1-(4-methyl-5-(2-(methylamino)pyrimidin-4-yl)thiazol-2-yl)-3-(2-(trifluoromethyl)phenyl)urea (2) Prepared by treating 4-methyl-5-(2-(methylamino)pyrimidin-4-yl)thiazol-2-amine (100 mg, 452 μmol) and 2-(trifluoromethyl)aniline (72 mg, 452 μmol) according to the general synthetic procedure to produce a white solid (63.0 mg, 34%). H NMR (DMSO-d6) δ 2.56 (s, 3H), 2.81 (d, 3H, J 3.0), 6.77 (s, 1H,), 7.06 (s, 1H), 7.36 (t, 1H, J 8.0), 7.67-7.74 (m, 2H), 7.98 (d, 1H, J 8.5), 8.26 (s, 1H), 8.73 (br s, 1H), 11.30 (br s, 1H). HRMS m/z 409.1060.

1-(2-fluorophenyl)-3-(4-methyl-5-(2-(methylamino)pyrimidin-4-yl)thiazol-2-yl)urea (3) Prepared by treating 4-methyl-5-(2-(methylamino)pyrimidin-4-yl)thiazol-2-amine (100 mg, 452 μmol) and 2-fluoroaniline (83.0 mg, 452 mol) according to the general synthetic procedure to produce a white solid (105 mg, 65%). $^1$H NMR (DMSO-d6) δ 2.55 (s, 3H), 2.82 (s, 3H, J 4.5), 6.77 (d, 1H, J 4.5), 7.07 (app d, 1H, J 4.5), 7.08-7.7.11 (m, 1H), 7.19 (t, 1H, J 8.0), 7.26-7.30 (m, 1H), 8.13 (t, 1H, J 8.0), 8.26 (app s, 1H), 9.02 (br s, 1H), 10.86 (br s, 11). HRMS m/z 359.1091.

1-(2-methoxyphenyl)-3-(4-methyl-5-(2-(methylamino)pyrimidin-4-yl)thiazol-2-yl)urea (4) Prepared by treating 4-methyl-5-(2-(methylamino)pyrimidin-4-yl)thiazol-2-amine (100 mg, 452 μmol) and 2-methoxyaniline (55.0 mg, 452 μmol) according to the general synthetic procedure to produce a white solid (90.0 mg, 54%). $^1$H NMR (DMSO-d6) δ 2.56 (s, 3H), 2.82 (s, 3H, J 4.5), 3.88 (s, 3H), 6.76 (d, 1H, J 4.5), 6.93 (t, 1H, J 8.0), 7.01-7.06 (m, 2H), 8.11 (d, 2H, J 8.0), 8.25 (app s, 11), 8.84 (br s, 1H), 11.13 (br s, 1H). HRMS m/z 371.1279.

1-(3-chloro-4-(trifluoromethyl)phenyl)-3-(4-methyl-5-(2-(methylamino)pyrimidin-4-yl)thiazol-2-yl)urea (5) Prepared by reacting 4-methyl-5-(2-(methylamino)pyrimidin-4-yl)thiazol-2-amine (100 mg, 452 μmol) and 3-chloro-4-(trifluoromethyl)aniline (88.0 mg, 452 μmol) according to the general synthetic procedure to produce a white solid (70.0 mg, 35%). $^1$H NMR (DMSO-d6) δ 2.56 (s, 3H), 2.83 (d, 3H, J 4.5), 6.64 (app d, 1H, J 4.5), 7.09 (app d, 1H, J 4.5) 7.62 (d, 1H, J 8.0), 7.76 (d, 1H, J 9.0), 7.98 (s, 1H), 8.26 (s, 1H), 9.62 (brs, 1H), 11.03 (brs, 1H). HRMS m/z 443.0668.

1-(4-fluoro-2-methylphenyl)-3-(4-methyl-5-(2-(methylamino)pyrimidin-4-yl)thiazol-2-yl)urea (6) Prepared by reacting 4-methyl-5-(2-(methylamino)pyrimidin-4-yl)thiazol-2-amine (100 mg, 452 μmol) and 4-fluoro-2-methylaniline (56.0 mg, 452 μmol) according to the general synthetic procedure to produce a white solid (93.0 mg, 56%). $^1$H NMR (DMSO-d6) δ 2.25 (s, 3H), 2.55 (s, 3H), 2.81 (d, 3H, J 4.5), 6.75 (d, 1H, J 4.0), 6.70-7.05 (m, 2H), 7.10 (dd, 1H, J 9.5 & 3.0), 7.78 (dd, 1H, J 8.5 & 5.5), 8.25 (s, 1H), 8.44 (brs, 1H), 10.94 (brs, 1H). HRMS m/z 373.1246.

1-(4-fluoro-2-(trifluoromethyl)phenyl)-3-(4-methyl-5-(2-(methylamino)pyrimidin-4-yl)thiazol-2-yl)urea (7) Prepared by reacting 4-methyl-5-(2-(methylamino)pyrimidin-4-yl)thiazol-2-amine (100 mg, 452 μmol) and 4-fluoro-2-(trifluoromethyl)aniline (81 mg, 452 μmol) according to the general synthetic procedure to produce a white solid (68.0 mg, 35%). $^1$H NMR (DMSO-d6) δ 2.55 (s, 3H), 2.81 (d, 3H, J 4.5), 6.76 (app s, 1H), 7.06 (app d, 1H, J 3.0), 7.37 (d, 1H, J 7.5), 7.54 (t, 1H, J 8.0), 7.68 (d, 1H, J 7.5), 8.04 (s, 1H), 8.25 (s, 1H), 9.38 (brs, 1H), 11.21 (brs, 1H). HRMS m/z 427.0958.

1-(2,4-bis(trifluoromethyl)phenyl)-3-(4-methyl-5-(2-(methylamino)pyrimidin-4-yl)thiazol-2-yl)urea (8) Prepared by reacting 4-methyl-5-(2-(methylamino)pyrimidin-4-yl)thiazol-2-amine (100 mg, 452 μmol) and 2,4-bis(trifluoromethyl)aniline (103 mg, 452 μmol) according to the general synthetic procedure to produce a white solid (120 mg, 56%). $^1$H NMR (DMSO-d6) δ 2.56 (s, 3H), 2.82 (d, 3H, J 4.0), 6.78 (app s, 1H), 7.08 (s, 1H), 8.00 (s, 1H), 8.07 (d, 1H, J 8.0), 8.26 (app s, 1H), 8.40 (d, 1H, J 8.0), 8.90 (br s, 1H), 11.56 (br s, 1H). HRMS m/z 477.0930.

1-(2,5-bis(trifluoromethyl)phenyl)-3-(4-methyl-5-(2-(methylamino)pyrimidin-4-yl)thiazol-2-yl)urea (9) Prepared by treating 4-methyl-5-(2-(methylamino)pyrimidin-4-yl)thiazol-2-amine (100 mg, 452 µmol) and 2,5-bis(trifluoromethyl)aniline (103 mg, 452 µmol) according to the general synthetic procedure to produce a white solid (77.0 mg, 36%). $^1$H NMR (DMSO-d6) δ 2.56 (s, 3H), 2.82 (s, 3H, J 4.0), 6.78 (s, 1H), 7.08 (s, 1H), 7.70 (d, 1H, J 8.0), 7.80 (d, 1H, J 8.0), 8.26 (s, 1H), 8.48 (s, 1H), 8.95 (brs, 1H), 11.49 (brs, 1H). HRMS m/z 477.0925.

1-(4-methyl-5-(2-(methylamino)pyrimidin-4-yl)thiazol-2-yl)-3-(3-(trifluoromethyl)phenyl)urea (10) Prepared by treating 4-methyl-5-(2-(methylamino)pyrimidin-4-yl)thiazol-2-amine (100 mg, 452 µmol) and 3-(trifluoromethyl)aniline (72 mg, 452 µmol) according to the general synthetic procedure to produce a white solid (43.0 mg, 23%). $^1$H NMR (DMSO-d6) δ 2.55 (s, 3H), 2.83 (d, 3H, J 3.5), 6.76 (d, 1H, J 3.0), 7.06 (d, 1H, J 3.0), 7.59 (t, 1H, J 6.5) 7.65 (d, 1H, J 8.5), 7.93 (s, 1H), 8.25 (s, 1H), 8.72 (brs, 1H), 11.01 (brs, 1H). HRMS m/z 409.1060.

1-(3-chlorophenyl)-3-(4-methyl-5-(2-(methylamino)pyrimidin-4-yl)thiazol-2-yl)urea (11) Prepared by treating 4-methyl-5-(2-(methylamino)pyrimidin-4-yl)thiazol-2-amine (100 mg, 452 µmol) and 3-chloroaniline (57.0 mg, 452 µmol) according to the general synthetic procedure to produce a white solid (82.0 mg, 49%). $^1$H NMR (DMSO-d6) δ 2.55 (s, 3H), 2.82 (d, 3H, J 3.5), 6.76 (s, 1H), 7.08 (d, 2H, J 7.0), 7.34 (d, 2H, J 8.0), 7.74 (s, 1H) 8.25 (s, 1H), 9.21 (brs, 1H), 10.75 (brs, 1H). HRMS m/z 375.0790.

1-(3-bromophenyl)-3-(4-methyl-5-(2-(methylamino)pyrimidin-4-yl)thiazol-2-yl)urea (12) Prepared by treating 4-methyl-5-(2-(methylamino)pyrimidin-4-yl)thiazol-2-amine (100 mg, 452 µmol) and 4-chloro-3-methylaniline (77.0 mg, 452 µmol) according to the general synthetic procedure to produce a white solid (59.0 mg, 31%). $^1$H NMR (DMSO-d6) δ 2.55 (s, 3H), 2.83 (d, 3H, J 4.0), 6.75 (d, 1H, J 4.0), 7.06 (d, 1H, J 4.5), 7.22 (d, 1H, J 8.0), 7.27 (t, 1H, J 8.0), 7.40 (d, 1H, J 6.5), 7.88 (s, 1H), 8.25 (s, 1H), 9.20 (brs, 1H), 10.80 (brs, 1H). HRMS m. 419.0276.

1-(4-methyl-5-(2-(methylamino)pyrimidin-4-yl)thiazol-2-yl)-3-(m-tolyl)urea (13) Obtained by treating 4-methyl-5-(2-(methylamino)pyrimidin-4-yl)thiazol-2-amine (100 mg, 452 µmol) and m-toluidine (48.0 mg, 452 µmol) according to the general synthetic procedure to produce a white solid (69.0 mg, 43%). $^1$H NMR (DMSO-d6) δ 2.30 (s, 3H), 2.55 (s, 3H), 2.83 (s, 3H, J 5.0), 6.75 (d, 1H, J 5.0), 6.86 (d, 1H, J 7.5), 7.05 (d, 1H, J 5.0), 7.20 (t, 1H, J 8.0), 7.26 (d, 1H, J 8.0), 7.34 (s, 1H), 8.25 (s, 1H), 8.92 (brs, 1H), 10.59 (brs, 1H). HRMS m/z 355.1333.

1-(4-methyl-5-(2-(methylamino)pyrimidin-4-yl)thiazol-2-yl)-3-(3-nitrophenyl)urea (14) Obtained by treating 4-methyl-5-(2-(methylamino)pyrimidin-4-yl)thiazol-2-amine (100 mg, 452 µmol) and 3-nitroaniline (62.0 mg, 452 µmol) according to the general synthetic procedure to produce a yellow solid (22.0 mg, 12%). $^1$H NMR (DMSO-d6) δ 2.56 (s, 3H), 2.83 (d, 3H, J 5.0), 6.76 (d, 1H, J 5.0), 7.08 (q, 1H, J 5.0), 7.59 (t, 1H, J 8.5), 7.83 (d, 1H, J 8.0), 7.88 (d, 1H, J 8.0), 8.26 (s, 1H), 8.61 (s, 1H), 9.56 (brs, 1H), 11.00 (brs, 1H). HRMS m/z 386.1035.

1-(3-cyanophenyl)-3-(4-methyl-5-(2-(methylamino)pyrimidin-4-yl)thiazol-2-yl)urea (15) Obtained by treating 4-methyl-5-(2-(methylamino)pyrimidin-4-yl)thiazol-2-amine (100 mg, 452 µmol) and 3-aminobenzonitrile (53.0 mg, 452 µmol) according to the general synthetic procedure to produce a white solid (15.0 mg, 9%). $^1$H NMR (DMSO-d6) δ 2.55 (s, 3H), 2.83 (d, 3H, J 4.5), 6.75 (d, 1H, J 4.5), 7.06 (d, 1H, J 4.0), 7.22 (d, 1H, 17.5) 7.27 (t, 1H, J 8.0), 7.40 (d, 1H, 17.0), 7.88 (s, 1H), 8.25 (s, 1H), 9.20 (brs, 1H), 10.76 (brs, 1H). HRMS m/z 366.1127.

1-(3-methoxyphenyl)-3-(4-methyl-5-(2-(methylamino)pyrimidin-4-yl)thiazol-2-yl)urea (16) Obtained by treating 4-methyl-5-(2-(methylamino)pyrimidin-4-yl)thiazol-2-amine (100 mg, 452 µmol) and 3-methoxyaniline (55.0 mg, 452 µmol) according to the general synthetic procedure to produce a white solid (78.0 mg, 47%). $^1$H NMR (DMSO-d6) δ 2.55 (s, 3H), 2.82 (s, 3H, J 4.0), 3.75 (s, 3H), 6.62 (d, 1H, J 7.0), 6.76 (d, 1H, J 3.5), 6.99 (d, 1H, J 7.0), 7.06 (d, 1H, J 4.5), 7.21 (d, 1H, J 8.0), 7.23 (s, 1H), 8.25 (s, 1H), 9.01 (brs, 1H), 10.58 (brs, 1H). HRMS m/z 371.1285.

1-(3-isopropylphenyl)-3-(4-methyl-5-(2-(methylamino)pyrimidin-4-yl)thiazol-2-yl)urea (17) Obtained by treating 4-methyl-5-(2-(methylamino)pyrimidin-4-yl)thiazol-2-amine (100 mg, 452 µmol) and 3-isopropylaniline (61.0 mg, 452 µmol) according to the general synthetic procedure to produce a white solid (45.0 mg, 26%). $^1$H NMR (DMSO-d6) δ 1.20 (d, 6H, J 7.0), 2.55 (s, 3H), 2.83 (d, 3H, J 4.0), 2.86-2.90 (m, 1H), 6.76 (d, 1H, J 4.0), 6.93 (d, 1H, J 7.0), 7.05 (d, 1H, J 4.5), 7.23 (t, 1H, J 7.5), 7.28 (d, 1H, J 7.5), 7.38 (s, 1H), 8.25 (s, 1H), 8.94 (brs, 1H), 10.57 (brs, 1H). HRMS m/z 383.1655.

1-(4-methyl-5-(2-(methylamino)pyrimidin-4-yl)thiazol-2-yl)-3-(3-(trifluoromethoxy) phenyl)urea (18) Obtained by treating 4-methyl-5-(2-(methylamino)pyrimidin-4-yl)thiazol-2-amine (100 mg, 452 µmol) and 2,5-bis(trifluoromethyl)aniline (80.0 mg, 452 µmol) according to the general synthetic procedure to produce a white solid (83.0 mg, 43%). $^1$H NMR (DMSO-d6) δ 2.55 (s, 3H), 2.82 (s, 3H, J 3.5), 6.78 (s, 1H), 7.01 (d, 1H, J 6.5), 7.08 (d, 1H, J 4.5), 7.41 (d, 1H, J 6.5), 7.44 (d, 1H, J 8.0), 7.72 (s, 1H), 8.25 (s, 1H), 9.35 (brs, 1H), 10.78 (brs, 1H). HRMS m/z 425.1001.

1-(3-ethoxyphenyl)-3-(4-methyl-5-(2-(methylamino)pyrimidin-4-yl)thiazol-2-yl)urea (19) Obtained by treating 4-methyl-5-(2-(methylamino)pyrimidin-4-yl)thiazol-2-amine (100 mg, 452 µmol) and 3-ethoxyaniline (62.0 mg, 452 µmol) according to the general synthetic procedure to produce a white solid (58.0 mg, 33%). $^1$H NMR (DMSO-d6) δ 1.33 (t, 3H, J 7.0), 2.55 (s, 3H), 2.82 (d, 3H, 14.5), 4.01 (q, 2H, J 7.0), 6.35 (d, 1H, J 7.0), 6.75 (d, 1H, J 4.5), 6.97 (d, 1H, J 7.5), 7.06 (d, 1H, J 4.5), 7.18-7.21 (m, 2H), 8.25 (s, 1H), 9.00 (brs, 1H), 10.53 (brs, 1H). HRMS m/z 385.1438.

1-(3-(difluoromethoxy)phenyl)-3-(4-methyl-5-(2-(methylamino)pyrimidin-4-yl)thiazol-2-yl)urea (20) Obtained by treating 4-methyl-5-(2-(methylamino)pyrimidin-4-yl)thiazol-2-amine (100 mg, 452 µmol) and 3-(difluoromethoxy)aniline (72.0 mg, 452 µmol) according to the general synthetic procedure to produce a white solid (49.0 mg, 27%). $^1$H NMR (DMSO-d6) δ 2.55 (s, 3H), 2.82 (d, 3H, J 4.5), 6.76 (d, 1H, J 4.5), 6.84 (d, 1H, J 7.0), 7.06 (d, 1H, J 4.5), 7.20 (t, 1H, J 74.5), 7.27 (d, 1H, J 7.5), 7.36 (t, 1H, J 8.0), 7.50 (s, 1H), 8.25 (s, 1H), 9.23 (brs, 1H), 10.71 (brs, 1H). HRMS m/z 407.1099.

1-(4-methyl-5-(2-(methylamino)pyrimidin-4-yl)thiazol-2-yl)-3-(3-(methylthio) phenyl)urea (21) Obtained by treating 4-methyl-5-(2-(methylamino)pyrimidin-4-yl)thiazol-2-amine (100 mg, 452 µmol) and 3-(methylthio)aniline (63.0 mg, 452 µmol) according to the general synthetic procedure to produce a white solid (74.0 mg, 43%). $^1$H NMR (DMSO-d6) δ 2.53 (s, 3H), 2.58 (s, 3H), 2.85 (d, 3H, J 3.5), 6.78 (s, 1H), 6.95 (d, 1H, J 7.0), 7.09 (d, 1H, J 4.5), 7.24 (s, 1H), 7.28 (t, 1H, 18.0), 7.52 (s, 1H), 8.28 (s, 1H), 9.08 (brs, 1H), 10.69 (brs, 1H). HRMS m/z 387.1062.

1-(4-methyl-5-(2-(methylamino)pyrimidin-4-yl)thiazol-2-yl)-3-(3-((trifluoromethyl) thio)phenyl)-urea (22) Obtained by treating 4-methyl-5-(2-(methylamino)pyrimidin-4-yl)thiazol-2-amine (100 mg, 452 µmol) and 3-((trifluoromethyl)thio)aniline (87.0 mg, 452 µmol) according to the general synthetic procedure to produce a white solid (53.0 mg, 27%). $^1$H NMR (DMSO-d6) 2.56 (s, 3H), 2.83 (d, 3H, J 5.0), 6.76 (d, 1H, J 5.0), 7.07 (q, 1H, J 4.5), 7.37 (d, 1H, J 7.5), 7.48 (t, 1H, J 8.0), 7.64 (d, 1H, J 8.0), 8.03 (s, 1H), 8.26 (s, 1H), 9.33 (brs, 1H), 10.81 (brs, 1H). HRMS m/z 441.0781.

1-(4-methyl-5-(2-(methylamino)pyrimidin-4-yl)thiazol-2-yl)-3-(3-((trifluoromethyl) sulfonyl)-phenyl)urea (23) Obtained by treating 4-methyl-5-(2-(methylamino)pyrimidin-4-yl)thiazol-2-amine (100 mg, 452 µmol) and 3-((trifluoromethyl)sulfonyl)aniline (101 mg, 452 µmol) according to the general synthetic procedure to produce a white solid (89.0 mg, 42%). $^1$H NMR (DMSO-d6) δ 2.56 (s, 3H), 2.83 (d, 3H, J 4.5), 6.76 (d, 1H, J 4.0), 7.11 (d, 1H, J 5.0), 7.98 (d, 2H, J 9.0), 8.03 (d, 2H, J 9.0), 8.27 (s, 1H), 9.94 (brs, 1H), 11.24 (brs, 1H). HRMS m/z 473.0670.

1-(4-chloro-3-(trifluoromethyl)phenyl)-3-(4-methyl-5-(2-(methylamino)pyrimidin-4-yl)thiazol-2-yl)urea (24) Obtained by treating 4-methyl-5-(2-(methylamino)pyrimidin-4-yl)thiazol-2-amine (100 mg, 452 µmol) and 4-chloro-3-(trifluoromethyl)aniline (88.0 mg, 452 µmol) according to the general synthetic procedure to produce a white solid (76.0 mg, 38%). $^1$H NMR (DMSO-d6) δ 2.55 (s, 3H), 2.81 (d, 3H, J 5.0), 6.74 (d, 1H, J 4.5), 7.06 (d, 1H, J 5.0), 7.62 (d, 1H, J 8.5), 7.77 (d, 1H, J 8.0), 8.16 (s, 1H), 8.25 (s, 1H), 9.57 (brs, 1H), 11.40 (brs, 1H). HRMS m/z 443.0668.

1-(4-fluoro-3-(trifluoromethyl)phenyl)-3-(4-methyl-5-(2-(methylamino)pyrimidin-4-yl)thiazol-2-yl)urea (25) Obtained by treating 4-methyl-5-(2-(methylamino)pyrimidin-4-yl)thiazol-2-amine (100 mg, 452 µmol) and 4-fluoro-3-(trifluoromethyl)aniline (81.0 mg, 452 µmol) according to the general synthetic procedure to produce a white solid (102 mg, 53%). $^1$H NMR (DMSO-d6) δ 2.55 (s, 3H), 2.82 (d, 3H, J 5.0), 6.75 (d, 1H, J 5.0), 7.07 (q, 1H, J 5.0), 7.46 (t, 1H, J 9.5), 7.75 (t, 1H, J 4.5), 8.04 (d, 1H, J 4.5), 8.25 (s, 1H), 9.38 (brs, 1H). HRMS m/z 427.0955.

1-(4-methyl-3-(trifluoromethyl)phenyl)-3-(4-methyl-5-(2-(methylamino)pyrimidin-4-yl)thiazol-2-yl)urea (26) Obtained by treating 4-methyl-5-(2-(methylamino)pyrimidin-4-yl)thiazol-2-amine (100 mg, 452 µmol) and 4-methyl-3-(trifluoromethyl)aniline (79.0 mg, 452 µmol) according to the general synthetic procedure to produce a white solid (42.0 mg, 22%). $^1$H NMR (DMSO-d6) δ 2.39 (s, 3H), 2.55 (s, 3H), 2.82 (d, 3H, J 5.0), 6.76 (d, 1H, J 5.0), 7.06 (q, 1H, J 4.5), 7.37 (d, 1H, J 5.5), 7.59 (d, 1H, J 8.0), 7.96 (s, 1H), 8.25 (s, 1H), 9.25 (brs, 1H), 10.80 (brs, 1H). HRMS m/z 423.1213.

1-(3,4-bis(trifluoromethyl)phenyl)-3-(4-methyl-5-(2-(methylamino)pyrimidin-4-yl)thiazol-2-yl)urea (27) Obtained by treating 4-methyl-5-(2-(methylamino)pyrimidin-4-yl)thiazol-2-amine (100 mg, 452 mol) and 3,4-bis(trifluoromethyl)aniline (103 mg, 452 µmol) according to the general synthetic procedure to produce a white solid (88.0 mg, 41%). H NMR (DMSO-d6) δ 2.56 (s, 3H), 2.83 (d, 3H, J 3.5), 6.76 (s, 1H), 7.10 (d, 1H, J 4.0), 7.95 (d, 1H, J 8.5), 7.99 (s, 1H), 8.27 (s, 1H), 8.29 (s, 1H), 9.82 (brs, 1H). HRMS m. 477.0932.

1-(3-fluoro-4-(trifluoromethyl)phenyl)-3-(4-methyl-5-(2-(methylamino)pyrimidin-4-yl)thiazol-2-yl)urea (28) Obtained by treating 4-methyl-5-(2-(methylamino)pyrimidin-4-yl)thiazol-2-amine (100 mg, 452 µmol) and 3-fluoro-4-(trifluoromethyl)aniline (81.0 mg, 452 µmol) according to the general synthetic procedure to produce a white solid (77.0 mg, 40%). $^1$H NMR (DMSO-d6) δ 2.56 (s, 3H), 2.83 (d, 3H, J 4.5), 6.75 (d, 1H, J 4.5), 7.09 (q, 1H, J 4.5), 7.45 (d, 1H, J 8.5), 7.68 (t, 1H, J 8.5), 7.77 (d, 1H, I 8.5), 8.26 (s, 1H), 9.65 (brs, 1H). HRMS m/z 427.0953.

1-(3-chloro-4-methylphenyl)-3-(4-methyl-5-(2-(methylamino)pyrimidin-4-yl)thiazol-2-yl)urea Obtained by treating 4-methyl-5-(2-(methylamino)pyrimidin-4-yl)thiazol-2-amine (100 mg, 452 µmol) and 3-chloro-4-methylaniline (63.0 mg, 452 µmol) according to the general synthetic procedure to produce a white solid (71.0 mg, 41%). $^1$H NMR (DMSO-d6) δ 2.27 (s, 3H), 2.55 (s, 3H), 2.81 (d, 3H, J 4.5), 6.75 (d, 1H, J 4.5), 7.05 (d, 1H, J 4.0), 7.27 (d, 2H, J 8.0), 7.71 (s, 1H), 8.25 (s, 1H), 9.11 (brs, 1H), 10.79 (brs, 1H). HRMS m/z 389.0953.

1-(4-chloro-3-methylphenyl)-3-(4-methyl-5-(2-(methylamino)pyrimidin-4-yl)thiazol-2-yl)urea (30) Obtained by treating 4-methyl-5-(2-(methylamino)pyrimidin-4-yl)thiazol-2-amine (100 mg, 452 µmol) and 4-chloro-3-methylaniline (63.0 mg, 452 µmol) according to the general synthetic procedure to produce a white solid (105 mg, 60%). H NMR (DMSO-d6) δ 2.31 (s, 3H), 2.55 (s, 3H), 2.82 (d, 3H, J 5.0), 6.75 (d, 1H, J 5.0), 7.05 (d, 1H, J 4.5), 7.33 (d, 1H, J 19.0), 7.36 (d, 1H, J 10.5), 7.50 (s, 1H), 8.25 (s, 1H), 9.05 (brs, 1H), 10.69 (brs, 1H). HRMS m/z 389.0950.

1-(3-chloro-4-(morpholinomethyl)phenyl)-3-(4-methyl-5-(2-(methylamino)pyrimidin-4-yl)thiazol-2-yl)urea (31) Obtained by treating 4-methyl-5-(2-(methylamino)pyrimidin-4-yl)thiazol-2-amine (100 mg, 452 µmol) and 3-chloro-4-(morpholinomethyl)aniline (101 mg, 452 µmol) according to the general synthetic procedure to produce a white solid (63.0 mg, 30%). $^1$H NMR (DMSO-d6) δ 2.39 (t, 4H, J 4.5), 2.50 (s, 3H), 2.82 (d, 3H, J 4.5), 3.50 (s, 2H), 3.57 (t, 4H, J 4.0), 6.75 (d, 1H, J 4.5), 7.05 (d, 1H, J 4.5), 7.35 (d, 1H, J 7.5), 7.39 (d, 1H, J 8.0), 7.73 (s, 1H) 8.24 (s, 1H), 9.29 (brs, 1H), 10.97 (brs, 1H). HRMS m/z 473.1406.

1-(4-methyl-5-(2-(methylamino)pyrimidin-4-yl)thiazol-2-yl)-3-(4-((4-methylpiperazin-1-yl)methyl)-3-(trifluoromethyl)phenyl)urea (32) Obtained by treating 4-methyl-5-(2-(methylamino)pyrimidin-4-yl)thiazol-2-amine (100 mg, 452 µmol) and 4-((4-methylpiperazin-1-yl)methyl)-3-(trifluoromethyl)aniline (123 mg, 452 µmol) according to the general synthetic procedure to produce a white solid (73.0 mg, 31%). $^1$H NMR (CD$_3$OD/CDCl$_3$) δ 2.27 (s, 3H), 2.48 (brs, 8H), 2.61 (s, 3H), 2.97 (s, 3H), 3.60 (s, 2H), 6.74 (d, 1H, J 5.0), 7.64 (dd, 1H, J 8.5 & 2.5), 7.68 (d, 1H, J 8.5), 7.79 (d, 1H, J 2.0), 8.15 (d, 1H, J 5.0). HRMS m/z 521.2057.

1-(4-((4-ethylpiperazin-1-yl)methyl)-3-(trifluoromethyl) phenyl)-3-(4-methyl-5-(2-(methylamino)pyrimidin-4-yl) thiazol-2-yl)urea (33) Obtained by treating 4-methyl-5-(2-(methylamino)pyrimidin-4-yl)thiazol-2-amine (100 mg, 452 µmol) and 4-((4-ethylpiperazin-1-yl)methyl)-3-(trifluoromethyl)aniline (129 mg, 452 µmol) according to the general synthetic procedure to produce a white solid (55.0 mg, 23%). $^1$H NMR (CD$_3$OD/CDCl$_3$) δ 1.09 (t, 3H, J 7.5), 2.44 (q, 2H, J 7.0), 2.49 (brs, 8H), 2.61 (s, 3H), 2.97 (s, 3H), 3.62 (s, 2H), 6.75 (d, 1H, J 5.5), 7.64 (d, 1H, J 8.5), 7.68 (d, 1H, J 8.5), 7.82 (s, 1H), 8.15 (d, 1H, J 5.0). HRMS m/z 535.2205.

1-(4-((4-isopropylpiperazin-1-yl)methyl)-3-(trifluoromethyl)phenyl)-3-(4-methyl-5-(2-(methylamino)pyrimidin-4-yl)thiazol-2-yl)urea (34) Obtained by treating 4-methyl-5-(2-(methylamino)pyrimidin-4-yl)thiazol-2-amine (100 mg, 452 µmol) and 4-((4-isopropylpiperazin-1-yl)methyl)-3-(trifluoromethyl)aniline (136 mg, 452 µmol) according to the general synthetic procedure to produce a white solid (112 mg, 45%). $^1$H NMR (CD$_3$OD/CDCl$_3$) δ 1.07 (d, 6H, 16.0), 2.52-2.66 (m, 12H), 2.96 (s, 3H), 3.61 (s, 2H), 6.74 (d, 1H, J 5.5), 7.65 (d, 1H, J 7.5), 7.73 (d, 1H, J 8.5), 7.82 (s, 1H), 8.16 (d, 1H, J 5.0). HRMS m/z 549.2369.

1-(4-((4-acetylpiperazin-1-yl)methyl)-3-(trifluoromethyl)phenyl)-3-(4-methyl-5-(2-(methylamino)pyrimidin-4-yl)thiazol-2-yl)urea (35) Obtained by treating 4-methyl-5-(2-(methylamino)pyrimidin-4-yl)thiazol-2-amine (100 mg, 452 μmol) and 1-(4-(4-amino-2-(trifluoromethyl)benzyl)piperazin-1-yl)ethan-1-one (135 mg, 452 μmol) according to the general synthetic procedure to produce a white solid (82.0 mg, 33%). H NMR (CD$_3$OD/CDCl$_3$) δ 2.07 (s, 3H), 2.43 (t, 2H, J 5.0), 2.47 (t, 2H, 15.0), 2.60 (s, 3H), 2.96 (s, 3H), 3.49 (t, 2H, J 5.0), 3.59 (t, 2H, J 4.5), 3.62 (s, 2H), 6.73 (d, 1H, J 5.5), 7.66 (d, 1H, J 8.5), 7.69 (d, 1H, J 8.5), 7.80 (s, 1H), 8.15 (d, 1H, J 5.0).

HRMS m/z 549.2010.

1-(4-methyl-5-(2-(methylamino)pyrimidin-4-yl)thiazol-2-yl)-3-(4-((4-(methylsulfonyl) piperazin-1-yl)methyl)-3-(trifluoromethyl)phenyl)urea (36) Obtained by treating 4-methyl-5-(2-(methylamino)pyrimidin-4-yl)thiazol-2-amine (100 mg, 452 μmol) and 4-((4-(methylsulfonyl)piperazin-1-yl)methyl)-3-(trifluoromethyl)aniline (152 mg, 452 μmol) according to the general synthetic procedure to produce a white solid (96.0 mg, 37%). $^1$H NMR (CD$_3$OD/CDCl$_3$) δ 2.56 (t, 4H, J 5.0), 2.61 (s, 3H), 2.81 (s, 3H), 2.97 (app s, 3H), 3.23 (t, 4H, J 5.0), 3.65 (s, 2H), 6.73 (d, 1H, J 5.5), 7.64-7.68 (m, 2H), 7.78 (s, 1H), 8.15 (d, 1H, J 5.0). HRMS m/z 585.1679.

1-(4-methyl-5-(2-(methylamino)pyrimidin-4-yl)thiazol-2-yl)-3-(4-(morpholinomethyl)-3-(trifluoromethyl)phenyl) urea (37) Obtained by treating 4-methyl-5-(2-(methylamino)pyrimidin-4-yl)thiazol-2-amine (100 mg, 452 μmol) and 4-(morpholinomethyl)-3-(trifluoromethyl)aniline (117 mg, 452 μmol) according to the general synthetic procedure to produce a white solid (63.0 mg, 28%). $^1$H NMR (CD$_3$OD/CDCl$_3$) δ 2.47 (s, 4H), 2.61 (s, 3H), 2.97 (s, 3H), 3.60 (s, 2H), 3.70 (s, 4H), 6.75 (d, 1H, J 5.0), 7.64 (d, 1H, J 7.5), 7.70 (d, 1H, J 8.0), 7.82 (s, 1H), 8.15 (d, 1H, J 4.0). HRMS m/z 508.1730.

1-(4-methyl-5-(2-(methylamino)pyrimidin-4-yl)thiazol-2-yl)-3-(4-(piperidin-1-ylmethyl)-3-(trifluoromethyl)phenyl)urea (38) Obtained by treating 4-methyl-5-(2-(methylamino)pyrimidin-4-yl)thiazol-2-amine (100 mg, 452 μmol) and 4-(piperidin-1-ylmethyl)-3-(trifluoromethyl)aniline (116 mg, 452 μmol) according to the general synthetic procedure to produce a white solid (40.0 mg, 18%). $^1$H NMR (CD$_3$OD/CDCl$_3$) δ 1.45 (s, 2H), 1.56-1.60 (m, 4H), 2.43 (s, 4H), 2.60 (s, 3H), 2.97 (s, 3H), 3.59 (s, 2H), 6.72 (d, 1H, J 5.5), 7.62 (dd, 1H, J 8.5 & 2.0), 7.71 (d, 1H, J 8.5), 7.81 (d, 1H, J 2.0), 8.14 (d, 1H, J 5.0). HRMS m/z 506.1939.

1-(4-((4-aminopiperidin-1-yl)methyl)-3-(trifluoromethyl)phenyl)-3-(4-methyl-5-(2-(methylamino)pyrimidin-4-yl)thiazol-2-yl)urea (39) To a solution of tert-butyl (1-(4-(3-(4-methyl-5-(2-(methylamino)pyrimidin-4-yl)thiazol-2-yl)ureido)-2-(trifluoromethyl)benzyl)piperidin-4-yl)carbamate4-methyl-5-(2-(methylamino)-pyrimidin-4-yl)thiazol-2-amine (131 mg, 211 μmol) in DCM was added TFA (0.2 mL) and refluxed overnight, and concentrated under reduced pressure. The residue was taken to pH>11 with saturated aqueous Na$_2$CO$_3$ solution, and extracted with DCM. The organic extracts were combined, and concentrated under reduced pressure. The residue was purified by Biotage® FlashMaster Personal® chromatography (silica gel:DCM ramping to DCM:MeOH=90:10), and then washed with MeOH to give 39 as a white solid (64.0 mg, 59%). $^1$H NMR (CD$_3$OD/CDCl$_3$) δ 1.39-1.47 (m, 2H), 1.80 (d, 2H, J 12.0), 2.08 (t, 2H, J 11.5), 2.60 (s, 3H), 2.65-2.70 (m, 1H), 2.83 (d, 2H, J 11.5), 2.96 (s, 3H), 3.58 (s, 2H), 6.74 (d, 1H, J 5.5), 7.63 (dd, 1H, J 8.5 & 2.0), 7.69 (d, 1H, 0.8.5), 7.82 (d, 1H, J 2.0), 8.15 (d, 1H, J 5.5). HRMS m/z 521.2047.

1-(4-methyl-5-(2-(methylamino)pyrimidin-4-yl)thiazol-2-yl)-3-(4-((4-methylpiperidin-1-yl)methyl)-3-(trifluoromethyl)phenyl)urea (40) Obtained by treating 4-methyl-5-(2-(methylamino)pyrimidin-4-yl)thiazol-2-amine (100 mg, 452 μmol) and 4-((4-methylpiperidin-1-yl)methyl)-3-(trifluoromethyl)aniline (122 mg, 452 μmol) according to the general synthetic procedure to produce a white solid (75.0 mg, 34%). $^1$H NMR (CD$_3$OD/CDCl$_3$) δ 0.90 (d, 3H, J 6.5), 1.19-1.26 (m, 2H), 1.37 (brs, 1H), 1.59 (d, 2H, J 12.5), 2.00 (t, 2H, J 11.5), 2.60 (s, 3H), 2.80 (d, 2H, J 11.5), 2.96 (s, 3H), 3.56 (s, 2H), 6.72 (d, 1H, 15.0), 7.61 (d, 1H, 0.8.5), 7.70 (d, 1H, J 8.5), 7.80 (s, 1H), 8.14 (d, 1H, J 5.0). HRMS m/z 520.2108.

1-(4-methyl-5-(2-(methylamino)pyrimidin-4-yl)thiazol-2-yl)-3-(4-(trifluoromethyl) phenyl)urea (41) Obtained by treating 4-methyl-5-(2-(methylamino)pyrimidin-4-yl)thiazol-2-amine (100 mg, 452 μmol) and 4-(trifluoromethyl)aniline (72.0 mg, 452 μmol) according to the general synthetic procedure to produce a white solid (67.0 mg, 36%). $^1$H NMR (DMSO-d6) δ 2.56 (s, 3H), 2.82 (d, 3H, J 4.5), 6.76 (d, 1H, J 4.5), 7.08 (d, 1H, J 5.0), 7.66 (d, 2H, J 8.5), 7.73 (d, 2H, J 8.5), 8.26 (s, 1H), 9.42 (brs, 1H), 10.83 (brs, 1H). HRMS m/z 408.1051.

1-(4-fluorophenyl)-3-(4-methyl-5-(2-(methylamino)pyrimidin-4-yl)thiazol-2-yl)urea (42) Obtained by treating 4-methyl-5-(2-(methylamino)pyrimidin-4-yl)thiazol-2-amine (100 mg, 452 μmol) and 4-fluoroaniline (50.0 mg, 452 μmol) according to the general synthetic procedure to produce a white solid (88.0 mg, 55%). $^1$H NMR (DMSO-d6) δ 2.55 (s, 3H), 2.82 (d, 3H, J 4.5), 6.75 (d, 1H, J 5.0), 7.05 (q, 1H, J 4.0), 7.16 (t, 2H, J 8.5), 7.51 (q, 2H, J 4.5), 8.25 (s, 1H), 9.05 (brs, 1H), 10.65 (brs, 1H). HRMS m: 359.1080.

1-(4-chlorophenyl)-3-(4-methyl-5-(2-(methylamino)pyrimidin-4-yl)thiazol-2-yl)urea (43) Obtained by treating 4-methyl-5-(2-(methylamino)pyrimidin-4-yl)thiazol-2-amine (100 mg, 452 μmol) and 4-chloroaniline (57.0 mg, 452 μmol) according to the general synthetic procedure to produce a white solid (77.0 mg, 46%). $^1$H NMR (DMSO-d6) δ 2.55 (s, 3H), 2.82 (d, 3H, J 4.0), 6.75 (s, 1H), 7.07 (d, 1H, J 4.5), 7.36 (d, 2H, J 8.5), 7.54 (d, 2H, 17.5), 8.25 (s, 1H), 9.16 (brs, 1H), 10.70 (brs, 1H). HRMS m 375.0795.

1-(4-methyl-5-(2-(methylamino)pyrimidin-4-yl)thiazol-2-yl)-3-(p-tolyl)urea (44) Obtained by treating 4-methyl-5-(2-(methylamino)pyrimidin-4-yl)thiazol-2-amine (100 mg, 452 μmol) and p-toluidine (48.0 mg, 452 μmol) according to the general synthetic procedure to produce a white solid (76.0 mg, 48%). $^1$H NMR (DMSO-d6) δ 2.26 (s, 3H), 2.55 (s, 3H), 2.82 (s, 3H, J 4.5), 6.75 (d, 1H, J 4.5), 7.05 (q, 1H, J 4.5), 7.12 (d, 2H, J 8.5), 7.37 (d, 2H, J 8.0), 8.25 (s, 1H), 8.90 (brs, 1H), 10.55 (brs, 1H).

HRMS m/z 355.1337.

1-(4-methoxyphenyl)-3-(4-methyl-5-(2-(methylamino)pyrimidin-4-yl)thiazol-2-yl)urea (45) Obtained by treating 4-methyl-5-(2-(methylamino)pyrimidin-4-yl)thiazol-2-amine (100 mg, 452 μmol) and 4-methoxyaniline (55.0 mg, 452 μmol) according to the general synthetic procedure to produce a white solid (86.0 mg, 51%). $^1$H NMR (DMSO-d6) δ 2.54 (s, 3H), 2.82 (s, 3H, J 4.5), 3.73 (s, 3H), 6.75 (d, 1H, J 3.5), 6.90 (d, 2H, J 8.5), 7.05 (d, 1H, J 4.5), 7.39 (d, 1H, J 8.5), 8.24 (s, 1H), 8.82 (brs, 1H), 10.54 (brs, 1H). HRMS m/z 371.1288.

1-(5-(2-(dimethylamino)pyrimidin-4-yl)-4-methylthiazol-2-yl)-3-(3-(trifluoromethyl) phenyl)urea (46) Obtained by treating 5-(2-(dimethylamino)pyrimidin-4-yl)-4-methylthiazol-2-amine (100 mg, 425 μmol) and 3-(trifluoromethyl) aniline (68.0 mg, 425 μmol) according to the general synthetic procedure to produce a white solid (88.0 mg, 50%). $^1$H NMR (DMSO-d6) δ 2.59 (s, 3H), 3.16 (s, 6H), 6.75 (d, 1H, J 5.0), 7.36 (d, 1H, J 8.0), 7.54 (t, 1H, J 8.0), 7.68 (d, 1H, J 8.0), 7.99 (s, 1H), 8.31 (d, 1H, J 5.0), 9.22 (brs, 1H), 10.74 (brs, 1H). HRMS m/z 423.1216.

1-(3-chlorophenyl)-3-(5-(2-(dimethylamino)pyrimidin-4-yl)-4-methylthiazol-2-yl)urea (47) Obtained by treating 5-(2-(dimethylamino)pyrimidin-4-yl)-4-methylthiazol-2-amine (100 mg, 425 μmol) and 3-chloroaniline (53.0 mg, 425 μmol) as a white solid (96.0 mg, 59%). $^1$H NMR (DMSO-d6) δ 2.58 (s, 3H), 3.16 (s, 6H), 6.75 (d, 1H, J 4.5), 7.08 (d, 1H, J 7.5), 7.32 (d, 1H, J 8.0), 7.35 (t, 1H, J 8.0), 7.71 (s, 1H), 8.31 (d, 1H, J 5.0), 9.07 (brs, 1H), 10.64 (br s, 1H). HRMS m/z 389.0952.

1-(3-chloro-4-methylphenyl)-3-(5-(2-(dimethylamino) pyrimidin-4-yl)-4-methylthiazol-2-yl)urea (48) Obtained by treating 5-(2-(dimethylamino)pyrimidin-4-yl)-4-methylthiazol-2-amine (100 mg, 425 μmol) and 3-chloro-4-methylaniline (59.0 mg, 425 μmol) according to the general synthetic procedure to produce a white solid (79.0 mg, 47%). $^1$H NMR (DMSO-d6) δ 2.30 (s, 3H), 2.58 (s, 3H), 3.16 (s, 6H), 6.75 (d, 1H, J 5.0), 7.27 (d, 2H, J 8.0), 7.68 (s, 1H), 8.31 (d, 1H, J 5.0), 8.96 (brs, 1H), 10.58 (brs, 1H). HRMS m/z 403.1110.

1-(5-(2-(dimethylamino)pyrimidin-4-yl)-4-methylthiazol-2-yl)-3-(4-((4-methylpiperazin-1-yl)methyl)-3-(trifluoromethyl)phenyl)urea (49) Obtained by treating 5-(2-(dimethylamino)pyrimidin-4-yl)-4-methylthiazol-2-amine (100 mg, 425 μmol) and 4-((4-methylpiperazin-1-yl)methyl)-3-(trifluoromethyl)aniline (115 mg, 425 mol) according to the general synthetic procedure to produce a white solid (62.0 mg, 28%). $^1$H NMR (CD$_3$OD/CDCl$_3$) δ 2.28 (s, 3H), 2.50 (brs, 8H), 2.60 (s, 3H), 3.18 (s, 6H), 3.60 (s, 2H), 6.70 (d, 1H, J 5.5), 7.64 (d, 1H, J 8.0), 7.68 (d, 1H, J 8.5), 7.81 (s, 1H), 8.20 (d, 1H, J 5.0). HRMS in: 535.2215.

1-(4-((4-acetylpiperazin-1-yl)methyl)-3-(trifluoromethyl) phenyl)-3-(5-(2-(dimethylamino)-pyrimidin-4-yl)-4-methylthiazol-2-yl)urea (50) Obtained by treating 5-(2-(dimethylamino)pyrimidin-4-yl)-4-methylthiazol-2-amine (100 mg, 425 μmol) and 1-(4-(4-amino-2-(trifluoromethyl)benzyl) piperazin-1-yl)ethan-1-one (126 mg, 425 μmol) according to the general synthetic procedure to produce a white solid (93.0 mg, 39%). $^1$H NMR (CD$_3$OD/CDCl$_3$) δ 2.08 (s, 3H), 2.43 (t, 2H, J 4.5), 2.48 (t, 2H, J 5.0), 2.61 (s, 3H), 3.18 (s, 6H), 3.51 (t, 2H, J 5.5), 3.59 (t, 2H, J 5.5), 3.62 (s, 2H), 6.70 (d, 1H, J 5.5), 7.66 (d, 1H, J 8.5), 7.70 (d, 1H, J 8.5), 7.81 (s, 1H), 8.20 (d, 1H, 15.0). HRMS m/z 563.2155.

1-(5-(2-aminopyrimidin-4-yl)-4-methylthiazol-2-yl)-3-(3-(trifluoromethyl)phenyl)urea (51) Obtained by treating 5-(2-aminopyrimidin-4-yl)-4-methylthiazol-2-amine (100 mg, 482 μmol) and 3-(trifluoromethyl)aniline (78.0 mg, 482 μmol) according to the general synthetic procedure to produce a white solid (96.0 mg, 41%). $^1$H NMR (DMSO-d6) δ 2.56 (s, 3H), 6.30 (s, 2H), 6.78 (d, 1H, J 5.0), 7.37 (d, 1H, J 8.0), 7.55 (t, 1H, J 8.0), 7.68 (d, 1H, J 8.0), 8.02 (s, 1H), 8.23 (d, 1H, J 5.0), 9.22 (brs, 1H), 10.71 (brs, 1H). HRMS m. 395.0893.

1-(5-(2-(ethylamino)pyrimidin-4-yl)-4-methylthiazol-2-yl)-3-(4-((4-methylpiperazin-1-yl)methyl)-3-(trifluoromethyl)phenyl)urea (52) Obtained by treating 5-(2-(ethylamino)pyrimidin-4-yl)-4-methylthiazol-2-amine (100 mg, 425 μmol) and 4-((4-methylpiperazin-1-yl)methyl)-3-(trifluoromethyl)aniline (115 mg, 425 μmol) according to the general synthetic procedure to produce a white solid (95.0 mg, 42%). $^1$H NMR (CD$_3$OD/CDCl$_3$) δ 1.23 (t, 3H, J 7.0), 2.28 (s, 3H), 2.50 (brs, 8H), 2.60 (s, 3H), 3.43 (q, 2H), 3.60 (s, 2H), 6.74 (d, 1H, J 5.5), 7.64 (dd, 1H, J 8.5 & 2.0), 7.68 (d, 1H, J 8.5), 7.81 (d, 1H, J 2.0), 8.14 (d, 1H, J 5.5). HRMS m/z 535.2208.

1-(5-(2-(ethylamino)pyrimidin-4-yl)-4-methylthiazol-2-yl)-3-(4-((4-ethylpiperazin-1-yl)methyl)-3-(trifluoromethyl) phenyl)urea (53) Obtained by treating 5-(2-(ethylamino) pyrimidin-4-yl)-4-methylthiazol-2-amine (100 mg, 425 μmol) and 4-((4-ethylpiperazin-1-yl)methyl)-3-(trifluoromethyl)aniline (121 mg, 425 μmol) according to the general synthetic procedure to produce a white solid (67.0 mg, 29%). $^1$H NMR (CD$_3$OD/CDCl$_3$) δ 1.08 (t, 3H, J 7.5), 1.23 (t, 3H, J 7.5), 2.43 (q, 2H, J 7.0), 2.51 (brs, 8H), 2.60 (s, 3H), 3.43 (q, 2H, J 7.0), 3.60 (s, 2H), 6.73 (d, 1H, J 5.5), 7.64 (dd, 1H, J 8.5 & 2.0), 7.68 (d, 1H, 18.5), 7.80 (d, 1H, J 2.0), 8.14 (d, 1H, J 5.0). HRMS m/z 549.2370.

1-(5-(2-(ethylamino)pyrimidin-4-yl)-4-methylthiazol-2-yl)-3-(4-((4-isopropylpiperazin-1-yl)methyl)-3-(trifluoromethyl)phenyl)urea (54) Obtained by treating 5-(2-(ethylamino)pyrimidin-4-yl)-4-methylthiazol-2-amine (100 mg, 425 μmol) and 4-((4-isopropylpiperazin-1-yl)methyl)-3-(trifluoromethyl)aniline (126 mg, 452 μmol) as a white solid (77.0 mg, 33%). $^1$H NMR (CD$_3$OD/CDCl$_3$) δ 1.07 (d, 6H, J 6.5), 2.52-2.66 (m, 12H), 3.43 (q, 2H, J 7.0), 3.60 (s, 2H), 6.72 (d, 1H, J 5.5), 7.64 (dd, 1H, J 8.5 & 2.0), 7.68 (d, 1H, J 8.5), 7.78 (d, 1H, J 2.0), 8.14 (d, 1H, J 5.5). HRMS m/z 563.2529.

1-(4-((4-acetylpiperazin-1-yl)methyl)-3-(trifluoromethyl) phenyl)-3-(5-(2-(ethylamino) pyrimidin-4-yl)-4-methylthiazol-2-yl)urea (55) Obtained by treating 5-(2-(ethylamino) pyrimidin-4-yl)-4-methylthiazol-2-amine (100 mg, 425 μmol) and 1-(4-(4-amino-2-(trifluoromethyl)benzyl)piperazin-1-yl)ethan-1-one (126 mg, 425 μmol) according to the general synthetic procedure to produce a white solid (101 mg, 43%). $^1$H NMR (CD$_3$OD/CDCl$_3$) δ 1.24 (t, 3H, J 7.0), 2.08 (s, 3H), 2.44 (t, 2H, J 4.5), 2.49 (t, 2H, J 5.0), 2.60 (s, 3H), 3.44 (q, 2H, J 7.0) 3.52 (t, 2H, J 5.5), 3.59 (t, 2H, J 5.5), 3.63 (s, 2H), 6.75 (d, 1H, J 5.5), 7.66 (d, 1H, J 8.0), 7.71 (d, 1H, J 8.0), 7.82 (s, 1H), 8.14 (d, 1H, J 5.5). HRMS m/z 563.2163.

1-(5-(2-(ethylamino)pyrimidin-4-yl)-4-methylthiazol-2-yl)-3-(4-(morpholinomethyl)-3-(trifluoromethyl)phenyl) urea (56) Obtained by treating 5-(2-(ethylamino)pyrimidin-4-yl)-4-methylthiazol-2-amine (100 mg, 425 μmol) and 4-(morpholinomethyl)-3-(trifluoromethyl)aniline (109 mg, 425 μmol) according to the general synthetic procedure to produce a white solid (120 mg, 55%). $^1$H NMR (CD$_3$OD/CDCl$_3$) δ 1.23 (t, 3H, J 7.5), 2.46 (t, 4H, J 5.0), 2.60 (s, 3H), 3.43 (q, 2H, J 7.0), 3.60 (s, 2H), 3.70 (t, 4H, J 4.5), 6.73 (d, 1H, J 5.5), 7.64 (dd, 1H, J 8.5 & 1.5), 7.70 (d, 1H, J 8.5), 7.81 (d, 1H, J 2.0), 8.14 (d, 1H, J 5.0). HRMS m/z 522.1890.

1-(5-(2-(ethylamino)pyrimidin-4-yl)-4-methylthiazol-2-yl)-3-(4-((4-methylpiperidin-1-yl)methyl)-3-(trifluoromethyl)phenyl)urea (57) Obtained by treating 5-(2-(ethylamino)pyrimidin-4-yl)-4-methylthiazol-2-amine (100 mg, 425 μmol) and 4-((4-methylpiperidin-1-yl)methyl)-3-(trifluoromethyl)aniline (114 mg, 425 μmol) according to the general synthetic procedure to produce a white solid (79.0 mg, 35%). $^1$H NMR (CD$_3$OD/CDCl$_3$) δ 0.90 (d, 3H, J 6.5), 1.18-1.25 (m, 5H), 1.34-1.38 (m, 1H), 1.58 (app d, 2H, J 12.5), 1.99 (t, 2H, J 11.0), 2.59 (s, 3H), 2.79 (d, 2H, J 11.5), 3.43 (q, 2H, J 7.0), 3.55 (s, 2H), 6.70 (d, 1H, J 5.5), 7.61 (d, 1H, J 8.5), 7.69 (d, 1H, J 8.5), 7.77 (d, 1H, J 1.5), 8.13 (d, 1H, J 5.0). HRMS m/z 534.2250.

1-(5-(2-(methylamino)pyrimidin-4-yl)thiazol-2-yl)-3-(4-((4-methylpiperazin-1-yl)methyl)-3-(trifluoromethyl)phenyl)urea (58) Obtained by treating 5-(2-(methylamino)pyrimidin-4-yl)thiazol-2-amine (100 mg, 482 µmol) and 4-((4-methylpiperazin-1-yl)methyl)-3-(trifluoromethyl)aniline (131 mg, 482 µmol) according to the general synthetic procedure to produce a yellow solid (58.0 mg, 24%). $^1$H NMR (DMSo-d6) δ 2.17 (s, 3H), 2.38 (br s, 8H), 2.83 (d, 3H, J 4.5), 3.54 (s, 2H), 7.02 (d, 1H, J 5.0), 7.07 (q, 1H, J 4.5), 7.66 (s, 2H), 7.98 (s, 1H), 8.20 (s, 1H), 8.23 (s, 1H), 9.42 (brs, 1H), 11.07 (brs, 1H). HRMS m: 507.1899.

1-(4-((4-ethylpiperazin-1-yl)methyl)-3-(trifluoromethyl)phenyl)-3-(5-(2-(methylamino) pyrimidin-4-yl)thiazol-2-yl)urea (59) Obtained by treating 5-(2-(methylamino)pyrimidin-4-yl)thiazol-2-amine (100 mg, 482 µmol) and 4-((4-ethylpiperazin-1-yl)methyl)-3-(trifluoromethyl)aniline (138 mg, 482 µmol) according to the general synthetic procedure to produce a yellow solid (35.0 mg, 14%). $^1$H NMR (CD$_3$OD/CDCl$_3$) 1.08 (t, 3H, J 7.5), 2.43 (q, 2H, J 7.5), 2.51 (brs, 8H), 2.96 (s, 3H), 3.61 (s, 2H), 6.81 (d, 1H, J 5.0), 7.65 (d, 1H, J 8.5), 7.68 (d, 1H, J 8.5), 7.77 (s, 1H), 7.94 (s, 1H), 8.13 (d, 1H, J 4.5).

HRMS m/z 521.2057.

1-(4-((4-isopropylpiperazin-1-yl)methyl)-3-(trifluoromethyl)phenyl)-3-(5-(2-(methylamino) pyrimidin-4-yl)thiazol-2-yl)urea (60) Obtained by treating 5-(2-(methylamino)pyrimidin-4-yl)thiazol-2-amine (100 mg, 483 µmol) and 4-((4-isopropylpiperazin-1-yl)methyl)-3-(trifluoromethyl)aniline (145 mg, 483 µmol) according to the general synthetic procedure to produce a yellow solid (51.0 mg, 20%). $^1$H NMR (DMSO-d6) δ 0.96 (d, 6H, J 6.5), 2.39 (br s, 8H), 2.61-2.66 (m, 1H), 2.83 (d, 3H, 14.5), 3.53 (s, 2H), 7.02 (d, 1H, J 5.0), 7.07 (q, 1H, J 4.5), 7.66 (br s, 2H), 7.99 (br s, 1H), 8.20 (s, 1H), 8.23 (br s, 1H), 9.45 (br s, 1H), 11.06 (br s, 1H). HRMS m/z 535.2218.

1-(4-((4-acetylpiperazin-1-yl)methyl)-3-(trifluoromethyl)phenyl)-3-(5-(2-(methylamino)-pyrimidin-4-yl)thiazol-2-yl)urea (61) Obtained by treating 5-(2-(methylamino)pyrimidin-4-yl)thiazol-2-amine (100 mg, 483 µmol) and 1-(4-(4-amino-2-(trifluoromethyl)benzyl)piperazin-1-yl)ethan-1-one (145 mg, 483 mol) according to the general synthetic procedure to produce a yellow solid (59.0 mg, 23%). $^1$H NMR (DMSO-d6) δ 1.98 (s, 3H), 2.32 (t, 2H, J 4.5), 2.38 (t, 2H, J 4.5), 2.83 (d, 3H, J 4.5), 3.52 (t, 2H, J 5.5), 3.58 (s, 2H), 3.59 (t, 2H, J 5.5), 7.03 (d, 1H, J 5.0), 7.08 (q, 1H, J 4.5), 7.68 (br s, 2H), 7.99 (br s, 1H), 8.20 (s, 1H), 8.23 (br s, 1H), 9.34 (br s, 1H), 10.99 (br s, 1H). HRMS m/z 535.1840.

1-(5-(2-aminopyrimidin-4-yl)-4-methylthiazol-2-yl)-3-(4-((4-ethylpiperazin-1-yl)methyl)-3-(trifluoromethyl)phenyl)urea (62) Obtained by treating 5-(2-aminopyrimidin-4-yl)-4-methylthiazol-2-amine (100 mg, 483 µmol) and 4-((4-ethylpiperazin-1-yl)methyl)-3-(trifluoromethyl)aniline (138 mg, 483 µmol) according to the general synthetic procedure to produce a yellow solid (64.0 mg, 26%). $^1$H NMR (DMSO-d6) δ 0.98 (t, 3H, J 7.0), 2.31 (q, 2H, J 7.0), 2.38 (br s, 8H), 2.53 (s, 3H), 3.53 (s, 2H), 6.61 (br s, 2H), 6.78 (d, 1H, J 5.5), 7.66 (br s, 2H), 8.01 (br s, 1H), 8.22 (d, 1H, J 5.0), 9.34 (br s, 1H), 11.00 (br s, 1H). HRMS m/z 521.2058.

1-(5-(2-aminopyrimidin-4-yl)-4-methylthiazol-2-yl)-3-(4-((4-isopropylpiperazin-1-yl)methyl)-3-(trifluoromethyl)phenyl)urea (63) Obtained by treating 5-(2-aminopyrimidin-4-yl)-4-methylthiazol-2-amine (100 mg, 483 µmol) and 4-((4-isopropylpiperazin-1-yl)methyl)-3-(trifluoromethyl)aniline (145 mg, 483 µmol) according to the general synthetic procedure to produce a yellow solid (56.0 mg, 22%). $^1$H NMR (DMSO-d6) δ 0.96 (d, 6H, J 6.5), 2.38 (br s, 8H), 2.53 (s, 3H), 2.59-2.64 (m, 1H), 3.52 (s, 2H), 6.61 (br s, 2H), 6.78 (d, 1H, J 5.5), 7.66 (br s, 2H), 8.01 (br s, 1H), 8.22 (d, 1H, J 5.5), 9.37 (br s, 1H), 11.01 (br s, 1H). HRMS m/z 535.2205.

1-(5-(2-aminopyrimidin-4-yl)-4-methylthiazol-2-yl)-3-(4-(morpholinomethyl)-3-(trifluoromethyl)phenyl)urea (64) Obtained by treating 5-(2-aminopyrimidin-4-yl)-4-methylthiazol-2-amine (100 mg, 483 µmol) and 4-(morpholinomethyl)-3-(trifluoromethyl)aniline (125 mg, 483 µmol) according to the general synthetic procedure to produce a yellow solid (51.0 mg, 22%). $^1$H NMR (DMSO-d6) δ 2.38 (br s, 4H), 2.53 (s, 3H), 3.55 (s, 2H), 3.58 (t, 4H, J 4.5), 6.61 (br s, 2H), 6.78 (d, 1H, J 5.5), 7.68 (br s, 2H), 8.02 (br s, 1H), 8.22 (d, 1H, J 5.0), 9.33 (br s, 1H), 10.85 (br s, 1H). HRMS m/z 494.1583.

1-(5-(5-chloro-2-(methylamino)pyrimidin-4-yl)-4-methylthiazol-2-yl)-3-(4-((4-methylpiperazin-1-yl)methyl)-3-(trifluoromethyl)phenyl)urea (65) Obtained by treating 5-(5-chloro-2-(methylamino)pyrimidin-4-yl)-4-methylthiazol-2-amine (100 mg, 392 µmol) and 4-((4-methylpiperazin-1-yl)methyl)-3-(trifluoromethyl)aniline (107 mg, 392 µmol) according to the general synthetic procedure to produce a yellow solid (85.0 mg, 39%). $^1$H NMR (DMSO-d6) δ 2.16 (s, 3H), 2.37 (br s, 11H), 2.81 (d, 3H, J 5.0), 3.53 (s, 2H), 7.38 (q, 1H, J 5.0), 7.64-7.68 (m, 2H), 7.97 (br s, 1H), 8.35 (br s, 1H), 9.39 (br s, 1H), 11.11 (br s, 1H). HRMS m/z 555.1663.

1-(5-(5-chloro-2-(methylamino)pyrimidin-4-yl)-4-methylthiazol-2-yl)-3-(4-((4-ethylpiperazin-1-yl)methyl)-3-(trifluoromethyl)phenyl)urea (66) Obtained by treating 5-(5-chloro-2-(methylamino)pyrimidin-4-yl)-4-methylthiazol-2-amine (100 mg, 392 µmol) and 4-((4-ethylpiperazin-1-yl)methyl)-3-(trifluoromethyl)aniline (112 mg, 392 µmol) according to the general synthetic procedure to produce a yellow solid (110 mg, 50%). $^1$H NMR (DMSO-d6) δ 0.98 (t, 3H, J 7.0), 2.30-2.38 (m, 13H), 2.81 (d, 3H, J 4.5), 3.53 (s, 2H), 7.38 (q, 1H, J 5.0), 7.64-7.68 (m, 2H), 7.97 (br s, 1H), 8.35 (br s, 1H), 9.41 (br s, 1H), 11.09 (br s, 1H). HRMS m/z 569.1824.

1-(5-(5-chloro-2-(methylamino)pyrimidin-4-yl)-4-methylthiazol-2-yl)-3-(4-((4-isopropylpiperazin-1-yl)methyl)-3-(trifluoromethyl)phenyl)urea (67) Obtained by treating 5-(5-chloro-2-(methylamino)pyrimidin-4-yl)-4-methylthiazol-2-amine (100 mg, 392 µmol) and 4-((4-isopropylpiperazin-1-yl)methyl)-3-(trifluoromethyl)aniline (117 mg, 392 µmol) according to the general synthetic procedure to produce a yellow solid (65.0 mg, 29%). $^1$H NMR (DMSO-d6) δ 0.96 (d, 6H, 16.5), 2.45 (br s, 11H), 2.59-2.64 (m, 1H), 2.81 (d, 3H, J 5.0), 3.52 (s, 2H), 7.38 (q, 1H, J 5.0), 7.66 (br s, 2H), 7.97 (br s, 1H), 8.34 (br s, 1H), 9.38 (br s, 1H), 11.06 (br s, 1H). HRMS m/z 583.1983.

1-(4-((4-acetylpiperazin-1-yl)methyl)-3-(trifluoromethyl)phenyl)-3-(5-(5-chloro-2-(methylamino)pyrimidin-4-yl)-4-methylthiazol-2-yl)urea (68) Obtained by treating 5-(5-chloro-2-(methylamino)pyrimidin-4-yl)-4-methylthiazol-2-amine (100 mg, 392 µmol) and 1-(4-(4-amino-2-(trifluoromethyl)benzyl)piperazin-1-yl)ethan-1-one (117 mg, 392 µmol) according to the general synthetic procedure to produce a yellow solid (45.0 mg, 20%). $^1$H NMR (DMSO-d6) δ 1.98 (s, 3H), 2.32 (t, 2H, J 5.0), 2.38 (t, 2H, 0.5), 2.46 (s, 3H), 2.81 (d, 3H, J 4.5), 3.41-3.45 (m, 4H), 3.57 (s, 2H), 7.39 (q, 1H, J 5.0), 7.67-7.70 (m, 2H), 7.98 (br s, 1H), 8.35 (br s, 1H), 9.35 (br s, 1H), 10.89 (br s, 1H). HRMS m/z 583.1618.

1-(5-(5-chloro-2-(methylamino)pyrimidin-4-yl)-4-methylthiazol-2-yl)-3-(4-((4-(methylsulfonyl)piperazin-1-yl)methyl)-3-(trifluoromethyl)phenyl)urea (69) Obtained by treating 5-(5-chloro-2-(methylamino)pyrimidin-4-yl)-4- methylthiazol-2-amine (100 mg, 392 µmol) and 4-((4-(methylsulfonyl)piperazin-1-yl)methyl)-3-(trifluoromethyl)aniline (131 mg, 392 µmol) according to the general synthetic procedure to produce a yellow solid (70.0 mg, 29%). $^1$H NMR (DMSO-d6) 2.48 (br s, 7H), 2.81 (d, 3H, 14.5), 2.88 (s, 3H), 3.12-3.18 (m, 4H), 3.61 (s, 2H), 7.39 (q, 1H, 15.0), 7.65-7.70 (m, 2H$_1$), 7.98 (br s, 1H), 8.35 (br s, 1H), 9.35 (br s, 1H), 10.89 (br s, 1H). HRMS m/z 619.1289.

1-(5-(5-fluoro-2-(methylamino)pyrimidin-4-yl)-4-methylthiazol-2-yl)-3-(4-(morpholinomethyl)-3-(trifluoromethyl)phenyl)urea (70) Obtained by treating 5-(5-fluoro-2-(methylamino)pyrimidin-4-yl)-4-methylthiazol-2-amine (174 mg, 728 µmol) and 4-(morpholinomethyl)-3-(trifluoromethyl)aniline (189 mg, 728 µmol) according to the general synthetic procedure to produce a yellow solid (186 mg, 48%). $^1$H NMR (DMSO-d6) δ 2.37 (br s, 4H), 2.57 (s, 3H), 2.81 (d, 3H, J 5.0), 3.55 (s, 2H), 3.58 (t, 4H, J 4.5), 7.14 (q, 1H, J 5.0), 7.68 (br s, 2H), 7.98 (br s, 1H), 8.35 (d, 1H, J 4.5), 9.34 (br s, 1H), 10.94 (br s, 1H). HRMS m/z 526.1644.

1-(5-(5-cyano-2-(methylamino)pyrimidin-4-yl)-4-methylthiazol-2-yl)-3-(4-((4-methylpiperazin-1-yl)methyl)-3-(trifluoromethyl)phenyl)urea (71) Obtained by treating 4-(2-amino-4-methylthiazol-5-yl)-2-(methylamino)pyrimidine-5-carbonitrile (100 mg, 406 µmol) and 4-((4-methylpiperazin-1-yl)methyl)-3-(trifluoromethyl)aniline (112 mg, 406 µmol) according to the general synthetic procedure to produce a yellow solid (97.0 mg, 43%). $^1$H NMR (DMSO-d6) δ 2.17 (s, 3H), 2.38 (br s, 8H), 2.47 (d, 3H, J 38.5), 2.89 (d, 3H, J 5.0), 3.54 (s, 2H), 7.64-7.69 (m, 2H), 7.96 (dd, 1H, J 9.0 & 2.0), 8.22 (q, 1H, J 5.0), 8.70 (d, 1H, J 64.5), 9.40 (br s, 1H), 11.20 (br s, 1H). HRMS m/z 546.2009.

1-(5-(5-cyano-2-(methylamino)pyrimidin-4-yl)-4-methylthiazol-2-yl)-3-(4-((4-ethylpiperazin-1-yl)methyl)-3-(trifluoromethyl)phenyl)urea (72) Obtained by treating 4-(2-amino-4-methylthiazol-5-yl)-2-(methylamino)pyrimidine-5-carbonitrile (100 mg, 406 µmol) and 4-((4-ethylpiperazin-1-yl)methyl)-3-(trifluoromethyl)aniline (117 mg, 406 mol) according to the general synthetic procedure to produce a yellowish white solid (85.0 mg, 37%). $^1$H NMR (DMSO-d6) δ 0.98 (t, 3H, J 7.5), 2.33 (q, 2H, 0.7.5), 2.39 (br s, 8H), 2.47 (d, 3H, J 38.5), 2.89 (d, 3H, 15.0), 3.54 (s, 2H), 7.67-7.73 (m, 2H), 7.96 (dd, 1H, J 9.0 & 2.0), 8.21 (q, 1H, J 4.5), 8.70 (d, 1H, J 64.5), 9.40 (br s, 1H), 11.17 (br s, 1H). HRMS m/z 560.2163.

1-(5-(5-cyano-2-(methylamino)pyrimidin-4-yl)-4-methylthiazol-2-yl)-3-(4-((4-isopropylpiperazin-1-yl)methyl)-3-(trifluoromethyl)phenyl)urea (73) Obtained by treating 4-(2-amino-4-methylthiazol-5-yl)-2-(methylamino)pyrimidine-5-carbonitrile (100 mg, 406 µmol) and 4-((4-isopropylpiperazin-1-yl)methyl)-3-(trifluoromethyl)aniline (123 mg, 406 µmol) according to the general synthetic procedure to produce a yellow solid (113 mg, 48%). $^1$H NMR (DMSO-d6) δ 0.97 (d, 6H, J 6.5), 2.39 (br s, 8H), 2.47 (d, 3H, J 38.5), 2.64-2.66 (m, 1H), 2.89 (d, 3H, J 5.0), 3.53 (s, 2H), 7.67-7.71 (m, 2H), 7.96 (dd, 1H, J 9.0 & 2.0), 8.22 (q, 1H, J 5.0), 8.70 (d, 1H, J 64.5), 9.42 (br s, 1H), 11.11 (br s, 1H). HRMS m/z 574.2316.

1-(5-(5-cyano-2-(methylamino)pyrimidin-4-yl)-4-methylthiazol-2-yl)-3-(4-((4-(methylsulfonyl)piperazin-1-yl)methyl)-3-(trifluoromethyl)phenyl)urea (74) Obtained by treating 4-(2-amino-4-methylthiazol-5-yl)-2-(methylamino)pyrimidine-5-carbonitrile (100 mg, 406 µmol) and 4-((4-(methylsulfonyl)piperazin-1-yl)methyl)-3-(trifluoromethyl)aniline (138 mg, 406 µmol) according to the general synthetic procedure to produce a yellow solid (114 mg, 46%). $^1$H NMR (DMSO-d6) δ 2.48 (d, 3H, J 38.5), 2.49 (t, 4H, J 5.5), 2.89 (br s, 6H), 3.13 (t, 4H, J 5.0), 3.62 (s, 2H), 7.66-7.71 (m, 2H), 7.97 (d, 1H, J 9.0), 8.23 (q, 1H, J 5.0), 8.71 (d, 1H, J 63.5), 9.39 (br s, 1H), 11.05 (br s, 1H). HRMS m 610.1625.

1-(5-(5-cyano-2-(methylamino)pyrimidin-4-yl)-4-methylthiazol-2-yl)-3-(4-(morpholinomethyl)-3-(trifluoromethyl)phenyl)urea (75) Obtained by treating 4-(2-amino-4-methylthiazol-5-yl)-2-(methylamino)pyrimidine-5-carbonitrile (100 mg, 406 µmol) and 4-(morpholinomethyl)-3-(trifluoromethyl)aniline (107 mg, 406 µmol) according to the general synthetic procedure to produce a yellowish white solid (76.0 mg, 35%). $^1$H NMR (DMSO-d6) δ 2.37 (br s, 4H), 2.47 (d, 3H, J 38.0), 2.89 (d, 3H, J 5.0), 3.55 (s, 2H), 3.58 (t, 4H, J 4.0), 7.69 (br s, 2H), 7.97 (d, 1H, J 9.5), 8.23 (q, 1H, J 4.5), 8.71 (d, 1H, J 63.0), 9.37 (br s, 1H), 11.03 (br s, 1H). HRMS m/z 533.1696.

1-(5-(2-isopropylpyrimidin-4-yl)-4-methylthiazol-2-yl)-3-(4-((4-methylpiperazin-1-yl)methyl)-3-(trifluoromethyl)phenyl)urea (76) Obtained by treating 5-(2-isopropylpyrimidin-4-yl)-4-methylthiazol-2-amine (100 mg, 427 µmol) and 4-((4-methylpiperazin-1-yl)methyl)-3-(trifluoromethyl)aniline (117 mg, 427 µmol) according to the general synthetic procedure to produce a yellow solid yellow solid (135 mg, 59%). $^1$H NMR (DMSO-d6) δ 1.30 (d, 6H, J 7.0), 2.20 (s, 3H), 2.39 (br s, 8H), 2.60 (s, 3H), 3.06-3.14 (m, 1H), 3.54 (s, 2H), 7.45 (d, 1H, J 5.5), 7.66 (br s, 2H), 7.99 (br s, 1H), 8.66 (d, 1H, J 5.5), 9.43 (br s, 1H), 11.07 (br s, 1H). HRMS m/z 534.2258.

1-(4-((4-acetylpiperazin-1-yl)methyl)-3-(trifluoromethyl)phenyl)-3-(5-(2-isopropylpyrimidin-4-yl)-4-methylthiazol-2-yl)urea (77) Obtained by treating 5-(2-isopropylpyrimidin-4-yl)-4-methylthiazol-2-amine (100 mg, 427 µmol) and 1-(4-(4-amino-2-(trifluoromethyl)benzyl)piperazin-1-yl)ethan-1-one (129 mg, 427 µmol) according to the general synthetic procedure to produce a yellow solid (80.0 mg, 33%). $^1$H NMR (DMSO-d6) δ 1.30 (d, 6H, J 7.0), 1.98 (s, 3H), 2.32 (t, 2H, J 5.0), 2.38 (t, 2H, J 4.5), 2.60 (s, 3H), 3.06-3.14 (m, 1H), 3.42 (t, 4H, J 5.5), 3.58 (s, 2H), 7.45 (d, 1H, J 15.5), 7.69 (br s, 2H), 8.01 (s, 1H), 8.67 (d, 1H, J 5.5), 9.38 (br s, 1H), 10.98 (br s, 1H). HRMS m/z 562.2215.

1-(5-(2-isopropylpyrimidin-4-yl)-4-methylthiazol-2-yl)-3-(4-((4-(methylsulfonyl)-piperazin-1-yl)methyl)-3-(trifluoromethyl)phenyl)urea (78) Obtained by treating 5-(2-isopropylpyrimidin-4-yl)-4-methylthiazol-2-amine (100 mg, 427 µmol) and 4-((4-(methylsulfonyl)piperazin-1-yl)methyl)-3-(trifluoromethyl)aniline (144 mg, 427 µmol) according to the general synthetic procedure to produce a yellow solid (112 mg, 44%). $^1$H NMR (DMSO-d6) δ 1.30 (d, 6H, J 7.0), 2.48 (br s, 4H), 2.60 (s, 3H), 2.88 (s, 3H), 3.07-3.13 (m, 5H), 3.62 (s, 2H), 7.45 (d, 1H, J 5.5), 7.67 (br s, 2H), 8.01 (br s, 1H), 8.67 (d, 1H, J 5.0), 9.36 (br s, 1H), 10.91 (br s, 1H). HRMS m/z 598.1876.

1-(5-(2-isopropylpyrimidin-4-yl)-4-methylthiazol-2-yl)-3-(4-(morpholinomethyl)-3-(trifluoromethyl)phenyl)urea (79) Obtained by treating 5-(2-isopropylpyrimidin-4-yl)-4-methylthiazol-2-amine (100 mg, 427 µmol) and 4-(morpholinomethyl)-3-(trifluoromethyl)aniline (112 mg, 427 µmol) according to the general synthetic procedure to produce a yellow solid (65.0 mg, 29%). $^1$H NMR (DMSO-d6) δ 1.30 (d, 6H, J 7.0), 2.37 (br s, 4H), 2.60 (s, 3H), 3.06-3.14 (m, 1H), 3.55 (s, 2H), 3.59 (t, 4H, J 4.5), 7.45 (d, 1H, J 5.5), 7.68 (br s, 2H), 8.01 (br s, 1H), 8.67 (d, 1H, J 5.5), 9.35 (br s, 1H), 10.95 (br s, 1H). HRMS m/z 521.1944.

1-(4-methyl-5-(2-(methylthio)pyrimidin-4-yl)thiazol-2-yl)-3-(4-((4-methyl-piperazin-1-yl)methyl)-3-(trifluoromethyl)phenyl)urea (80) Obtained by treating 4-methyl-5-(2-

(methylthio)pyrimidin-4-yl)thiazol-2-amine (100 mg, 420 µmol) and 4-((4-methylpiperazin-1-yl)methyl)-3-(trifluoromethyl)aniline (114 mg, 420 µmol) according to the general synthetic procedure to produce a yellow solid (51.0 mg, 23%). $^1$H NMR (DMSO-d6) δ 2.17 (s, 3H), 2.38 (br s, 8H), 2.54 (s, 3H), 2.59 (s, 3H), 3.54 (s, 2H), 7.32 (d, 1H, J 5.5), 7.64-7.68 (m, 2H), 7.98 (d, J 2.0, 1H), 8.53 (d, 1H, J 5.5), 9.41 (br s, 1H), 11.16 (br s, 1H). HRMS m/z 538.1661.

1-(4-((4-acetylpiperazin-1-yl)methyl)-3-(trifluoromethyl)phenyl)-3-(4-methyl-5-(2-(methylthio)pyrimidin-4-yl)thiazol-2-yl)urea (81) Obtained by treating 4-methyl-5-(2-(methylthio)pyrimidin-4-yl)thiazol-2-amine (100 mg, 420 mol) and 1-(4-(4-amino-2-(trifluoromethyl)benzyl)piperazin-1-yl)ethan-1-one (126 mg, 420 µmol) according to the general synthetic procedure to produce a yellow solid (155 mg, 65%). $^1$H NMR (DMSO-d6) δ 1.98 (s, 3H), 2.32 (t, 2H, J 5.0), 2.38 (t, 2H, J 5.0), 2.54 (s, 3H), 2.59 (s, 3H), 3.43 (t, 4H, J 6.0), 3.58 (s, 2H), 7.34 (d, 1H, J 5.5), 7.68 (br s, 2H), 7.99 (br s, 1H), 8.55 (d, 1H, J 5.0), 9.37 (br s, 1H), 11.00 (br s, 1H). HRMS m 566.1619.

1-(4-methyl-5-(2-(methylthio)pyrimidin-4-yl)thiazol-2-yl)-3-(4-((4-(methyl-sulfonyl)piperazin-1-yl)methyl)-3-(trifluoromethyl)phenyl)urea (82) Obtained by treating 4-methyl-5-(2-(methylthio)pyrimidin-4-yl)thiazol-2-amine (100 mg, 420 µmol) and 4-((4-(methylsulfonyl)piperazin-1-yl)methyl)-3-(trifluoromethyl)aniline (142 mg, 420 µmol) according to the general synthetic procedure to produce a yellow solid (64.0 mg, 26%). $^1$H NMR (DMSO-d6) δ 2.48 (t, 4H, J 6.0), 2.54 (s, 3H), 2.59 (s, 3H), 2.88 (s, 3H), 3.12 (br s, 4H), 3.62 (s, 2H), 7.33 (d, 1H, J 5.5), 7.66-7.71 (m, 2H), 7.99 (br s, 1H), 8.54 (d, 1H, J 5.5), 9.49 (br s, 1H), 11.36 (br s, 1H). HRMS m/z 602.1291.

1-(4-methyl-5-(2-(methylthio)pyrimidin-4-yl)thiazol-2-yl)-3-(4-(morpholino-methyl)-3-(trifluoromethyl)phenyl)urea (83) Obtained by treating 4-methyl-5-(2-(methylthio)pyrimidin-4-yl)thiazol-2-amine (100 mg, 420 µmol) and 4-(morpholinomethyl)-3-(trifluoromethyl)aniline (109 mg, 420 µmol) according to the general synthetic procedure to produce a yellow solid yellow solid (70.0 mg, 32%). $^1$H NMR (DMSO-d6) δ 2.37 (br s, 4H), 2.54 (s, 3H), 2.59 (s, 3H), 3.55 (s, 2H), 3.58 (t, 4H, J 4.5), 7.33 (d, 1H. J 5.5), 7.68 (br s, 2H), 7.99 (br s, 1H), 8.54 (d, 1H, J 5.0), 9.35 (br s, 1H), 11.02 (br s, 1H). HRMS m/z 525.1345.

Example 2 Biological Activity

Kinase Assays

The kinase activity of CDK8/CycC was measured using a radiometric protein kinase assay (33PanQinase® Activity Assay) by ProQinase GmbH, Freiburg, Germany, with the protocols shown at www.proqinase.com/sites/default/files/public/uploads/WildtypeProfiler/radiometric_assay_v05_2012_manual.pdf. IC$_{50}$ determination (8.3 nM with 1.0 µM ATP and 1.0 µg/50 µL of substrate RBER-IRStide) was performed as duplicate measurements and calculated using Quattro Workflow V3.1.1 (Quattro Research GmbH, Germany). Apparent inhibition constants (K$_i$) values were calculated from K$_m$ (ATP) and IC$_{50}$ values for the respective kinases. The results are shown in Table 2.

Cell Viability Assay

Compounds from Example 1 may be subjected to a standard MTT (3-(4,5-dimethylthiazol-2-yl)-2,5-diphenyltetrazolium bromide) and resazurin assays on solid tumour cell lines and leukemia cell lines, respectively, as previously reported (Wang S et al., *J Med Chem* 47:1662-1675, 2004 and Diab S e al. *CheMedChem* 9:962-972, 2014). Compound concentrations required to inhibit 50% of cell growth (GI$_{50}$) can be calculated using non-linear regression analysis. The results of example compounds are shown in Table 2.

TABLE 2

Biological activity of compounds of the present invention

| Compound | CDK8 Kinase inhibition IC$_{50}$ (µM) | 72 h growth inhibition GI$_{50}$ (µM) | |
|---|---|---|---|
| | | MV-4-11 | HCT-116 |
| 1 | 0.036 | 0.639 ± 0.12 | 1.511 ± 0.06 |
| 2 | 1.360 | — | — |
| 3 | 0.042 | 0.952 ± 0.20 | 1.586 ± 0.06 |
| 4 | 0.049 | 0.457 ± 0.18 | 0.537 ± 0.14 |
| 5 | 0.025 | 3.810 ± 0.58 | 7.104 ± 0.96 |
| 6 | 0.233 | — | — |
| 7 | 2.300 | — | — |
| 8 | 0.065 | — | — |
| 9 | 0.041 | 0.526 ± 0.04 | 0.519 ± 0.16 |
| 10 | 0.010 | 0.870 ± 0.36 | 0.510 ± 0.03 |
| 11 | 0.033 | 1.481 ± 1.32 | 0.693 ± 0.03 |
| 12 | 0.007 | 2.113 ± 1.64 | 6.405 ± 0.27 |
| 13 | 0.006 | 3.903 ± 1.10 | 2.770 ± 0.21 |
| 14 | 0.010 | 0.585 ± 0.03 | 5.079 ± 0.82 |
| 15 | 0.008 | 0.565 ± 0.04 | 6.253 ± 0.61 |
| 16 | 0.009 | 2.273 ± 0.68 | — |
| 17 | 0.015 | 3.506 ± 0.79 | 5.972 ± 0.723 |
| 18 | 0.025 | 4.996 ± 0.63 | 4.293 ± 0.523 |
| 19 | 0.006 | — | 0.854 ± 0.01 |
| 20 | 0.006 | 0.939 ± 0.06 | 4.531 ± 0.98 |
| 21 | 0.009 | 3.348 ± 0.19 | 6.132 ± 0.91 |
| 22 | 0.020 | 4.634 ± 1.56 | 4.307 ± 0.75 |
| 23 | 0.026 | 3.168 ± 0.53 | 4.955 ± 0.12 |
| 24 | 0.012 | 3.478 ± 9.53 | 7.252 ± 0.31 |
| 25 | 0.013 | 2.232 ± 0.14 | 5.852 ± 1.14 |
| 26 | 0.015 | 2.564 ± 0.49 | 5.099 ± 0.66 |
| 27 | 0.053 | 4.157 ± 0.80 | 5.641 ± 0.32 |
| 28 | 0.026 | 3.278 ± 0.64 | 0.772 ± 0.25 |
| 29 | 0.013 | 2.160 ± 1.17 | 7.774 ± 0.43 |
| 30 | 0.008 | 4.389 ± 1.02 | 2.346 ± 3.21 |
| 31 | 0.022 | 0.945 ± 0.05 | 6.833 ± 1.01 |
| 32 | 0.012 | <0.001 | 0.366 ± 0.09 |
| 33 | 0.010 | <0.001 | 0.457 ± 0.03 |
| 34 | 0.011 | <0.001 | — |
| 35 | 0.014 | 0.085 ± 0.00 | — |
| 36 | 0.032 | 0.076 ± 0.01 | — |
| 37 | 0.009 | 0.068 ± 0.03 | 7.845 ± 0.39 |
| 38 | — | 0.994 ± 0.13 | — |
| 39 | 0.008 | 0.096 ± 0.00 | — |
| 40 | 0.034 | 2.512 ± 0.39 | — |
| 41 | 0.019 | — | — |
| 42 | — | — | — |
| 43 | 0.009 | 1.523 ± 0.80 | 5.959 ± 0.44 |
| 44 | 0.007 | 2.605 ± 0.46 | 2.374 ± 0.05 |
| 45 | 0.011 | 0.756 ± 0.12 | 3.044 ± 0.53 |
| 46 | 0.041 | 5.495 ± 0.49 | 35.022 ± 11.82 |
| 47 | 0.038 | 5.278 ± 0.15 | 5.769 ± 0.42 |
| 48 | 0.046 | 5.913 ± 0.18 | 8.337 ± 0.60 |
| 49 | 0.082 | <0.001 | — |
| 50 | 0.202 | 0.612 ± 0.06 | — |
| 51 | 0.060 | 5.714 ± 0.59 | 4.323 ± 0.41 |
| 52 | 0.015 | <0.001 | — |
| 53 | 0.090 | <0.001 | — |
| 54 | 0.016 | <0.001 | — |
| 55 | 0.035 | 0.214 ± 0.12 | — |
| 56 | 0.021 | 0.529 ± 0.12 | — |
| 57 | 0.049 | 6.158 ± 0.14 | — |
| 58 | 0.007 | 0.001 ± 0.00 | — |
| 59 | 0.012 | 0.001 ± 0.00 | — |
| 60 | 0.016 | 0.007 ± 0.00 | — |
| 61 | 0.020 | 0.176 ± 0.04 | — |
| 62 | 0.014 | 0.001 ± 0.00 | — |
| 63 | 0.013 | 0.003 ± 0.00 | — |
| 64 | 0.015 | 0.275 ± 0.05 | — |
| 65 | 0.015 | 0.055 ± 0.01 | — |
| 66 | 0.021 | 0.073 ± 0.03 | — |
| 67 | 0.030 | 0.174 ± 0.01 | — |
| 68 | 0.080 | 4.250 ± 0.42 | — |

TABLE 2-continued

Biological activity of compounds of the present invention

| Compound | CDK8 Kinase inhibition IC$_{50}$ (µM) | 72 h growth inhibition GI$_{50}$ (µM) | |
|---|---|---|---|
| | | MV-4-11 | HCT-116 |
| 69 | 0.132 | 4.691 ± 0.42 | — |
| 70 | 0.025 | 0.273 ± 0.01 | — |
| 71 | 0.050 | 0.200 ± 0.02 | — |
| 72 | 0.064 | 0.432 ± 0.01 | — |
| 73 | 0.059 | 0.482 ± 0.03 | — |
| 74 | 0.272 | 3.254 ± 0.35 | — |
| 75 | 0.082 | 3.417 ± 0.23 | — |
| 76 | 0.074 | <0.001 | — |
| 77 | 0.169 | 0.712 ± 0.02 | — |
| 78 | 0.293 | 1.590 ± 0.09 | — |
| 79 | 0.206 | 0.998 ± 0.06 | — |
| 80 | 0.079 | 0.001 ± 0.00 | — |
| 81 | 0.177 | 0.715 ± 0.01 | — |
| 82 | 0.220 | 0.721 ± 0.03 | — |
| 83 | 0.121 | 1.556 ± 0.10 | — |

Throughout the specification and the claims that follow, unless the context requires otherwise, the words "comprise" and "include" and variations such as "comprising" and "including" will be understood to imply the inclusion of a stated integer or group of integers, but not the exclusion of any other integer or group of integers.

The reference to any prior art in this specification is not, and should not betaken as, an acknowledgement of any form of suggestion that such prior art forms part of the common general knowledge.

It will be appreciated by those skilled in the art that the invention is not restricted in its use to the particular application described. Neither is the present invention restricted in its preferred embodiment with regard to the particular elements and/or features described or depicted herein. It will be appreciated that the invention is not limited to the embodiment or embodiments disclosed, but is capable of numerous rearrangements, modifications and substitutions without departing from the scope of the invention as set forth and defined by the following claims.

The invention claimed is:

1. A compound of formula I:

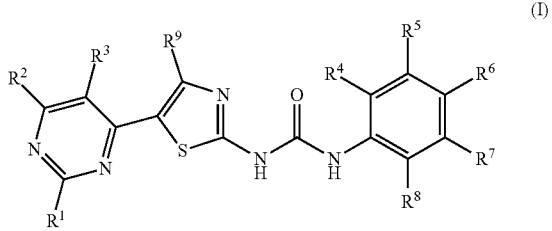

(I)

wherein:

$R^1$, $R^2$, $R^3$, $R^4$, $R^5$, $R^6$, $R^7$, $R^8$ and $R^9$ are each independently selected from the group consisting of H, alkyl, alkyl-$R^{10}$, aralkyl, aralkyl-$R^{10}$, heteroalkyl, cycloalkyl, heterocycloalkyl, aryl, aryl-$R^{10}$, heteroaryl, halogen, NO$_2$, CHO, CN, CHF$_2$, CF$_3$, OH, O—CHF$_2$, O—CF$_3$, O-alkyl, O-alkyl-$R^{10}$, O-heteroalkyl, O-cycloalkyl, O-heterocycloalkyl, O-aryl, O-heteroaryl, O—$R^{10}$, NH$_2$, NH-alkyl, NH-alkyl-$R^{10}$, NH-heteroalkyl, NH-cycloalkyl, NH-heterocycloalkyl, NH-aryl, NH-heteroaryl, NH—$R^{10}$, N-(alkyl)$_2$, N-(heteroalkyl)$_2$, N-(cycloalkyl)$_2$, N-(heterocycloalkyl)$_2$, N-(aryl)$_2$, N-(heteroaryl)$_2$, N—($R^{10}$)($R^{11}$), N-(alkyl)($R^{10}$), N-(alkyl)(aryl), N-(heteroalkyl)($R^{10}$), N-(cycloalkyl)($R^{10}$), N-(heterocycloalkyl)($R^{10}$), N-(aryl)($R^{10}$), N-(heteroaryl)($R^{10}$), SH-alkyl, SH-alkyl-$R^{10}$, SH-heteroalkyl, SH-cycloalkyl, SH-heterocycloalkyl, SH-aryl, SH-heteroaryl, S-(alkyl)$_2$, S-heteroalkyl, S—C$_{1-6}$ alkyl, S—CF$_3$, SO$_2$CF$_3$, S-(cycloalkyl)$_2$, S-(heterocycloalkyl)$_2$, S-(aryl)$_2$, S-(heteroaryl)$_2$, S-(alkyl)(aryl), SH—$R^{10}$, S—($R^{10}$)($R^{11}$), S-(alkyl)($R^{10}$), S-(heteroaryl)($R^{10}$), S-(cycloalkyl)($R^{10}$), S-(heterocycloalkyl)($R^{10}$), S-(aryl)($R^{10}$), S-(heteroaryl)($R^{10}$), COOH, CONH$_2$, CONH-alkyl, CONH-aryl, CON-(alkyl)($R^{10}$), CON(aryl)($R^{10}$), CON(heteroaryl)($R^{10}$) CONH—$R^{10}$, CON—($R^{10}$)($R^{11}$), SO$_3$H, SO$_2$-alkyl, SO$_2$-alkyl-$R^{10}$, SO$_2$-aryl, SO$_2$-aryl-$R^{10}$, SO$_2$NH$_2$, SO$_2$NH—$R^{10}$, SO$_2$N—($R^{10}$)($R^{11}$), CO-alkyl, CO-alkyl-$R^{10}$, CO-aryl, CO-aryl-$R^{10}$, CO—$R^{10}$, COOR$^{10}$, and $R^{12}$, and wherein $R^{10}$ and $R^{11}$ are each independently selected from the group consisting of H, alkyl, alkyl-$R^{13}$, heteroalkyl, cycloalkyl, heterocycloalkyl, aryl, heteroaryl, halogen, NO$_2$, CN, CF$_3$, OH, O-alkyl, O-alkyl-$R^{13}$, O-heteroalkyl, O-cycloalkyl, O-heterocycloalkyl, O-aryl, O-heteroaryl, O—$R^{13}$, NH$_2$, NH-alkyl, NH-alkyl-$R^{13}$, NH-heteroalkyl, NH-cycloalkyl, NH-heterocycloalkyl, NH-aryl, NH-heteroaryl, NH—$R^{13}$, N-(alkyl)$_2$, N-(heteroalkyl)$_2$, N-(cycloalkyl)$_2$, N-(heterocycloalkyl)$_2$, N-(aryl)$_2$, N-(heteroaryl)$_2$, N—($R^{13}$)($R^{14}$), N-(alkyl)($R^{13}$), N-(heteroalkyl)($R^{13}$), N-(cycloalkyl)($R^{13}$), N-(heterocycloalkyl)($R^{13}$), N-(aryl)($R^{13}$), N-(heteroaryl)($R^{13}$), SH-alkyl, SH-alkyl-$R^{13}$, SH-heteroalkyl, SH-cycloalkyl, SH-heterocycloalkyl, SH-aryl, SH-heteroaryl, S-(alkyl)$_2$, S-(cycloalkyl)$_2$, S-(heterocycloalkyl)$_2$, S-(aryl)$_2$, S-(heteroaryl)$_2$, S-(alkyl)(aryl), SH—$R^{13}$, S—($R^{13}$)($R^{14}$), S-(alkyl)($R^{13}$), S-(heteroaryl)($R^{13}$), S-(cycloalkyl)($R^{13}$), S-(heterocycloalkyl)($R^{13}$), S-(aryl)($R^{13}$), S-(heteroaryl)($R^{13}$), COOH, COO-alkyl, CONH$_2$, CONH-alkyl, CONH-aryl, CON-(alkyl)($R^{13}$), CON(aryl)($R^{13}$), CON(heteroaryl)($R^{13}$), CONH—$R^{13}$, CON—($R^{13}$)($R^{14}$), SO$_3$H, SO$_2$-alkyl, SO$_2$-alkyl-$R^{13}$, SO$_2$-aryl, SO$_2$-aryl-$R^{13}$, SO$_2$NH$_2$, SO$_2$NH—$R^{13}$, SO$_2$N—($R^{13}$)($R^{14}$), CO-alkyl, CO-alkyl-$R^{13}$, CO-aryl, CO-aryl-$R^{13}$, CO—$R^{13}$, COOR$^{13}$, and $R^{12}$, and wherein said heterocycloalkyl and heteroaryl groups comprise at least one but no more than two heteroatoms selected from N, S and O, and wherein said alkyl, heteroalkyl, cycloalkyl, heterocycloalkyl, aralkyl, aryl and heteroaryl groups may be optionally substituted with one or more groups selected from halogen, CN, OH, O-methyl, C$_{1-6}$ alkyl, NH$_2$, N—(C$_{1-6}$ alkyl)$_2$, COOH, CO—C$_{1-6}$ alkyl, CONH$_2$, SO$_2$—C$_{1-6}$ alkyl, CF$_3$; and $R^{12}$, $R^{13}$ and $R^{14}$ are independently selected from water solubilising groups;

or a pharmaceutically acceptable salt or solvate thereof;

and wherein the compound is not N-[5-(2-methyl-4-pyrimidinyl)-4-(3-methylphenyl)-1,3-thiazol-2-yl]-N'-phenylurea.

2. A compound according to claim 1, wherein $R^1$, $R^2$, $R^3$, $R^4$, $R^5$, $R^6$, $R^7$, $R^8$ and $R^9$ are each independently selected from the group consisting of H, alkyl, alkyl-$R^{10}$, cycloalkyl, heterocycloalkyl, aryl, heteroaryl, halogen, NO$_2$, CHF$_2$, CF$_3$, CHO, CN, OH, O—CHF$_2$, O—CF$_3$, O-alkyl, O-heteroalkyl, O—C$_{3-8}$ cycloalkyl, O-aryl, O-heteroaryl, NH$_2$, NH-alkyl, NH-heteroalkyl, NH-cycloalkyl, NH-heterocy cloalkyl, NH-aryl, NH-heteroaryl, N(alkyl)$_2$, N(cycloalkyl)$_2$, N(heterocycloalkyl)$_2$, N-(alkyl)(aryl), SH-alkyl, SH-aryl, SH-heteroaryl, S-heteroalkyl, S—C$_{1-6}$ alkyl, S—CF$_3$, SO$_2$CF$_3$, S—(C$_{3-8}$ cycloalkyl)$_2$, and R$^{12}$.

3. A compound according to claim 1, wherein R$^1$ is CH(C$_{1-6}$ alkyl)$_2$, NH$_2$, NH—C$_{1-6}$ alkyl or N(C$_{1-6}$ alkyl)$_2$, or S—C$_{1-6}$ alkyl.

4. A compound according to claim 1, wherein any one or more of R$^2$, R$^3$ and R$^4$ is H.

5. A compound according to claim 1, wherein R$^3$ is H, halogen or CN.

6. A compound according to claim 1, wherein R$^5$ is selected from H, NH$_2$, C$_{1-6}$ alkyl, halogen, O—C$_{1-3}$ alkyl, CHF$_2$, CF$_3$ and CHO.

7. A compound according to claim 1, wherein R$^5$ is selected from H and CF$_3$.

8. A compound according to claim 1, wherein R$^6$ is selected from H, NH$_2$, C$_{1-6}$ alkyl, halogen, O—C$_{1-3}$ alkyl, CHF$_2$, CF$_3$ and CHO.

9. A compound according to claim 1, wherein R$^6$ is selected from:

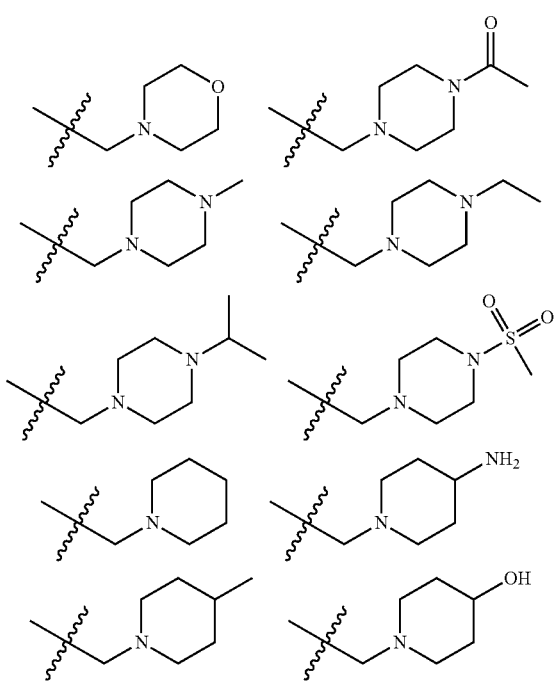

-continued

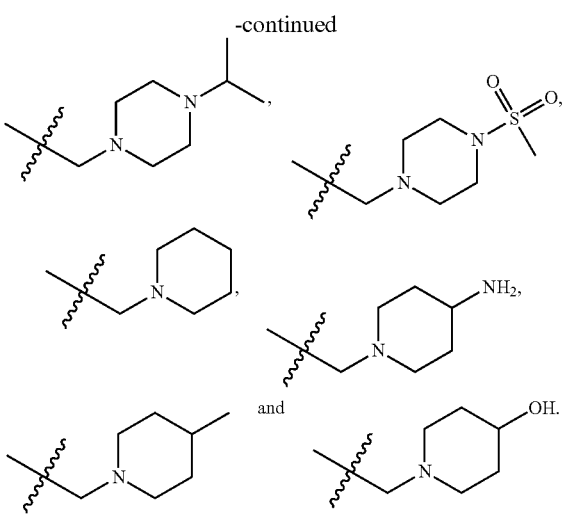

10. A compound according to claim 1, wherein R$^7$ is selected from H, NH$_2$, NO$_2$, C$_{1-6}$ alkyl, halogen, O—C$_{1-3}$ alkyl, CHF$_2$, O—CHF$_2$, CF$_3$, O—CF$_3$, S—C$_{1-3}$ alkyl, SCF$_3$, SO$_2$CF$_3$, CN and CHO.

11. A compound according to claim 1, wherein R$^8$ is selected from H, NH$_2$, C$_{1-6}$ alkyl, halogen, O—C$_{1-3}$ alkyl, CHF$_2$, CF$_3$ and CHO.

12. A compound according to claim 1, wherein R$^9$ is selected from H, NH$_2$, C$_{1-6}$ alkyl, halogen, O—C$_{1-3}$ alkyl, CHF$_2$, CF$_3$ and CHO.

13. A compound according to claim 1, wherein R$^9$ is H or a C$_{1-6}$ alkyl.

14. A compound according to claim 1, wherein any one or more of R$^2$, R$^4$ and R$^8$ is H.

15. A method of treating cancer or another proliferative cell disease or condition in a subject, the method comprising administering to said subject a therapeutically effective amount of a compound according to claim 1 or a pharmaceutically acceptable salt or solvate thereof, optionally in combination with a pharmaceutically acceptable carrier, diluent and/or excipient, wherein the cancer or proliferative cell disease is colorectal cancer, biliary tract cancer, brain cancer, breast cancer, cervical cancer, choriocarcinoma, endometrial cancer, oesophageal cancer, gastric cancer, haematological neoplasm, intraepithelial neoplasm, liver cancer, lung cancer, lymphoma, neuroblastoma, oral cancer, squamous cell carcinoma, ovarian cancer, pancreatic cancer, prostate cancer, colorectal cancer, sarcoma, skin cancer, testicular cancer, stromal tumour, germ cell tumour, thyroid cancer, and renal cancer.

16. A pharmaceutical composition or medicament comprising a compound according to claim 1 and a pharmaceutically acceptable carrier, diluent and/or excipient.

17. A method for modulating protein kinase activity in a cell, comprising introducing to or contacting said cell with an effective amount of a compound according to claim 1 or a pharmaceutically acceptable salt or solvate.

18. A method of treating a disease or condition in a subject characterised by over-expression of CDK8 and/one or more aberrant CDK8 activity, the method comprising administering to said subject a therapeutically effective amount of a compound according to claim 1 or a pharmaceutically acceptable salt or solvate thereof, optionally in combination with a pharmaceutically acceptable carrier, diluent and/or excipient, wherein the disease or condition in a subject characterised by over-expression of CDK8 and/one or more aberrant CDK8 activity is colorectal cancer, biliary tract cancer, brain cancer, breast cancer, cervical cancer, choriocarcinoma, endometrial cancer, oesophageal cancer, gastric cancer, haematological neoplasm, intraepithelial neoplasm, liver cancer, lung cancer, lymphoma, neuroblastoma, oral cancer, squamous cell carcinoma, ovarian cancer, pancreatic cancer, prostate cancer, colorectal cancer, sarcoma, skin cancer, testicular cancer, stromal tumour, germ cell tumour, thyroid cancer, or renal cancer.

19. The method according to claim 15, wherein: the brain cancer is glioblastoma or medulloblastoma; the haematological neoplasm is acute lymphocytic leukemia (ALL), chronic lymphocytic leukemia (CLL), chronic myelogenous leukemia (CML), acute myeloid leukaemia (AML), multiple myeloma, AIDS-associated leukemia or adult T-cell leukemia lymphoma; the intraepithelial neoplasm is Bowen's disease or Paget's disease; the lymphoma is Hodgkin's disease or lymphocytic lymphoma; the ovarian cancer is one arising from epithelial cells, stromal cells, germ cells or mesenchymal cells; the sarcoma is leiomyosarcoma, rhabdomyosarcoma, liposarcoma, fibrosarcoma or osteosarcoma; the skin cancer is melanoma, Kaposi's sarcoma, basocellular cancer or squamous cell cancer; the testicular cancer is seminoma, non-seminoma teratoma or choriocarcinoma; the thyroid cancer is thyroid adenocarcinoma or medullar carcinoma; and the renal cancer is adenocarcinoma and Wilms' tumour.

20. The method according to claim 18, wherein: the brain cancer is glioblastoma or medulloblastoma; the haematological neoplasm is acute lymphocytic leukemia (ALL), chronic lymphocytic leukemia (CLL), chronic myelogenous leukemia (CML), acute myeloid leukaemia (AML) multiple myeloma, AIDS-associated leukemia or adult T-cell leukemia lymphoma; the intraepithelial neoplasm is Bowen's disease or Paget's disease; the lymphoma is Hodgkin's disease or lymphocytic lymphoma; the ovarian cancer is one arising from epithelial cells, stromal cells, germ cells or mesenchymal cells; the sarcoma is leiomyosarcoma, rhabdomyosarcoma, liposarcoma, fibrosarcoma or osteosarcoma; the skin cancer is melanoma, Kaposi's sarcoma, basocellular cancer or squamous cell cancer; the testicular cancer is seminoma, non-seminoma teratomas or choriocarcinoma; the thyroid cancer is thyroid adenocarcinoma or medullar carcinoma; and the renal cancer is adenocarcinoma and Wilms' tumour.

21. The compound of claim 1, wherein $R^1$, $R^2$ and $R^3$ are each independently selected from the group consisting of H, alkyl, $NH_2$, NH-alkyl, S—$C_{1-6}$ alkyl, halogen or CN.

22. The compound of claim 21, wherein $R^9$ is H or a $C_{1-6}$ alkyl.

23. The compound of claim 1, wherein the compound is selected from:
- 1-(4-Methyl-5-(2-(methylamino)-pyrimidin-4-yl)thiazol-2-yl)-3-(3-(trifluoromethyl)phenyl)urea;
- 1-(3-Bromophenyl)-3-(4-methyl-5-(2-(methylamino)pyrimidin-4-yl)thiazol-2-yl)urea;
- 1-(4-Methyl-5-(2-(methylamino)pyrimidin-4-yl)thiazol-2-yl)-3-(m-tolyl)urea;
- 1-(3-Cyanophenyl)-3-(4-methyl-5-(2-(methylamino)pyrimidin-4-yl)thiazol-2-yl)urea;
- 1-(3-Methoxyphenyl)-3-(4-methyl-5-(2-(methylamino)pyrimidin-4-yl)thiazol-2-yl)urea;
- 1-(3-Ethoxyphenyl)-3-(4-methyl-5-(2-(methylamino)pyrimidin-4-yl)thiazol-2-yl)urea;
- 1-(3-(Difluoromethoxy)phenyl)-3-(4-methyl-5-(2-(methylamino)-pyrimidin-4-yl)thiazol-2-yl)urea;
- 1-(4-Methyl-5-(2-(methylamino)-pyrimidin-4-yl)thiazol-2-yl)-3-(3-(methylthio)phenyl)urea;
- 1-(4-Chloro-3-methylphenyl)-3-(4-methyl-5-(2-(methylamino)-pyrimidin-4-yl)thiazol-2-yl)urea;
- 1-(3-Chloro-4-(morpholinomethyl)phenyl)-3-(4-methyl-5-(2-(methylamino)-pyrimidin-4-yl)thiazol-2-yl)urea;
- 1-(4-Methyl-5-(2-(methylamino)-pyrimidin-4-yl)thiazol-2-yl)-3-(4-((4-methylpiperazin-1-yl)methyl)-3-(trifluoromethyl)phenyl)urea;
- 1-(4-((4-Ethylpiperazin-1-yl)methyl)-3-(trifluoromethyl)phenyl)-3-(4-methyl-5-(2-(methylamino)-pyrimidin-4-yl)thiazol-2-yl)urea;
- 1-(4-((4-Isopropylpiperazin-1-yl)methyl)-3-(trifluoromethyl)-phenyl)-3-(4-methyl-5-(2-(methylamino)pyrimidin-4-yl)thiazol-2-yl)urea;
- 1-(4-((4-Acetylpiperazin-1-yl)methyl)-3-(trifluoromethyl)-phenyl)-3-(4-methyl-5-(2-(methylamino)pyrimidin-4-yl)thiazol-2-yl)urea;
- 1-(4-Methyl-5-(2-(methylamino)-pyrimidin-4-yl)thiazol-2-yl)-3-(4-((4-(methylsulfonyl)piperazin-1-yl)methyl)-3-(trifluoromethyl)-phenyl)urea;
- 1-(4-Methyl-5-(2-(methylamino)-pyrimidin-4-yl)thiazol-2-yl)-3-(4-(morpholinomethyl)-3-(trifluoromethyl)phenyl)urea;
- 1-(4-((4-Aminopiperidin-1-yl)methyl)-3-(trifluoromethyl)-phenyl)-3-(4-methyl-5-(2-(methylamino)pyrimidin-4-yl)thiazol-2-yl)urea;
- 1-(4-Chlorophenyl)-3-(4-methyl-5-(2-(methylamino)pyrimidin-4-yl)thiazol-2-yl)urea;
- 1-(4-Methyl-5-(2-(methylamino)pyrimidin-4-yl)thiazol-2-yl)-3-(p-tolyl)urea;
- 1-(4-Methoxyphenyl)-3-(4-methyl-5-(2-(methylamino)pyrimidin-4-yl)thiazol-2-yl)urea;
- 1-(5-(2-(Dimethylamino)pyrimidin-4-yl)-4-methylthiazol-2-yl)-3-(4-((4-methylpiperazin-1-yl)methyl)-3-(trifluoromethyl)phenyl)urea;
- 1-(5-(2-(Ethylamino)pyrimidin-4-yl)-4-methylthiazol-2-yl)-3-(4-((4-methylpiperazin-1-yl)methyl)-3-(trifluoromethyl)phenyl)urea;
- 1-(5-(2-(Ethylamino)pyrimidin-4-yl)-4-methylthiazol-2-yl)-3-(4-((4-ethylpiperazin-1-yl)methyl)-3-(trifluoromethyl)phenyl)urea;
- 1-(5-(2-(ethylamino)pyrimidin-4-yl)-4-methylthiazol-2-yl)-3-(4-((4-isopropylpiperazin-1-yl)methyl)-3-(trifluoromethyl)phenyl)urea;
- 1-(4-((4-Acetylpiperazin-1-yl)methyl)-3-(trifluoromethyl)-phenyl)-3-(5-(2-(ethylamino)-pyrimidin-4-yl)-4-methylthiazol-2-yl)urea;
- 1-(5-(2-(Methylamino)pyrimidin-4-yl)thiazol-2-yl)-3-(4-((4-methylpiperazin-1-yl)methyl)-3-(trifluoromethyl)phenyl)urea;
- 1-(4-((4-Ethylpiperazin-1-yl)methyl)-3-(trifluoromethyl)phenyl)-3-(5-(2-(methylamino)pyrimidin-4-yl)thiazol-2-yl)urea;
- 1-(4-((4-Isopropylpiperazin-1-yl)methyl)-3-(trifluoromethyl)phenyl)-3-(5-(2-(methylamino)pyrimidin-4-yl)thiazol-2-yl)urea;
- 1-(4-((4-Acetylpiperazin-1-yl)methyl)-3-(trifluoromethyl)phenyl)-3-(5-(2-(methylamino)pyrimidin-4-yl)thiazol-2-yl)urea;
- 1-(5-(2-Aminopyrimidin-4-yl)-4-methylthiazol-2-yl)-3-(4-((4-ethylpiperazin-1-yl)methyl)-3-(trifluoromethyl)phenyl)urea;
- 1-(5-(2-Aminopyrimidin-4-yl)-4-methylthiazol-2-yl)-3-(4-((4-isopropylpiperazin-1-yl)methyl)-3-(trifluoromethyl)phenyl)urea;

1-(5-(2-Aminopyrimidin-4-yl)-4-methylthiazol-2-yl)-3-(4-(morpholinomethyl)-3-(trifluoromethyl)phenyl)urea;

1-(5-(5-Chloro-2-(methylamino)pyrimidin-4-yl)-4-methylthiazol-2-yl)-3-(4-((4-methylpiperazin-1-yl)methyl)-3-(trifluoromethyl)phenyl)urea;

1-(5-(5-Chloro-2-(methylamino)pyrimidin-4-yl)-4-methylthiazol-2-yl)-3-(4-((4-ethylpiperazin-1-yl)methyl)-3-(trifluoromethyl)phenyl)urea;

1-(5-(5-Chloro-2-(methylamino)pyrimidin-4-yl)-4-methylthiazol-2-yl)-3-(4-((4-isopropylpiperazin-1-yl)methyl)-3-(trifluoromethyl)phenyl)urea;

1-(4-((4-Acetylpiperazin-1-yl)methyl)-3-(trifluoromethyl)phenyl)-3-(5-(5-chloro-2-(methylamino)pyrimidin-4-yl)-4-methylthiazol-2-yl)urea;

1-(5-(5-Fluoro-2-(methylamino)pyrimidin-4-yl)-4-methylthiazol-2-yl)-3-(4-(morpholinomethyl)-3-(trifluoromethyl)phenyl)urea;

1-(5-(5-Cyano-2-(methylamino)pyrimidin-4-yl)-4-methylthiazol-2-yl)-3-(4-((4-methylpiperazin-1-yl)methyl)-3-(trifluoromethyl)phenyl)urea;

1-(5-(5-Cyano-2-(methylamino)pyrimidin-4-yl)-4-methylthiazol-2-yl)-3-(4-((4-ethylpiperazin-1-yl)methyl)-3-(trifluoromethyl)phenyl)urea;

1-(5-(5-Cyano-2-(methylamino)pyrimidin-4-yl)-4-methylthiazol-2-yl)-3-(4-((4-isopropylpiperazin-1-yl)methyl)-3-(trifluoromethyl)phenyl)urea;

1-(5-(2-Isopropylpyrimidin-4-yl)-4-methylthiazol-2-yl)-3-(4-((4-methylpiperazin-1-yl)methyl)-3-(trifluoromethyl)phenyl)urea;

1-(4-((4-Acetylpiperazin-1-yl)methyl)-3-(trifluoromethyl)phenyl)-3-(5-(2-isopropylpyrimidin-4-yl)-4-methylthiazol-2-yl)urea; and 1-(4-Methyl-5-(2-(methylthio)pyrimidin-4-yl)thiazol-2-yl)-3-(4-((4-methyl-piperazin-1-yl)methyl)-3-(trifluoromethyl)phenyl)urea.

24. A pharmaceutical composition or medicament comprising a compound according to claim 23 and a pharmaceutically acceptable carrier, diluent and/or excipient.

25. A method of treating cancer or another proliferative cell disease or condition in a subject, the method comprising administering to said subject a therapeutically effective amount of a compound according to claim 23, optionally in combination with a pharmaceutically acceptable carrier, diluent and/or excipient, wherein the cancer or proliferative cell disease is colorectal cancer, biliary tract cancer, brain cancer, breast cancer, cervical cancer, choriocarcinoma, endometrial cancer, oesophageal cancer, gastric cancer, haematological neoplasm, intraepithelial neoplasm, liver cancer, lung cancer, lymphoma, neuroblastoma, oral cancer, squamous cell carcinoma, ovarian cancer, pancreatic cancer, prostate cancer, colorectal cancer, sarcoma, skin cancer, testicular cancer, stromal tumour, germ cell tumour, thyroid cancer, and renal cancer.

* * * * *